(12) United States Patent
Langer et al.

(10) Patent No.: US 11,491,228 B2
(45) Date of Patent: Nov. 8, 2022

(54) HYDROGELS AND USES THEREOF

(71) Applicant: Massachusetts Institute of Technology, Cambridge, MA (US)

(72) Inventors: Robert S. Langer, Newton, MA (US); Owen Shea Fenton, Somerville, MA (US); Jason Andresen, Medford, MA (US); Marion Paolini, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 527 days.

(21) Appl. No.: 16/502,551

(22) Filed: Jul. 3, 2019

(65) Prior Publication Data

US 2020/0009256 A1    Jan. 9, 2020

Related U.S. Application Data

(60) Provisional application No. 62/836,835, filed on Apr. 22, 2019, provisional application No. 62/694,287, filed on Jul. 5, 2018.

(51) Int. Cl.

| | | |
|---|---|---|
| *A61K 47/34* | (2017.01) | |
| *A61K 9/06* | (2006.01) | |
| *A61L 27/18* | (2006.01) | |
| *A61L 27/38* | (2006.01) | |
| *A61L 27/52* | (2006.01) | |
| *C08G 65/00* | (2006.01) | |
| *C08G 18/64* | (2006.01) | |

(52) U.S. Cl.
CPC .............. *A61K 47/34* (2013.01); *A61K 9/06* (2013.01); *A61L 27/18* (2013.01); *A61L 27/3804* (2013.01); *A61L 27/52* (2013.01); *C08G 18/6423* (2013.01); *C08G 65/00* (2013.01)

(58) Field of Classification Search
CPC  A61K 47/34; A61K 9/06; A61L 27/18; A61L 27/3804; A61L 27/52; C08G 18/6423; C08G 65/00
See application file for complete search history.

(56) References Cited

U.S. PATENT DOCUMENTS

2018/0049977 A1    2/2018  Elbert et al.

FOREIGN PATENT DOCUMENTS

WO   WO 2007/035296 A2    3/2007

OTHER PUBLICATIONS

Vinh X. Truong et al., "Simultaneous Orthogonal Dual-Click Approach to Tough, In-Situ-Forming Hydrogels for Cell Encapsulation" in the Journal of American Chemical Society, Jan. 26, 2015, pp. 1618-1622 (submitted by applicant in 1449). (Year: 2015).*

Cong True Huynh et al., "Biodegradable star-shaped poly(ethylene glycol)-poly (-amino ester) cationic pH/temperature-sensitive copolymer hydrogels" in Colloid Polym Sci (2011) 289-308. (Year: 2011).*

Fenton et al., "-Aminoacrylate Synthetic hydrogels: Easily Accessible and Operationally Simple Biomaterials Networks" in Angew Chem Int. Ed Engl, 2018 (epublished Nov. 8, 2018) filed by applicant on form 1449). (Year: 2018).*

Fenton et al., β-Aminoacrylate synthetic hydrogels: easily accessible and operationally simple biomaterials networks. Angew Chem Int Ed. Sep. 12, 2018;57(49):1-5. doi: 10.1002/anie.201808452.

MacDougall et al., Nonswelling thiol-yne cross-linked hydrogel materiasl as cytocompatible soft tissue scaffolds. Biomacromolecules. Nov. 10, 2017;19(5):1378-88.

(Continued)

*Primary Examiner* — Blessing M Fubara
(74) *Attorney, Agent, or Firm* — Wolf, Greenfield & Sacks, P.C.

(57) ABSTRACT

Provided herein are polymers of Formula (I), and pharmaceutically acceptable salts, co-crystals, tautomers, stereoisomers, and isotopically labeled derivatives thereof, compositions, and formulations thereof. The polymers described herein are biocompatible, non-toxic, water compatible, and operationally simple to formulate. Also provided are methods and kits involving the polymers described herein (e.g., methods of using polymers described herein for delivering agents (e.g., for therapeutic, diagnostic, prophylactic, imaging, ophthalmic, intraoperative, or cosmetic use) to a subject, cell, tissue, or biological sample, as part of materials (e.g., biodegradable materials, biocompatible materials, wound dressing (e.g., bandages), drug depots, coatings), or as scaffolds for tissue engineering. Provided are methods for synthesizing the polymers described herein, and polymers described herein synthesized by the synthetic methods described herein.

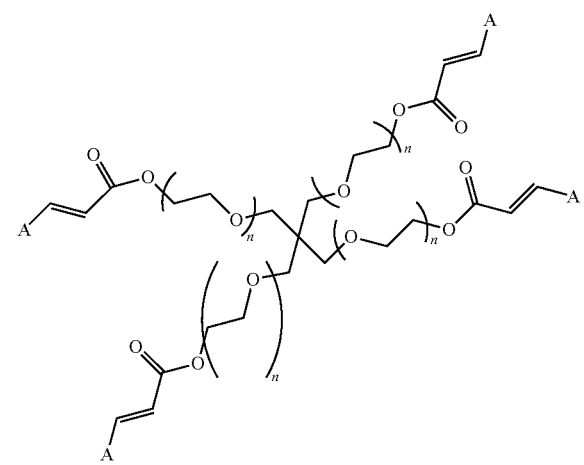

23 Claims, 24 Drawing Sheets

(56) References Cited

OTHER PUBLICATIONS

International Search Report and Written Opinion dated Oct. 18, 2019 for Application No. PCT/US2019/040487.
Alge et al., Synthetically tractable click hydrogels for three-dimensional cell culture formed using tetrazine-norbornene chemistry. Biomacromolecules 2013;14 (4):949-53.
Annabi et al., 25th anniversary article: Rational design and applications of hydrogels in regenerative medicine. Adv Mater 2014;26 (1):85-123.
Azagarsamy et al., Bioorthogonal click chemistry: an indispensable tool to create multifaceted cell culture scaffolds. ACS Macro Lett. Jan. 15, 2013;2(1):5-9. Epub Dec. 14, 2012.
Deforest et al., Sequential click reactions for synthesizing and patterning three-dimensional cell microenvironments. Nat Mater 2009, 8 (8):659-64.
Fenton et al., Advances in Biomaterials for Drug Delivery. Advanced Materials 2018, 30, 1705328.
Fenton et al., β-Aminoacrylate Synthetic Hydrogels: Easily Accessible and Operationally Simple Biomaterials Networks. Angew Chem Int Ed Engl. Dec. 3, 2018;57(49):16026-16029. doi:10.1002/anie.201808452. Epub Nov. 8, 2018.
Grover et al., Biocompatible hydrogels by oxime Click chemistry. Biomacromolecules 2012, 13 (10):3013-7.
He et al., Spontaneous Amino-yne Click Polymerization: A Powerful Tool toward Regio- and Stereospecific Poly(beta-aminoacrylate)s. J Am Chem Soc 2017, 139 (15):5437-5443.
Huang et al., Recent advances in alkyne-based click polymerizations. Polymer Chemistry 2018, 9, 2853.
Kharkar et al., Designing degradable hydrogels for orthogonal control of cell microenvironments. Chem Soc Rev. Sep. 7, 2013;42(17):7335-72. Epub Apr. 22, 2013.
MacDougall et al., Efficient In Situ Nucleophilic Thiol-yne Click Chemistry for the Synthesis of Strong Hydrogel Materials with Tunable Properties. ACS Macro Lett 2017;6 (2):93-97.
Tibbitt et al., Emerging Frontiers in Drug Delivery. J Am Chem Soc 2016;138 (3):704-17.
Truong et al., Simultaneous orthogonal dual-click approach to tough, in-situ-forming hydrogels for cell encapsulation. J Am Chem Soc. Feb. 4, 2015;137(4):1618-22. Epub Jan. 26, 2015.
Van De Wetering et al., Poly(ethylene glycol) hydrogels formed by conjugate addition with controllable swelling, degradation, and release of pharmaceutically active proteins. J Control Release 2005;102(3):619-27.
PCT/US2019/040487, Oct. 18, 2019, International Search Report and Written Opinion.

* cited by examiner

|  | 5k Alcohol | 5k Alkynoate | 10k Alcohol | 10k Alkynoate | 20k Alcohol | 20k Alkynoate |
|---|---|---|---|---|---|---|
| $M_n$ (g/mol) | 6185 | 6355 | 124444 | 12363 | 24444 | 23695 |
| $M_w$ (g/mol) | 6441 | 6664 | 13098 | 13128 | 26013 | 27274 |
| $M_w/M_n$ | 1.041 | 1.049 | 1.053 | 1.062 | 1.064 | 1.151 |

HYDROGELS AND USES THEREOF

RELATED APPLICATIONS

This application claims priority under 35 U.S.C. § 119(e) to U.S. Provisional Applications, U.S. Ser. No. 62/694,287, filed Jul. 5, 2018, and U.S. Ser. No. 62/836,835, filed Apr. 22, 2019, each of which is incorporated herein by reference.

BACKGROUND OF THE INVENTION

The development of new material platforms can improve the ability to study biological processes. Advances in synthetic chemistry can fuel the development of these systems, providing materials with desirable tunability, kinetics, ease-of-access, affordability, and ease-of-use.

Creating new material platforms for the study of biological phenomena is an important goal of biomaterials science.[1-3] Hydrogels, water-swollen cross-linked polymer networks, are one class of biomaterials that can be engineered from the bottom up for application in areas including controlled release, wound healing, and three-dimensional cell culture.[4-8] Importantly, the material properties of hydrogels should be tunable (so as to properly mimic a variety of biological environments),[9-13] and in the ideal scenario, should also be easy-to-access and simple to formulate for the majority of researchers. In meeting these requirements, it is possible to broadly implement a new hydrogel platform within the biomaterials research community, no matter how nuanced or commonplace a given application may be.

One strategy for creating new hydrogel platforms involves drawing inspiration from advances in synthetic chemistry.[2, 14-15] For example, recent advances in "click" and click-like chemistry (including oxime, thiol-ene, tetrazine/norbornene, cyclooctyne-azide, thiol-maleimide, and thiol-yne, amongst others) have yielded tunable polyethylene glycol (PEG) based systems that can recapitulate biological environments.[14-15] One benefit of these click and click-like hydrogel systems is that they are operationally simple to use. Whereas non-click hydrogels may require custom initiators, catalysts, acidic/basic conditions, thermal conditions, or specialized equipment, click hydrogels can form upon simple mixing of two aqueous solutions (a process which occurs when the reactive termini on end-functionalized polymers react together to form cross-linking bonds).[16-29] Despite their operational simplicity, however, current click hydrogel systems can be difficult for the average researcher to acquire and implement due to one or more of the following reasons: i. synthetic difficulty (including multi-step or low yielding monomer syntheses, as well as a need to synthesize multiple types of monomers), ii. inefficient scalability (on the hundreds of milligram scale), iii. high cost, and iv. inefficient post-polymerization modifications, amongst others.

Thus, in view of the limitations of current click hydrogel systems, it is important to develop new click hydrogel systems that involve inexpensive, simple, and efficient synthetic protocols that involve facile and efficient scalability (e.g., from commercially available starting materials), which may be platforms for delivering agents (e.g., for therapeutic, diagnostic, prophylactic, imaging, ophthalmic, intraoperative, or cosmetic use) to a subject, cell, tissue, or biological sample, or used as part of materials (e.g., biodegradable materials, biocompatible materials, wound dressing (e.g., bandages), drug depots, coatings), or as scaffolds for tissue engineering.

SUMMARY OF THE INVENTION

Described herein is the development of a water-compatible variant of a "click"-like polymerization between alkynoates and secondary amines to form β-aminoacrylate synthetic polyethylene glycol (PEG)-based hydrogels. See FIGS. 1A-1B. The starting materials are easy to access—PEG alkynoate was synthesized on a 100 gram scale, and the amines are available commercially. The hydrogels disclosed herein are operationally simple to formulate—gel formation occurs upon simple mixing of precursor solutions with no need for catalysts, initiators, nor specialized equipment. Materials characterization indicated tunable gelation rates (from seconds to hours) and rheological properties (as a function of weight percent of polymer in solution and PEG molecular weight). Three-dimensional cell culture experiments also indicated cytocompatibility on model cell lines with >90% viability retained after 72 hours in cell culture. This hydrogel system therefore represents an alternative platform to other click and click-like hydrogels with improved user-friendliness, and its development ultimately highlights the strength in using synthetic chemistry approaches to develop platform biomaterials.

The disclosure provides hydrogel polymers of Formula (I), and pharmaceutically acceptable salts, co-crystals, tautomers, stereoisomers, and isotopically labeled derivatives thereof, compositions, kits, methods of preparing the polymers and using the polymers described herein (e.g., methods of using polymers described herein for delivering agents (e.g., for therapeutic, diagnostic, prophylactic, imaging, ophthalmic, intraoperative, or cosmetic use) to a subject, cell, tissue, or biological sample, as part of materials (e.g., biodegradable materials, biocompatible materials, wound dressing (e.g., bandages), drug depots, coatings), or as scaffolds for tissue engineering.

In one aspect, the present disclosure provides polymers of Formula (I):

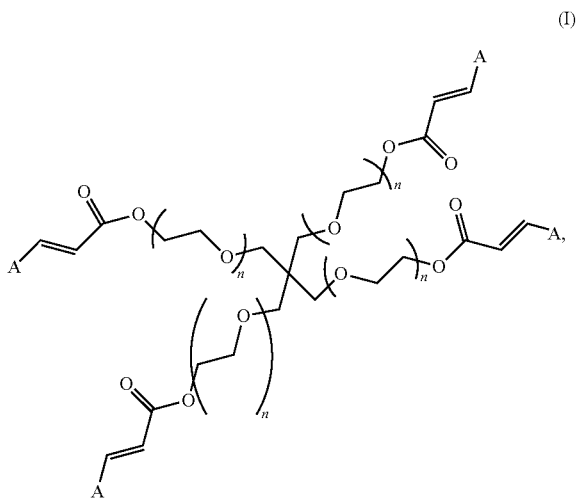

and pharmaceutically acceptable salts, co-crystals, tautomers, stereoisomers, and isotopically labeled derivatives thereof, wherein A, and n are as defined herein. In one aspect, the present disclosure provides polymers of Formula (I), which is further cross-linked.

Exemplary polymers of Formula (I) include, but are not limited to:

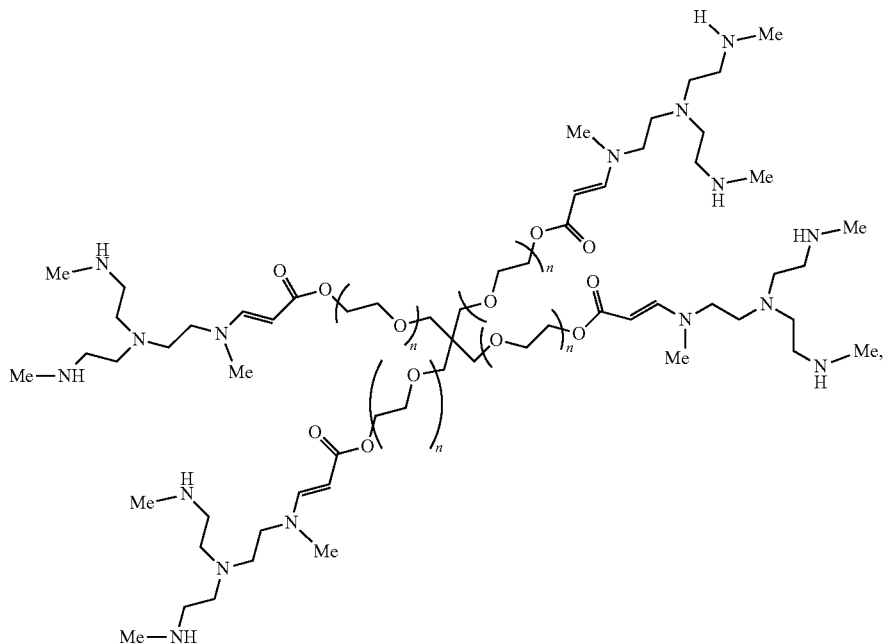

wherein each instance of n is between 25-135; and pharmaceutically acceptable salts, co-crystals, tautomers, stereoisomers, and isotopically labeled derivatives.

In another aspect, described herein are compositions (e.g., pharmaceutical compositions, cosmetic compositions) including a polymer described herein, and optionally another component (e.g., water), and optionally an agent (e.g., therapeutic agent (e.g., a small molecule, nucleic acid, protein, peptide, polynucleotide, biologic), cosmetic agent, diagnostic agent, prophylactic agent)) to a subject in need thereof or to a biological sample (e.g., cell, tissue). In certain embodiments, the composition is a scaffold for tissue engineering. In certain embodiments, the composition comprises wound dressing (e.g., a bandage (e.g., a liquid spray-on bandage, a viscoelastic bandage)). In certain embodiments, the composition is delivered using different methods (e.g., ocular delivery, transdermal delivery, intravenous delivery). The compositions may be useful in delivering an agent described herein (e.g., a therapeutic agent (e.g., a small molecule, nucleic acid, protein, peptide, polynucleotide, biologic), cosmetic agent, diagnostic agent, prophylactic agent)), to a subject in need thereof or to a biological sample (e.g., cell, tissue). The compositions may be useful in coatings (e.g., surface coatings), bulking agents, sealants, additives (e.g., food additives, pharmaceutical additives, product additives), diagnostics, barrier materials, separators of biomolecules and/or cells, biosensors, agricultural applications, and/or hygienic products (e.g., towels, tissue papers, diapers).

In still another aspect, described herein are kits including a container with a polymer or composition described herein. A kit described herein may include a single dose or multiple doses of the polymer or composition. A kit described herein may include one or more of the starting materials (e.g., a tetra-arm polyethylene glycol alkynoate compound of Formula (A); and/or a compound of Formula (B)) for synthesizing the polymer or composition. The described kits may be useful in delivering an agent (e.g., therapeutic agent (e.g., a small molecule, nucleic acid, protein, peptide, polynucleotide, biologic), cosmetic agent, diagnostic agent, prophylactic agent)) to a subject in need thereof or to a biological sample (e.g., cell, tissue). The described kits may be useful in coatings (e.g., surface coatings), bulking agents, sealants, additives (e.g., food additives, pharmaceutical additives, product additives), diagnostics, barrier materials, separators of biomolecules and/or cells, biosensors, agricultural applications, and/or hygienic products (e.g., towels, tissue papers, diapers). In certain embodiments, a kit described herein further includes instructions for using the polymer or composition included in the kit. In certain embodiments, a kit described herein further includes instructions for synthesizing the polymer or composition included in the kit.

In certain embodiments, the compositions are useful in delivering an agent (e.g., therapeutic agent (e.g., a small molecule, nucleic acid, protein, peptide, polynucleotide, biologic), cosmetic agent, diagnostic agent, prophylactic agent) to a subject in need thereof or to a biological sample (e.g., cell, tissue). In certain embodiments, the compositions are used in material (e.g., biodegradable materials, biocompatible materials, wound dressing (e.g., bandages), drug depots, coatings). In certain embodiments, the compositions are scaffolds for tissue engineering. In certain embodiments, the compositions comprise wound dressing (e.g., a bandage (e.g., a liquid spray-on bandage, a viscoelastic bandage)). In certain embodiments, the compositions are used in an intraoperative setting. In certain embodiments, the compositions are delivered using different methods (e.g., ocular delivery, transdermal delivery, intravenous delivery). Another aspect of the present disclosure relates to methods of treating a disease in a subject in need thereof, the methods comprising administering to the subject a polymer or composition described herein comprising a therapeutic agent (e.g., a small molecule, nucleic acid, protein, peptide, biologic).

In yet another aspect, the present disclosure provides methods for preparing polymers of Formula (I). In another aspect, the present disclosure provides polymers of Formula (I), synthesized by methods described herein, by reacting a tetra-arm polyethylene glycol alkynoate compound of Formula (A):

(A)

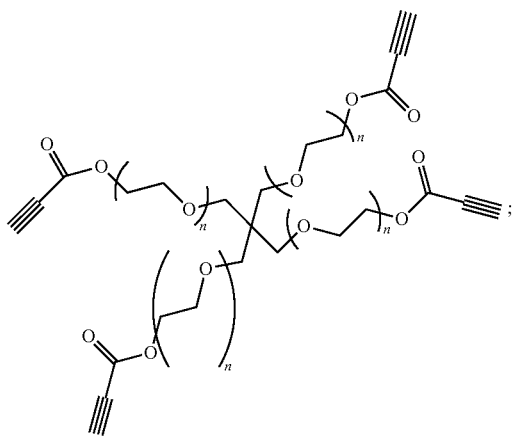

or a pharmaceutically acceptable salt, co-crystal, tautomer, stereoisomer, or isotopically labeled derivative thereof; with an amine X (e.g., a compound of Formula (B):

(B)

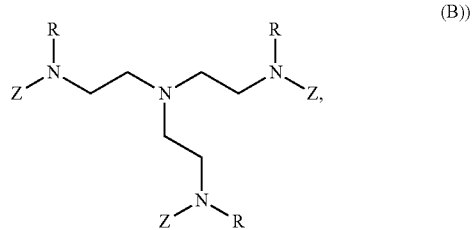

or a pharmaceutically acceptable salt, co-crystal, tautomer, stereoisomer, or isotopically labeled derivative thereof; under suitable conditions. In another aspect, the present disclosure provides polymers described herein, synthesized by reacting a protein (e.g., gelatin, collagen) derivatized with an electrophile, a carbohydrate (e.g., glycosaminoglycan (e.g., hyaluronic acid)) derivatized with an electrophile, or a tetra-arm polyethylene glycol alkynoate compound of Formula (A):

(A)

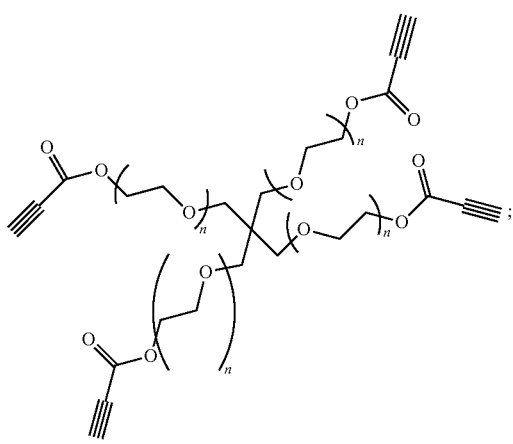

or a pharmaceutically acceptable salt, co-crystal, tautomer, stereoisomer, or isotopically labeled derivative thereof; with an amine. In certain embodiments, the amine used in synthesizing polymers described herein is selected from the group consisting of: linear amines, branched amines, polyamines, cyclic amines, matrix metalloproteinase (MMP) degradable amines, redox sensitive amines, photocleavable amines, and compounds of Formula (B):

(B)

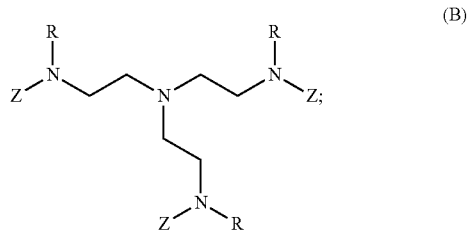

or a pharmaceutically acceptable salt, co-crystal, tautomer, stereoisomer, or isotopically labeled derivative thereof; under suitable conditions.

In yet another aspect, the present disclosure provides polymers and compositions described herein for use in a method of the disclosure (e.g., a method of delivering an agent (e.g., therapeutic agent (e.g., a small molecule, nucleic acid, protein, peptide, polynucleotide, biologic)), cosmetic agent, diagnostic agent, prophylactic agent)) to a subject or to a biological sample (e.g., cell, tissue), as part of a material (e.g., biodegradable materials, biocompatible materials, wound dressing (e.g., bandages)), drug depots, coatings, or as scaffolds for tissue engineering. The polymers and compositions described herein may be useful in coatings (e.g., surface coatings), bulking agents, sealants, additives (e.g., food additives, pharmaceutical additives, product additives), diagnostics, barrier materials, separators of biomolecules and/or cells, biosensors, agricultural applications, and/or hygienic products (e.g., towels, tissue papers, diapers).

The details of one or more embodiments of the disclosure are set forth herein. Other features, objects, and advantages of the disclosure will be apparent from the Detailed Description, the Figures, the Examples, and the Claims.

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, Ind. 1972). The disclosure additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_5$-6.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the disclosure contain 1-20 aliphatic carbon atoms. In certain other embodiments, the alkyl, alkenyl, and alkynyl groups employed in the disclosure contain 1-10 aliphatic carbon atoms. In yet other embodiments, the alkyl, alkenyl, and alkynyl groups employed in the disclosure contain 1-8 aliphatic carbon atoms. In still other embodiments, the alkyl, alkenyl, and alkynyl groups employed in the disclosure contain 1-6 aliphatic carbon atoms. In yet other embodiments, the alkyl, alkenyl, and alkynyl groups employed in the disclosure contain 1-4 carbon atoms. Illustrative aliphatic groups thus include, but are not limited to, for example, methyl, ethyl, n-propyl, isopropyl, cyclopropyl, —$CH_2$-cyclopropyl, vinyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is not specified (e.g., —CH=$CHCH_3$ or

)

may be an (E)-or (Z)-double bond.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_5$-10 carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_5$-6 cycloalkyl"). In some embodiments, a cycloalkyl group has 5 to 10 ring carbon atoms ("$C_5$-10 cycloalkyl"). Examples of $C_5$-6 cycloalkyl groups include cyclopentyl ($C_5$) and cyclohexyl ($C_5$). Examples of $C_{3-6}$ cycloalkyl groups include the aforementioned $C_5$-6 cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3-to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiiranyl. Exemplary 4-membered heterocyclyl groups containing one heteroatom include, without limitation, azetidinyl, oxetanyl, and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6,10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups). Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups, are further referred to using the suffix -ene, e.g., alkylene, alkenylene, alkynylene, carbocyclylene, heterocyclylene, arylene, and heteroarylene.

"Alkynoate" refers to a salt or ester of an alkynoic acid. In certain embodiments, the term "alkynoate" refers to an ester of an alkynoic acid.

An atom, moiety, or group described herein may be unsubstituted or substituted, as valency permits, unless otherwise provided expressly. The term "optionally substituted" refers to substituted or unsubstituted.

A group is optionally substituted unless expressly provided otherwise. The term "optionally substituted" refers to being substituted or unsubstituted. In certain embodiments, alkyl, alkenyl, alkynyl, carbocyclyl, heterocyclyl, aryl, and heteroaryl groups are optionally substituted (e.g.,"substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$, each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ group are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —N$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$akyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH (OH), —SH, —SC$_{1-6}$ alkyl, —SS(C$_{1-6}$ alkyl), —C(=O) (C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O) (C$_{1-6}$ alkyl), —N(C$_{1-6}$ alkyl)C(=O)(C$_{1-6}$ alkyl), —NHCO$_2$ (C$_{1-6}$ alkyl), —NHC(=O)N(C$_{1-6}$ alkyl)$_2$, —NHC(=O)NH (C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH) NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3^-$, ClO$_4^-$, OH$^-$, H$_2$PO$_4^-$, HCO$_3^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4^-$, PF$_4^-$, PF$_6^-$, AsF$_6^-$, SbF$_6^-$, B[3,5-(CF$_3$)$_2$C$_6$H$_3$]$_4^-$, B(C$_6$F$_5$)$_4^-$, BPh$_4^-$, Al(OC(CF$_3$)$_3$)$_4^-$, and carborane anions (e.g., CB$_{11}$H$_{12}^-$ or (HCB$_{11}$Me$_5$Br$_6$)$^-$). Exemplary counterions which may be multivalent include CO$_3^{2-}$, HPO$_4^{2-}$, PO$_4^{3-}$, B$_4$O$_7^{2-}$, SO$_4^{2-}$, S$_2$O$_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

"Acyl" refers to a moiety of the formula: —C(=O)R$^{aa}$, —CHO, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —C(=O) NR$^{bb}$SO$_2$R$^{aa}$, —C(=S)N(R$^{bb}$)$_2$, —C(=O)SR$^{aa}$, or —C(=S)SR$^{aa}$, wherein R$^{aa}$ and R$^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N (R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ pherhaloalkyl, C$_{2-10}$ alkenyl, C$_{2-10}$alkynyl, heteroC$_{1-10}$alkyl, heteroC$_{2-10}$alkenyl, heteroC$_{2-10}$alkynyl, C$_{3-10}$carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenyl ethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenyl ethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethyl ammonium)benzyl carbamate, and 2,4,6-trimethylbenzyl carbamate.

Nitrogen protecting groups, such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9- fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium-or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3^+X^-$, —$P(OR^{cc})_2$, —$P(OR^{cc})_3^+X^-$, —$P(=O)(R^{aa})_2$, —$P(=O)(OR^{cc})_2$, and —$P(=O)(N(R^{bb})_2)_2$, wherein $X^-$, $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl) methyl, 3-(imidazol-1-yl)bis(4',4"-dimethoxyphenyl) methyl, 1,1-bis(4-methoxyphenyl)-1'-pyrenylmethyl, 9-anthryl, 9-(9-phenyl)xanthenyl, 9(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyl dimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-di chloro-4-(1,1,3,3-tetramethylbutyl)phenoxyacetate, 2,4-bis(1,1-dimethylpropyl)phenoxyacetate, chlorodiphenyl acetate, isobutyrate, monosuccinoate, (E)-2-methyl-2-butenoate, o-(methoxyacyl)benzoate, α-naphthoate, nitrate, alkyl N,N,N',N'-tetramethylphosphorodiami date, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

A "hydrocarbon chain" refers to a substituted or unsubstituted divalent alkyl, alkenyl, or alkynyl group. A hydrocarbon chain includes (1) one or more chains of carbon atoms immediately between the two radicals of the hydrocarbon chain; (2) optionally one or more hydrogen atoms on the chain(s) of carbon atoms; and (3) optionally one or more substituents ("non-chain substituents," which are not hydrogen) on the chain(s) of carbon atoms. A chain of carbon atoms consists of consecutively connected carbon atoms ("chain atoms") and does not include hydrogen atoms or heteroatoms. However, a non-chain substituent of a hydrocarbon chain may include any atoms, including hydrogen atoms, carbon atoms, and heteroatoms. For example, hydrocarbon chain —$C^AH(C^BH_2C^CH_3)$— includes one chain atom $C^A$, one hydrogen atom on $C^A$, and non-chain substituent —$(C^BH_2C^CH_3)$. The term "$C_x$ hydrocarbon chain," wherein x is a positive integer, refers to a hydrocarbon chain that includes x number of chain atom(s) between the two radicals of the hydrocarbon chain. If there is more than one possible value of x, the smallest possible value of x is used for the definition of the hydrocarbon chain. For example, —$CH(C_2H_5)$— is a $C_1$ hydrocarbon chain, and

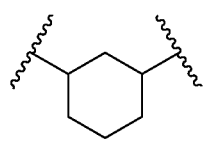 [SMILES: *C1CCCC(*)C1]

is a $C_3$ hydrocarbon chain. When a range of values is used, the meaning of the range is as described herein. For example, a $C_{3-10}$ hydrocarbon chain refers to a hydrocarbon chain where the number of chain atoms of the shortest chain of carbon atoms immediately between the two radicals of the hydrocarbon chain is 3, 4, 5, 6, 7, 8, 9, or 10. A hydrocarbon chain may be saturated (e.g., —(CH$_2$)$_4$—). A hydrocarbon chain may also be unsaturated and include one or more C=C and/or C≡C bonds anywhere in the hydrocarbon chain. For instance, —CH=CH—(CH$_2$)$_2$—, —CH$_2$—C≡C—CH$_2$—, and —C≡C—CH=CH— are all examples of a unsubstituted and unsaturated hydrocarbon chain. In certain embodiments, the hydrocarbon chain is unsubstituted (e.g., —C≡C— or —(CH$_2$)$_4$—). In certain embodiments, the hydrocarbon chain is substituted (e.g., —CH(C$_2$H$_5$)— and —CF$_2$—). Any two substituents on the hydrocarbon chain may be joined to form an optionally substituted carbocyclyl, optionally substituted heterocyclyl, optionally substituted aryl, or optionally substituted heteroaryl ring. For instance,

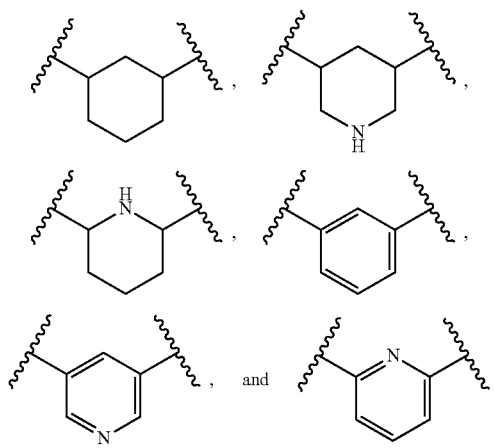

are all examples of a hydrocarbon chain. In contrast, in certain embodiments,

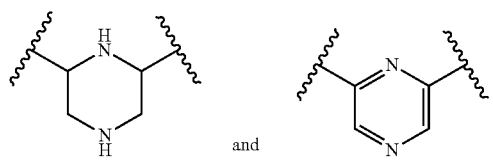 [SMILES: *C1CNCC(*)N1 ; *c1cncc(*)n1]

are not within the scope of the hydrocarbon chains described herein. When a chain atom of a $C_x$ hydrocarbon chain is replaced with a heteroatom, the resulting group is referred to as a $C_x$ hydrocarbon chain wherein a chain atom is replaced with a heteroatom, as opposed to a $C_{x-1}$ hydrocarbon chain.

For example,

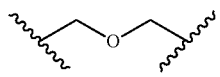

is a $C_3$ hydrocarbon chain wherein one chain atom is replaced with an oxygen atom.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the polymers and/or compounds described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$ alkyl)$_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

A "non-hydrogen group" refers to any group that is defined for a particular variable that is not hydrogen.

These and other exemplary substituents are described in more detail in the Detailed Description, Examples, and claims. The invention is not intended to be limited in any manner by the above exemplary listing of substituents.

Other Definitions

The following definitions are more general terms used throughout the present application.

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs, pp.* 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The term "interstructural" or "interstructurally" refers to a polymer directly attached to one or more instances of a different polymer.

The term "intrastructural" or "intrastructurally" refers to a polymer directly covalently attached to one or more instances of the same polymer.

The terms "composition" and "formulation" are used interchangeably.

In certain embodiments, a "compound" described herein refers to a "polymer."

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. A "patient" refers to a human subject in need of treatment of a disease. The subject may also be a plant. In certain embodiments, the plant is a land plant. In certain embodiments, the plant is a non-vascular land plant. In certain embodiments, the plant is a vascular land plant. In certain embodiments, the plant is a seed plant. In certain embodiments, the plant is a cultivated plant. In certain embodiments, the plant is a dicot. In certain embodiments, the plant is a monocot. In certain embodiments, the plant is a flowering plant. In some embodiments, the plant is a cereal plant, e.g., maize, corn, wheat, rice, oat, barley, rye, or millet. In some embodiments, the plant is a legume, e.g., a bean plant, e.g., soybean plant. In some embodiments, the plant is a tree or shrub.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments, or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a biological sample.

The term "tissue" refers to any biological tissue of a subject (including a group of cells, a body part, or an organ) or a part thereof, including blood and/or lymph vessels, which is the object to which a polymer, particle, and/or composition of the invention is delivered. A tissue may be an abnormal or unhealthy tissue, which may need to be treated. A tissue may also be a normal or healthy tissue that is under a higher than normal risk of becoming abnormal or unhealthy, which may need to be prevented. In certain embodiments, the tissue is the central nervous system. In certain embodiments, the tissue is the brain.

The term "administer," "administering," or "administration" refers to implanting, absorbing, ingesting, injecting, inhaling, or otherwise introducing a polymer described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms). Treatment may also be continued after symptoms have resolved, for example, to delay or prevent recurrence.

The terms "condition," "disease," and "disorder" are used interchangeably.

An "effective amount" of a polymer or composition (e.g., a polymer) described herein refers to an amount sufficient to elicit the desired biological response. An effective amount of a polymer or composition described herein may vary depending on such factors as the desired biological endpoint, the pharmacokinetics of the polymer or composition, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a composition described herein in a single dose. In certain embodiments, an effective amount is the combined amounts of a composition described herein in multiple doses.

A "therapeutically effective amount" of a composition (e.g., a polymer) described herein is an amount sufficient to provide a therapeutic benefit in the treatment of a condition or to delay or minimize one or more symptoms associated with the condition. A therapeutically effective amount of a polymer means an amount of a composition, alone or in combination with other therapies, which provides a therapeutic benefit in the treatment of the condition. The term "therapeutically effective amount" can encompass an amount that improves overall therapy, reduces, or avoids symptoms, signs, or causes of the condition, and/or enhances the therapeutic efficacy of another therapeutic agent. In certain embodiments, a therapeutically effective amount is an amount sufficient for treating a disease.

A "prophylactically effective amount" of a composition (e.g., a polymer) described herein is an amount sufficient to prevent a condition, or one or more signs or symptoms associated with the condition, or prevent its recurrence. A prophylactically effective amount of a composition means an amount of a composition (e.g., a polymer), alone or in combination with other compositions (e.g., polymers), which provides a prophylactic benefit in the prevention of the condition. The term "prophylactically effective amount" can encompass an amount that improves overall prophylaxis or enhances the prophylactic efficacy of another prophylactic agent. In certain embodiments, a prophylactically effective amount is an amount sufficient for delivering an agent in preventing and/or treating a disease (e.g., a proliferative disease (e.g., cancer)).

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., *Stedman's Medical Dictionary*, 25th ed.; Hensyl ed.; Williams & Wilkins: Philadelphia, 1990. Exemplary cancers include, but are not limited to, hematological malignancies. Additional exemplary cancers include, but are not limited to, lung cancer (e.g., bronchogenic carcinoma, small cell lung cancer (SCLC), non-small cell lung cancer (NSCLC), adenocarcinoma of the lung); kidney cancer (e.g., nephroblastoma, a.k.a. Wilms' tumor, renal cell carcinoma); acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer; inflammatory myofibroblastic tumors; immunocytic amyloidosis; liver cancer (e.g., hepatocellular cancer (HCC), malignant hepatoma); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

An "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or noninfectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid, arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme arthritis, Guillain-Barré syndrome, Hashimoto's thyroiditis, and cardiomyopathy.

The term "autoinflammatory disease" refers to a category of diseases that are similar but different from autoimmune diseases. Autoinflammatory and autoimmune diseases share common characteristics in that both groups of disorders result from the immune system attacking a subject's own tissues and result in increased inflammation. In autoinflammatory diseases, a subject's innate immune system causes inflammation for unknown reasons. The innate immune system reacts even though it has never encountered autoantibodies or antigens in the subject. Autoinflammatory disorders are characterized by intense episodes of inflammation that result in such symptoms as fever, rash, or joint swelling. These diseases also carry the risk of amyloidosis, a potentially fatal buildup of a blood protein in vital organs. Autoinflammatory diseases include, but are not limited to, familial Mediterranean fever (FMF), neonatal onset multisystem inflammatory disease (NOMID), tumor necrosis factor (TNF) receptor-associated periodic syndrome (TRAPS), deficiency of the interleukin-1 receptor antagonist (DIRA), and Behcet's disease.

The terms "nucleic acid," "nucleic acid sequence," "nucleic acid molecule," and "polynucleotide" are used interchangeably, refer to a series of nucleotide bases (also called "nucleotides") in DNA and RNA, and mean any chain of two or more nucleotides. The polynucleotides can be chimeric mixtures or derivatives or modified versions thereof, single-stranded or double-stranded. The oligonucleotide can be modified at the base moiety, sugar moiety, or phosphate backbone, for example, to improve stability of the molecule, its hybridization parameters, etc. The antisense oligonuculeotide may comprise a modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil, a thio-guanine, and 2,6-diaminopurine. A nucleotide sequence typically carries genetic information, including the information used by cellular machinery to make proteins and enzymes. These terms include double-or single-stranded genomic and cDNA, RNA, any synthetic and genetically manipulated polynucleotide, and both sense and antisense polynucleotides. This includes single- and double-stranded molecules, i.e., DNA-DNA, DNA-RNA and RNA-RNA hybrids, as well as "protein nucleic acids" (PNAs) formed by conjugating bases to an amino acid backbone. This also includes nucleic acids containing carbohydrate or lipids. Exemplary DNAs include single-stranded DNA (ssDNA), double-stranded DNA (dsDNA), plasmid DNA (pDNA), genomic DNA (gDNA), complementary DNA (cDNA), antisense DNA, chloroplast DNA (ctDNA or cpDNA), microsatellite DNA, mitochondrial DNA (mtDNA or mDNA), kinetoplast DNA (kDNA), provirus, lysogen, repetitive DNA, satellite DNA, and viral DNA. Exemplary RNAs include single-stranded RNA (ssRNA), double-stranded RNA (dsRNA), small interfering RNA (siRNA), messenger RNA (mRNA), precursor messenger RNA (pre-mRNA), small hairpin RNA or short hairpin RNA (shRNA), microRNA (miRNA), guide RNA (gRNA), transfer RNA (tRNA), antisense RNA (asRNA), heterogeneous nuclear RNA (hnRNA), coding RNA, non-coding RNA (ncRNA), long non-coding RNA (long ncRNA or lncRNA), satellite RNA, viral satellite RNA, signal recognition particle RNA, small cytoplasmic RNA, small nuclear RNA (snRNA), ribosomal RNA (rRNA), Piwi-interacting RNA (piRNA), polyinosinic acid, ribozyme, flexizyme, small nucleolar RNA (snoRNA), spliced leader RNA, viral RNA, and viral satellite RNA.

Polynucleotides described herein may be synthesized by standard methods known in the art, e.g., by use of an automated DNA synthesizer (such as those that are commercially available from Biosearch, Applied Biosystems, etc.). As examples, phosphorothioate oligonucleotides may be synthesized by the method of Stein et al., *Nucl. Acids Res.*, 16, 3209, (1988), methylphosphonate oligonucleotides can be prepared by use of controlled pore glass polymer supports (Sarin et al., *Proc. Natl. Acad. Sci. U.S.A.* 85, 7448-7451, (1988)). A number of methods have been developed for delivering antisense DNA or RNA to cells, e.g., antisense molecules can be injected directly into the tissue site, or modified antisense molecules, designed to target the desired cells (antisense linked to peptides or antibodies that specifically bind receptors or antigens expressed on the target cell surface) can be administered systemically. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines. However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong promoter. The use of such a construct to transfect target cells in the subject will result in the transcription of sufficient amounts of single stranded RNAs that will form complementary base pairs with the endogenous target gene transcripts and thereby prevent translation of the target gene mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human, cells. Such promoters can be inducible or constitutive. Such promoters include, but are not limited to: the SV40 early promoter region (Bernoist et al., *Nature,* 290, 304-310, (1981); Yamamoto et al., *Cell,* 22, 787-797, (1980); Wagner et al., *Proc. Natl. Acad. Sci. U.S.A.* 78, 1441-1445, (1981); Brinster et al., *Nature* 296, 39-42, (1982)). Any type of plasmid, cosmid, yeast artificial chromosome, or viral vector can be used to prepare the recombinant DNA construct that can be introduced directly into the tissue site. Alternatively, viral vectors can be used which selectively infect the desired tissue, in which case administration may be accomplished by another route (e.g., systemically).

The polynucleotides may be flanked by natural regulatory (expression control) sequences or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications, such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, isotopes (e.g., radioactive isotopes), biotin, and the like.

The term "mRNA" or "mRNA molecule" refers to messenger RNA, or the RNA that serves as a template for protein synthesis in a cell. The sequence of a strand of mRNA is based on the sequence of a complementary strand of DNA comprising a sequence coding for the protein to be synthesized.

A "protein," "peptide," or "polypeptide" comprises a polymer of amino acid residues linked together by peptide bonds. The term refers to proteins, polypeptides, and peptides of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these.

The term "therapeutic agent" refers to any substance having therapeutic properties that produce a desired, usually beneficial, effect. For example, therapeutic agents may treat, ameliorate, and/or prevent disease. Therapeutic agents, as disclosed herein, may be biologics or small molecule therapeutics.

The term "prophylactic agent" refers to any substance having prophylactic properties that produces a desired, usually beneficial, effect in improving overall prophylaxis (preventing a condition and/or disease, one or more symptoms associated with the condition and/or prevent its recurrence), or enhancing the prophylactic efficacy of another prophylactic agent. Prophylactic agents, as disclosed herein, may be biologics or small molecules.

The term "cosmetic agent" refers to any substance having properties used to apply to the subject for cleansing, beautifying, promoting attractiveness, or altering the appearance of the subject. Exemplary cosmetic agents include, but are not limited to, hair products (e.g., shampoo, conditioner), creams, lotions, thickeners, moisturizers (e.g., hyaluronic acid), and personal care products (e.g., anti-acne products (e.g., salicylic acid).

The term "diagnostic agent" or "imaging agent" refers to any substance used for diagnosis of a condition and/or disease in a subject or identifying a condition in a biological sample (e.g., tissue, cell), which does not affect the physiological function of the subject and/or biological sample (e.g., tissue, cell). Exemplary diagnostic agents include, but are not limited to, X-ray contrast agents, organ function diagnosis agents, radioactive diagnostic agents (e.g., diagnostic radiopharmaceutical agents), and fluorescent probes (e.g., fluorophore), radionuclide imaging agents (e.g., agents for gamma scintigraphy, positron emission tomography (PET)). optical imaging agents (e.g., fluorophores).

The term "nutraceutical agent" refers to any substance that is a food or a part thereof, and/or conferring extra health benefits in addition to the basic nutritional value found in foods. For example, nutraceutical agents may contain components from food sources. Exemplary nutraceutical agents include, but are not limited to, antioxidants, dietary supplements, fortified dairy products, and citrus fruits, and vitamins, minerals, herbals, milk, and cereals.

The term "polymer" refers to a compound comprising three or more, four or more, five or more, six or more, seven or more, eight or more, nine or more, ten or more, or eleven or more covalently connected repeating units. In certain embodiments, a polymer is synthetic (i.e., not naturally occurring). In certain embodiments, a polymer can be a linear, branched, cross-linked, star, brush, or brush-arm star polymer. In certain embodiments, a polymer can form gels (e.g., hydrogels). Polymers comprise macromolecules, and have molecular weights ranging from thousands of grams/mole to millions of grams/mole.

The term "gel" is a nonfluid colloidal network or nonfluid polymer network that is expanded throughout its whole volume by a fluid (e.g., a solvent, such as water). A gel has a finite, usually rather small, yield stress. A gel may contain: (i) a covalent molecular network (e.g., polymer network), e.g., a network formed by crosslinking molecules (e.g., polymers) or by nonlinear polymerization; (ii) a molecular network (e.g., polymer network) formed through non-covalent aggregation of molecules (e.g., polymers), caused by complexation (e.g., coordination bond formation), electrostatic interactions, hydrophobic interactions, hydrogen bonding, van der Waals interactions, π-π stacking stacking, or a combination thereof, that results in regions of local order acting as the network junction points. The term "hydrogel" refers to a gel, in which the fluid is water. Hydrogels include a hydrophilic structure (e.g., three-dimensional structure), comprising cross=linked polymer networks that can hold a large amount of water. In certain embodiments, a hydrogel can be a colloidal gel. In certain embodiments, a hydrogel can be a homopolymeric hydrogel, which is a polymer network derived from a single species of monomer, a basic structural unit comprising of any polymer network. In certain embodiments, a hydrogel can be a copolymeric hydrogel that is comprised of two or more different monomer species with at least one hydrophilic component. In certain embodiments, a hydrogel can be a Multipolymer Interpenetrating polymeric hydrogel (IPN), which comprises two independent cross-linked synthetic and/or natural polymer components, within a network form.

The term "particle" refers to a small object, fragment, or piece of a substance that may be a single element, inorganic material, organic material, or mixture thereof. Examples of particles include polymeric particles, single-emulsion particles, double-emulsion particles, coacervates, liposomes, microparticles, nanoparticles, macroscopic particles, pellets, crystals, aggregates, composites, pulverized, milled or otherwise disrupted matrices, and cross-linked protein or polysaccharide particles, each of which have an average characteristic dimension of about less than about 1 mm and at least 1 nm, where the characteristic dimension, or "critical dimension," of the particle is the smallest cross-sectional dimension of the particle. A particle may be composed of a single substance or multiple substances. In certain embodiments, the particle is not a viral particle. In other embodiments, the particle is not a liposome. In certain embodiments, the particle is not a micelle. In certain embodiments, the particle is substantially solid throughout. In certain embodiments, the particle is a nanoparticle. In certain embodiments, the particle is a microparticle. In certain embodiments, the particle comprises a polymer and/or composition thereof described herein.

The term "nanoparticle" refers to a particle having an average (e.g., mean) dimension (e.g., diameter) of between about 1 nanometer (nm) and about 1 micrometer (μm) (e.g., between about 1 nm and about 300 nm, between about 1 nm and about 100 nm, between about 1 nm and about 30 nm, between about 1 nm and about 10 nm, or between about 1 nm and about 3 nm), inclusive. In certain embodiments, the nanoparticle comprises a polymer and/or composition thereof described herein.

The disclosure is not intended to be limited in any manner by the above exemplary listing of substituents. Additional terms may be defined in other sections of this disclosure.

BRIEF DESCRIPTION OF THE DRAWINGS

FIG. 6A is an $^1$H NMR spectrum of PEG tetra-alkynoates derived from a PEG of 5000 g/mol. FIG. 6B is an $^1$H NMR spectrum of PEG tetra-alkynoates derived from a PEG of 10000 g/mol. FIG. 6C is an $^1$H NMR spectrum of PEG tetra-alkynoates derived from a PEG of 20000 g/mol.

FIG. 7A is an infrared spectrum of a PEG tetra-alkynoate derived from PEG of 5000 g/mol. FIG. 7B is an infrared spectrum of a PEG tetra-alkynoate derived from a PEG of 10000 g/mol. FIG. 7C is an infrared spectrum of PEG tetra-alkynoates derived from a PEG of 20000 g/mol.

FIG. 9A shows the hydrogels with entrapped THP-1 cells. FIG. 9B shows the hydrogels with entrapped NIH/3T3 cells.

FIG. 10A shows THP-1 cells. FIG. 10B shows NIH/3T3 cells.

DETAILED DESCRIPTION OF CERTAIN EMBODIMENTS OF THE INVENTION

Figure 1A:
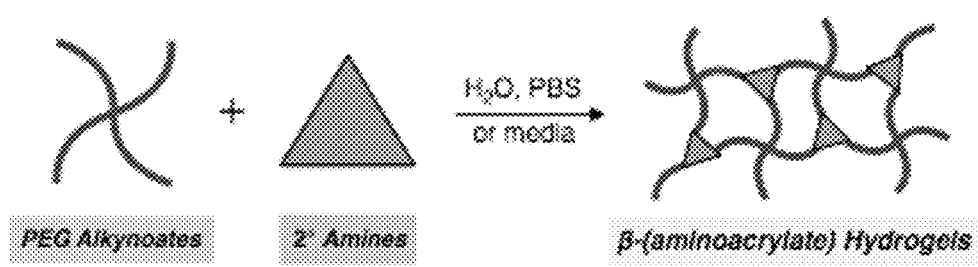
FIG. 1A is a schematic showing that easy to access and operationally simple to formulate β-aminoacrylate hydrogels can be formed in water, PBS, or media, without the need for initiators, catalysts, or specialized equipment.

Provided herein are polymers of Formula (I), and pharmaceutically acceptable salts, co-crystals, tautomers, stereoisomers, and isotopically labeled derivatives thereof, compositions, kits, and methods of using the polymers described herein (e.g., methods of using polymers described herein for delivering agents (e.g., for therapeutic, diagnostic, prophylactic, ophthalmic, intraoperative, or cosmetic use) to a subject, cell, tissue, or biological sample. The polymers described herein are also used as part of a material (e.g., biodegradable materials, biocompatible materials, wound dressing (e.g., bandages)), drug depots, coatings, or as scaffolds for tissue engineering. Also described herein are methods of preparing the polymers described herein. The polymers may be useful in coatings (e.g., surface coatings), bulking agents, sealants, additives (e.g., food additives, pharmaceutical additives, product additives), diagnostics, barrier materials, separators of biomolecules and/or cells, biosensors, agricultural applications, and/or hygienic products (e.g., towels, tissue papers, diapers). The polymers are non-toxic, biodegradable, water-compatible, commercially scalable (e.g., to a multi-gram scale) from commercially available materials, and operationally simple to formulate, where gel formation occurs upon simple mixing of precursor solutions without any need for catalysts, initiators, nor specialized equipment.

In one aspect, disclosed are polymers of Formula (I):

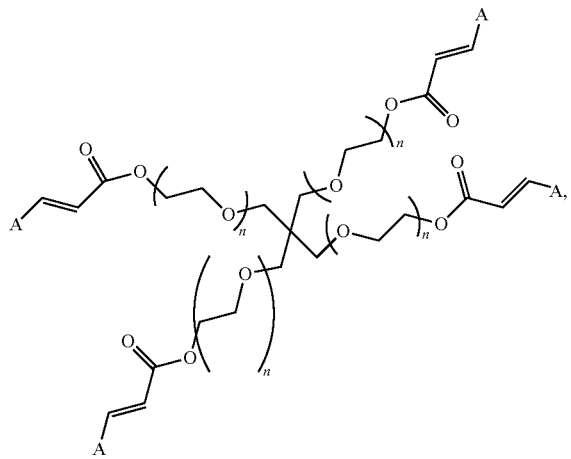

and pharmaceutically acceptable salts, co-crystals, tautomers, stereoisomers, and isotopically labeled derivatives thereof,
wherein:
  each A independently is an amine; and
  each n independently is between 10-150.

In one aspect, disclosed are polymers of Formula (I):

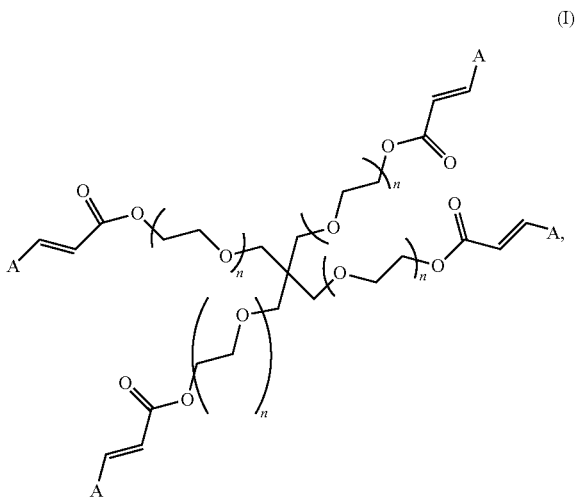

and pharmaceutically acceptable salts thereof. In one aspect, disclosed are polymers ("gels" or "hydrogels") formed by the cross-linking of polymers of Formula (I). In certain embodiments, at least about 50%, at least about 60%, at least about 70%, at least about 80%, or at least about 90% of all instances of Formula (I) included in a gel described herein are interstructurally cross-linked. In certain embodiments, at least about 40%, at least about 50%, at least about 60%, at least about 70%, at least about 80%, of all instances of Formula (I) included in a gel described herein are interstructurally cross-linked. In certain embodiments, at least about 50%, at least about 60%, at least about 70%, at least about 80%, or at least about 90% of all instances of Formula (I) included in a gel described herein are intrastructurally cross-linked. In certain embodiments, at least about 40%, at least about 50%, at least about 60%, at least about 70%, at least about 80%, of all instances of Formula (I) included in a gel described herein are intrastructurally cross-linked. In certain embodiments, at least about 50%, at least about 60%, at least about 70%, at least about 80%, or at least about 90% of all instances of Formula (I) included in a gel described herein have stoichiometric cross-linking. In certain embodiments, at least about 50%, at least about 60%, at least about 70%, at least about 80%, or at least about 90%, or at least about 90-100% of all instances of Formula (I) included in a gel described herein have stoichiometric cross-linking. In certain embodiments, at least about 90-100% of all instances of Formula (I) included in a gel described herein have stoichiometric cross-linking.

The structure of a gel (hydrogel) described herein includes the primary structure (e.g., the structure of the primary moieties of the gel) (e.g., polymers of Formula (I)) and secondary structure (e.g., the way how different instances of the primary moieties are connected to one another (e.g., interstructurally or intrastructurally).

Formula (I) includes one or more instances of substituent A. Formula (I) includes four or more instances of substituent A. In certain embodiments, at least one instance of A is a primary, secondary, or tertiary amine. In certain embodiments, at least one instance of A is a terminal "end-cap" amine. In certain embodiments, Formula (I) includes approximately 25-65%, approximately 30-60%, approximately 30-50%, approximately 30-45%, or approximately 25-40% end-cap amines. In certain embodiments, at least one instance of A is a straight-chain amine or branched amine. In certain embodiments, at least one instance of A is a straight-chain amine. In certain embodiments, at least one instance of A is a linear amine. In certain embodiments, at least one instance of A is a branched amine. In certain embodiments, at least one instance of A is an alkylamine. In certain embodiments, the amine is selected from the group consisting of dodecyl amine, 3-amino-1,2-propanediol, 5-amino-pentanol, N,N-dimethylethylenediamine, 2-morpholinoethylamine, and 2,2'-((oxybis(ethane-2,1-diyl))bis(oxy))diethanamine.

In certain embodiments, at least one instance of A is a primary amine (e.g., —NH$_2$). In certain embodiments, at least one instance of A is —NH$_2$. In certain embodiments, at least one instance of A is a secondary amine (e.g., —NH (optionally substituted alkyl)). In certain embodiments, at least one instance of A is of formula —NH(R$^{a2}$), wherein R$^{a2}$ is optionally substituted alkyl, optionally substituted alkenyl, or optionally substituted alkynyl. In certain embodiments, at least one instance of A is a tertiary amine. In certain embodiments, at least one instance of A is of formula —N(R$^{a2}$)$_2$, wherein each instance of R$^{a2}$ is independently optionally substituted alkyl, optionally substituted alkenyl, or optionally substituted alkynyl. In certain embodiments, at least one instance of A is a cyclic amine. A "cyclic amine" refers to a cyclic heterocyclic group containing one or more nitrogen atoms as part of the cyclic ring. In certain embodiments, at least one instance of A is aziridine. In certain embodiments, at least one instance of A is azetidine, pyrrolidine, pipiridine, piperazine, morpholine, or thiomorpholine. In certain embodiments, at least one instance of A is piperidine. In certain embodiments, at least one instance of A is of the formula:

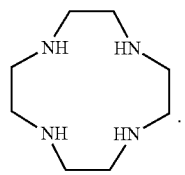 [SMILES: C1CNCCNCCNCCN1]

In certain embodiments, at least one instance of A is a matrix metalloproteinase (MMP) degradable amine. A "matrix metalloproteinase (MMP) degradable amine" refers to an amine degradable by the enzyme matrix metalloproteinase (MMP) (e.g., MMP-1, MMP-2). In certain embodiments, at least one instance of A is a MMP-1 degradable amine. In certain embodiments, at least one instance of A is a MMP-2 degradable amine. In certain embodiments, at least one instance of A is a redox sensitive amine. A "redox sensitive amine" refers to an amine sensitive to or activated by "redox" (reduction and/or oxidation reactions), or an amine capable of being reduced and/or oxidized. A "photocleavable amine" refers to an amine that may be cleaved or degraded by light, in the presence and/or absence of a catalyst (e.g., a photoactive catalyst). In certain embodiments, at least one instance of A is a photocleavable amine.

In certain embodiments, at least one instance of A is of the formula

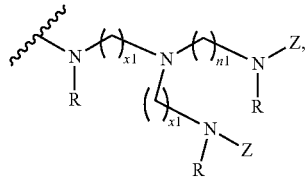

wherein each R independently is hydrogen, optionally substituted alkyl, optionally substituted alkenyl, or optionally substituted alkynyl; each Z independently is hydrogen, optionally substituted alkyl, optionally substituted alkenyl, optionally substituted alkynyl, or of the Formula (I-Z):

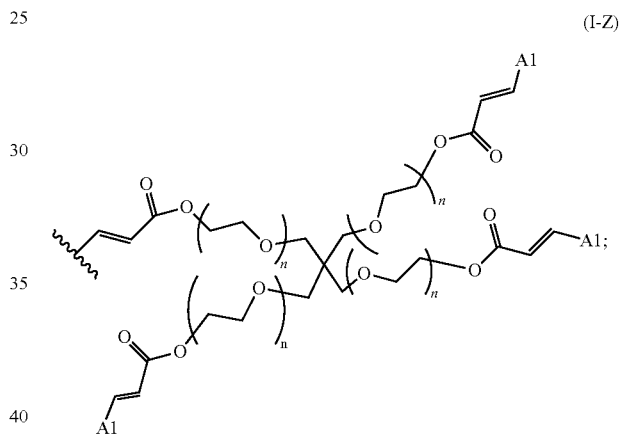

(I-Z)

each A1 independently is an amine; each x1 is independently 2, 3, 4, or 5; and each n independently is 15-140. In certain embodiments, at least one instance of A is of the Formula

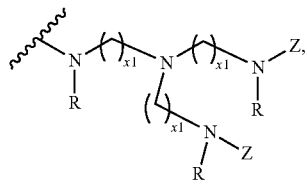

and at least one instance of x1 is 2 or 3. In certain embodiments, at least one instance of x1 is 2. In certain embodiments, at least one instance of x1 is 3. In certain embodiments, at least one instance of x1 is 4. In certain embodiments, at least one instance of x1 is 5. In certain embodiments, at least one instance of A is of the Formula (I-A):

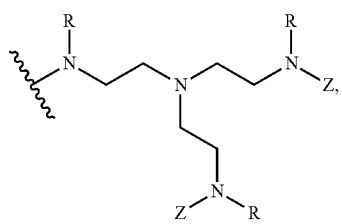

wherein R and Z are as described below. In certain embodiments, at least one instance of A is of the Formula (I-A):

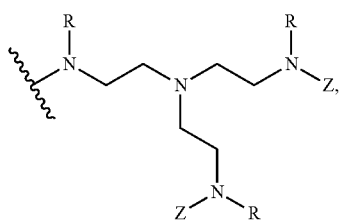

wherein each R independently is hydrogen, optionally substituted alkyl, optionally substituted alkenyl, or optionally substituted alkynyl, or nitrogen protecting group; each Z independently is hydrogen, optionally substituted alkyl, optionally substituted alkenyl, optionally substituted alkynyl, or of the Formula (I-Z):

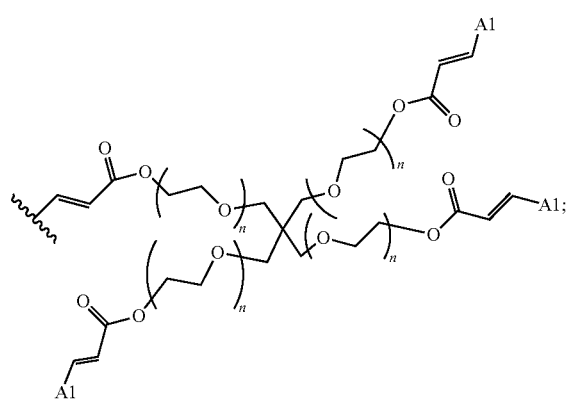

each A1 independently is an amine; and each n independently is between 10-150. In certain embodiments, at least one instance of A is of the Formula (I-A):

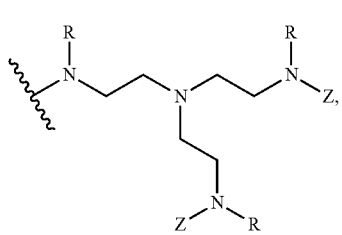

wherein each R independently is hydrogen, optionally substituted alkyl, optionally substituted alkenyl, or optionally substituted alkynyl, or nitrogen protecting group; each Z independently is hydrogen, optionally substituted alkyl, optionally substituted alkenyl, optionally substituted alkynyl, or of the Formula (I-Z):

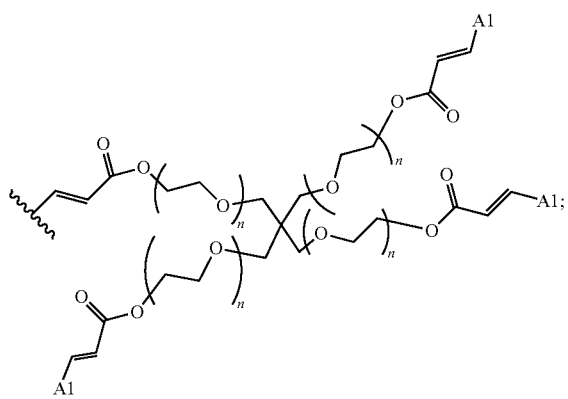

each A1 independently is an amine; and each n independently is between 10-150.

In certain embodiments, at least one instance of A is of the Formula (I-A):

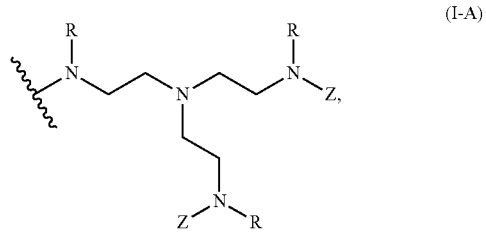

wherein each R independently is hydrogen or optionally substituted alkyl; and each Z independently is hydrogen or optionally substituted alkyl.

In certain embodiments, at least one instance of A is of the Formula (I-A):

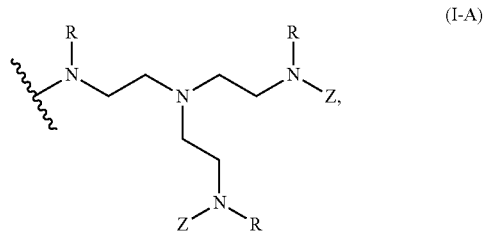

wherein each R independently is hydrogen or of the Formula (I-Z):

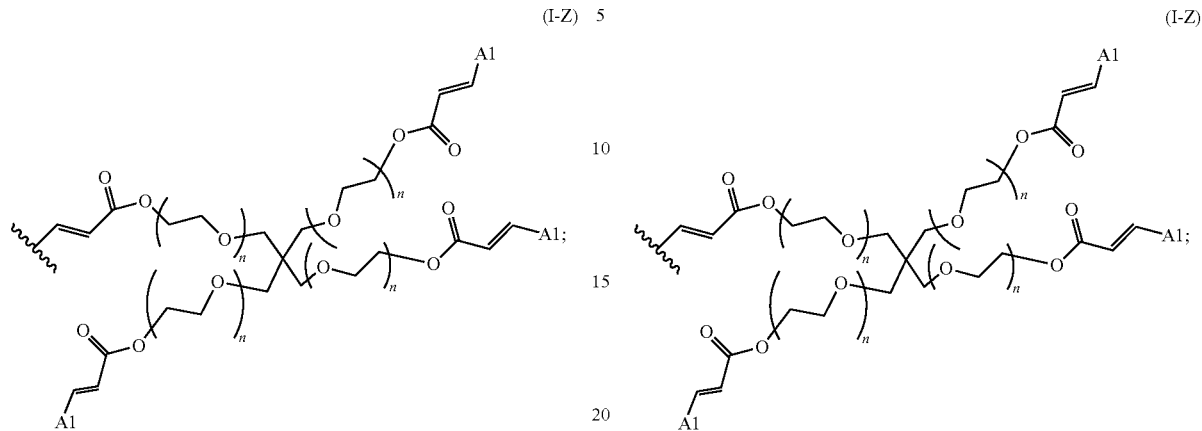

(I-Z)

each Z independently is hydrogen or optionally substituted alkyl; and each A1 independently is an amine of Formula (I-B)

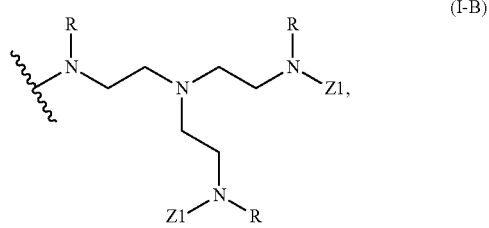

(I-B)

wherein each instance of R is optionally substituted $C_{1-6}$ alkyl; each Z1 independently is hydrogen, optionally substituted alkyl, optionally substituted alkenyl, or optionally substituted alkynyl; and at least one instance of Z1 is hydrogen.

In certain embodiments, approximately 25-65%, approximately 30-60%, approximately 30-50%, approximately 30-45%, approximately 40-50%, or approximately 25-40% of the instances of A are of Formula (I-A):

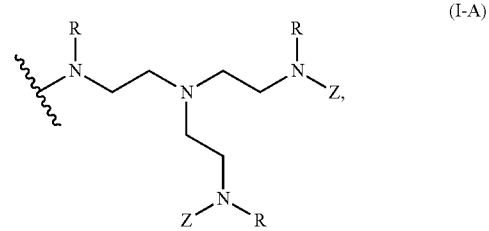

(I-A)

wherein each R independently is hydrogen or of the Formula (I-Z):

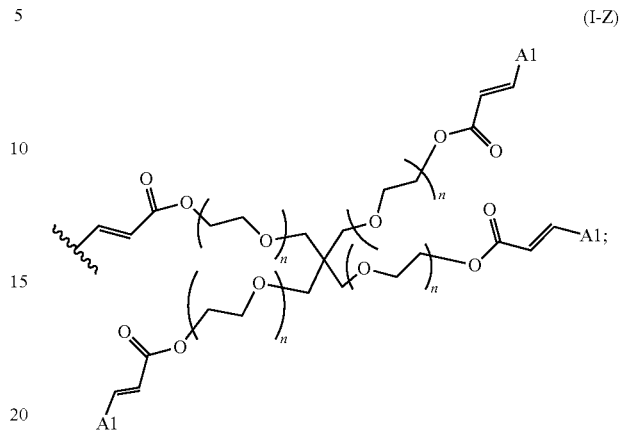

(I-Z)

each Z independently is hydrogen or optionally substituted alkyl; and each A1 independently is an amine described herein (e.g., of Formula (I-B)). In certain embodiments, approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, or approximately 80-90%, of the instances of A are of the formula:

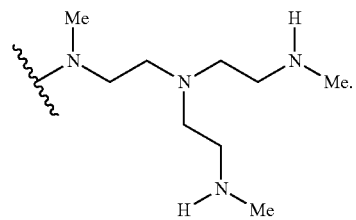 [SMILES: *N(C)CCN(CCNC)CCNC]

In certain embodiments, at least one instance of A is of the formula:

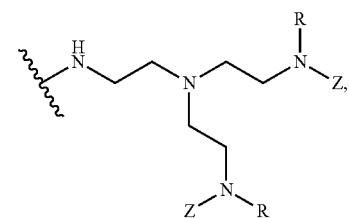

wherein each R independently is hydrogen, optionally substituted alkyl, optionally substituted alkenyl, or optionally substituted alkynyl; each Z independently is hydrogen, optionally substituted alkyl, optionally substituted alkenyl, optionally substituted alkynyl, or of the Formula (I-Z):

(I-Z)

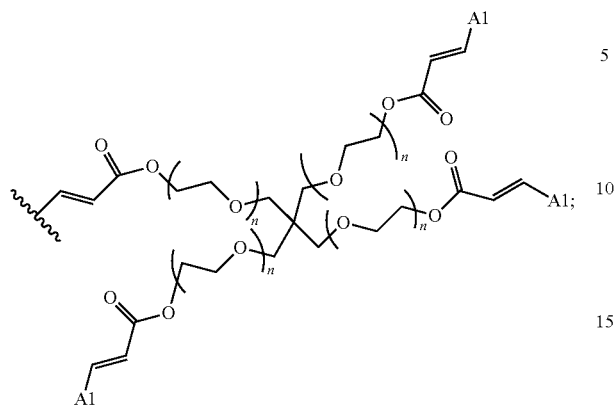

each A1 independently is an amine; and each n independently is between 10-150. In certain embodiments, at least one instance of A is of the formula:

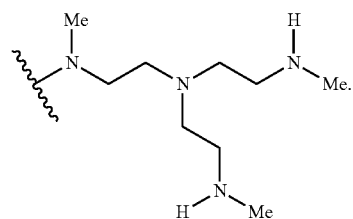

In certain embodiments, at least one instance of A is of the formula:

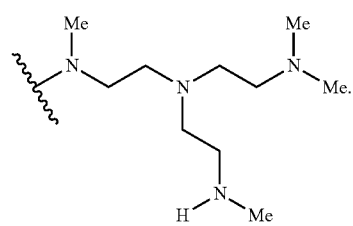

In certain embodiments, at least one instance of A is of the formula:

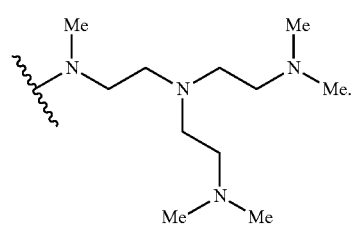

In certain embodiments, at least one instance of A is of the formula:

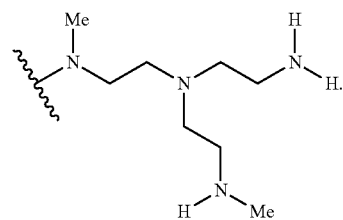

In certain embodiments, at least one instance of A is of the formula:

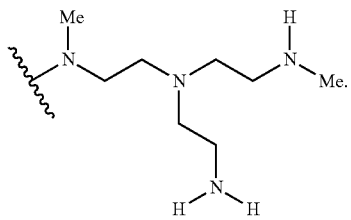 [SMILES: *N(C)CCN(CCN)CCNC]

In certain embodiments, at least one instance of A is of the formula:

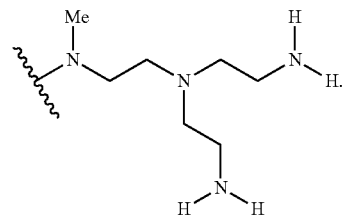

In certain embodiments, at least one instance of A is of the formula:

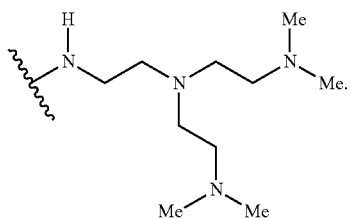 [SMILES: *NCCN(CCN(C)C)CCN(C)C]

In certain embodiments, approximately 25-65%, approximately 30-60%, approximately 30-50%, approximately 30-45%, approximately 40-50%, or approximately 25-40% of the instances of A are of the formula:

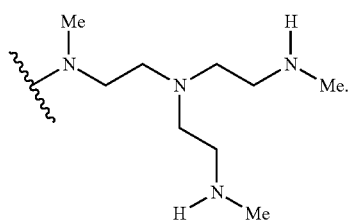 [SMILES: *N(C)CCN(CCNC)CCNC]

In certain embodiments, approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, or approximately 80-90%, of the instances of A are of the formula:

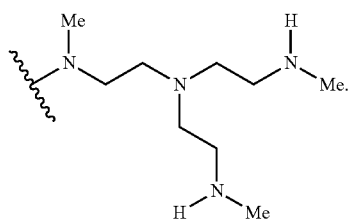 [SMILES: *N(C)CCN(CCNC)CCNC]

In certain embodiments, all instances of A are of the formula:

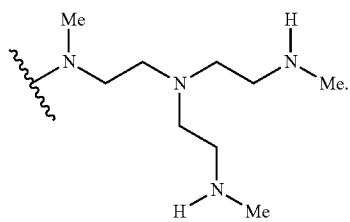 [SMILES: *N(C)CCN(CCNC)CCNC]

In certain embodiments, Formula (I) includes four or more instances of substituent A1. In certain embodiments, Formula (I) includes four or more instances of A; A is of Formula (I-A); Z is of Formula (I-Z):

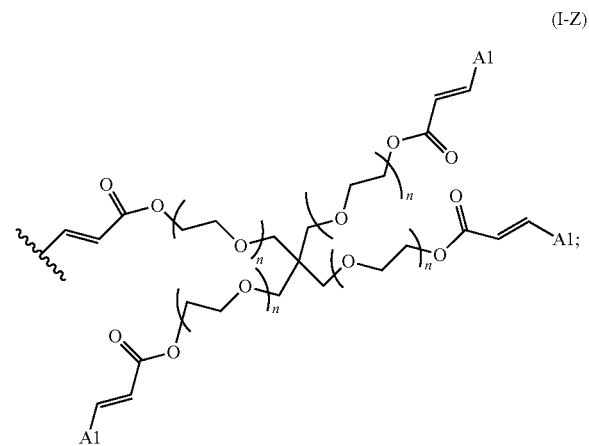

(I-Z)

and Formula (I) includes 24 or more instances of substituent A1. In certain embodiments, Formula (I-Z) includes 3 or more instances of substituent A1. In certain embodiments, Formula (I-Z) includes 4 or more instances of substituent A1. In certain embodiments, Formula (I-Z) includes 5 or more instances of substituent A1. In certain embodiments, Formula (I-Z) includes 6 or more instances of substituent A1. In certain embodiments, Formula (I-Z) includes 7 or more instances, 8 or more instances, 9 or more instances, 10 or more instances, 11 or more instances, 12 or more instances, 13 or more instances, 14 or more instances, 15 or more instances, 16 or more instances, 17 or more instances, 18 or more instances, 19 or more instances, 20 or more instances, 21 or more instances, 22 or more instances, 23 or more instances, or 24 or more instances, of substituent A1.

In certain embodiments, Formula (I-Z) includes three or more instances of substituent A1. In certain embodiments, in Formula (I-Z), at least one instance of A1 is a primary, secondary, or tertiary amine. In certain embodiments, in Formula (I-Z), at least one instance of A1 is a terminal "end-cap" amine. In certain embodiments, Formula (I-Z) includes approximately 25-65%, approximately 30-60%, approximately 30-50%, approximately 30-45%, or approximately 25-40% end-cap amines. In certain embodiments, in Formula (I-Z), at least one instance of A1 is a straight-chain amine or branched amine. In certain embodiments, in Formula (I-Z), at least one instance of A1 is a straight-chain amine. In certain embodiments, in Formula (I-Z), at least one instance of A1 is a linear amine. In certain embodiments, in Formula (I-Z), at least one instance of A1 is a branched amine. In certain embodiments, in Formula (I-Z), at least one instance of A1 is an alkylamine. In certain embodiments, in Formula (I-Z), the amine of A1 is selected from the group consisting of dodecyl amine, 3-amino-1,2-propanediol, 5-amino-pentanol, N,N-dimethylethylenediamine, 2-morpholinoethylamine, and 2,2'-((oxybis(ethane-2,1-diyl))bis(oxy))diethanamine.

In certain embodiments, in Formula (I-Z), at least one instance of A1 is a primary amine (e.g., $-NH_2$). In certain embodiments, in Formula (I-Z), at least one instance of A1 is $-NH_2$. In certain embodiments, in Formula (I-Z), at least one instance of A1 is a secondary amine (e.g., $-NH$ (optionally substituted alkyl)). In certain embodiments, in Formula (I-Z), at least one instance of A1 is of formula $-NH(R^{a2})$, wherein $R^{a2}$ is optionally substituted alkyl, optionally substituted alkenyl, or optionally substituted alkynyl. In certain embodiments, in Formula (I-Z), at least one instance of A1 is a tertiary amine. In certain embodiments, in Formula (I-Z), at least one instance of A1 is of formula $-N(R^{a2})_2$, wherein each instance of $R^{a2}$ is independently optionally substituted alkyl, optionally substituted alkenyl, or optionally substituted alkynyl. In certain embodiments, in Formula (I-Z), at least one instance of A1 is a cyclic amine. In certain embodiments, at least one instance of A1 is aziridine. In certain embodiments, at least one instance of A1 is azetidine, pyrrolidine, pipiridine, piperazine, morpholine, or thiomorpholine. In certain embodiments, at least one instance of A is piperidine. In certain embodiments, at least one instance of A is of the formula:

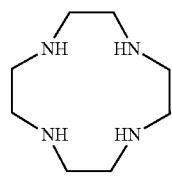

In certain embodiments, in Formula (I-Z), at least one instance of A1 is of the Formula (I-B):

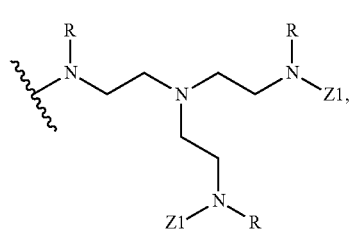

(I-B)

wherein each instance of R is optionally substituted $C_{1-6}$ alkyl or nitrogen protecting group; each Z1 independently is hydrogen, optionally substituted alkyl, optionally substituted alkenyl, or optionally substituted alkynyl; and at least one instance of Z1 is hydrogen. In certain embodiments, in Formula (I-Z), at least one instance of A1 is of the Formula (I-B):

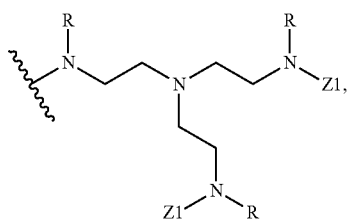

(I-B)

wherein each instance of R is optionally substituted $C_{1-6}$ alkyl; each Z1 independently is hydrogen, optionally substituted alkyl, optionally substituted alkenyl, or optionally substituted alkynyl; and at least one instance of Z1 is hydrogen. In certain embodiments, in Formula (I-Z), at least one instance of A1 is of the Formula (I-B):

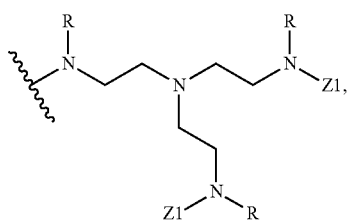

(I-B)

wherein each Z1 independently is hydrogen, optionally substituted alkyl, optionally substituted alkenyl, or optionally substituted alkynyl; and at least one instance of Z1 is hydrogen.

In certain embodiments, in Formula (I-Z), at least one instance of A1 is of the Formula (I-B):

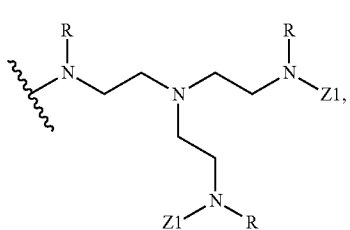

(I-B)

wherein each instance of R is optionally substituted $C_{1-6}$ alkyl; each Z1 independently is hydrogen or optionally substituted alkyl; and at least one instance of Z1 is hydrogen.

In certain embodiments, approximately 25-65%, approximately 30-60%, approximately 30-50%, approximately 30-45%, approximately 40-50%, or approximately 25-40% of the instances of A1 are of Formula (I-B):

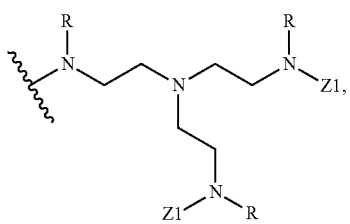

(I-B)

wherein each instance of R is optionally substituted $C_{1-6}$ alkyl; each Z1 independently is hydrogen or optionally substituted alkyl; and at least one instance of Z1 is hydrogen. In certain embodiments, approximately 25-65%, approximately 30-60%, approximately 30-50%, approximately 30-45%, approximately 40-50%, approximately 25-40%, or approximately 50-60%, approximately 60-70%, approximately 70-80%, approximately 80-90%, approximately 90-95%, or approximately 90-100%, of the instances of A1 are of Formula (I-B):

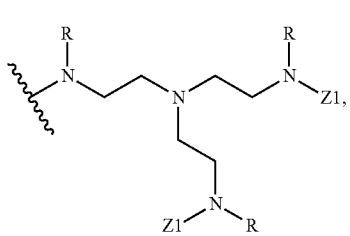

(I-B)

wherein each instance of R is optionally substituted $C_{1-6}$ alkyl; each Z1 independently is hydrogen or optionally substituted alkyl; and at least one instance of Z1 is hydrogen. In certain embodiments, approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, or approximately 80-90%, of the instances of A1 are of the formula:

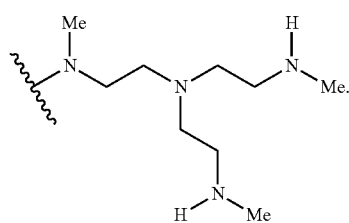 [SMILES: *N(C)CCN(CCNC)CCNC]

In certain embodiments, approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, approximately 70-80%, approximately 80-90%, approximately 90-95%, or approximately 90-100%, of the instances of A1 are of the formula:

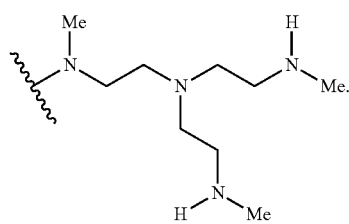 [SMILES: *N(C)CCN(CCNC)CCNC]

In certain embodiments, at least one instance of A1 is of the formula:

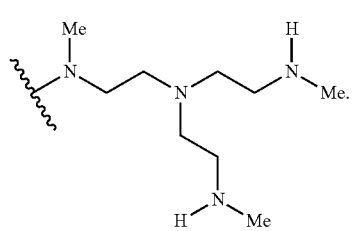 [SMILES: *N(C)CCN(CCNC)CCNC]

In certain embodiments, at least one instance of A1 is of the formula:

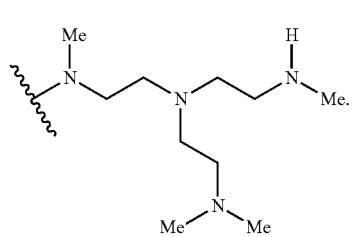 [SMILES: *N(C)CCN(CCNC)CCN(C)C]

In certain embodiments, at least one instance of A1 is of the formula:

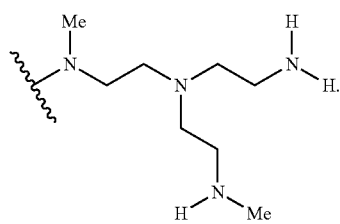

In certain embodiments, at least one instance of A1 is of the formula:

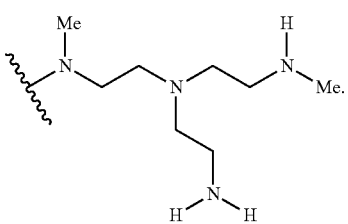 [SMILES: *N(C)CCN(CCN)CCNC]

In certain embodiments, at least one instance of A1 is of the formula:

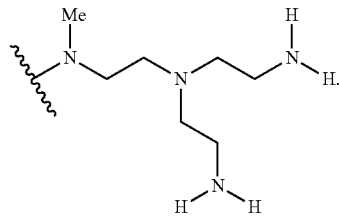

In certain embodiments, approximately 25-65%, approximately 30-60%, approximately 30-50%, approximately 30-45%, approximately 40-50%, or approximately 25-40% of the instances A1 are of the formula:

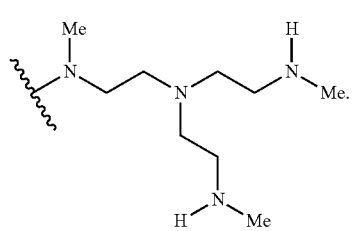 [SMILES: *N(C)CCN(CCNC)CCNC]

In certain embodiments, approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, or approximately 80-90%, of the instances of A1 are of the formula:

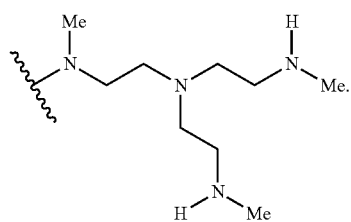

In certain embodiments, all instances of A1 are of the formula:

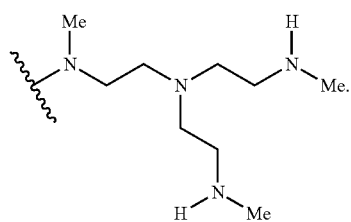

Formulae (I-A), (I-B), and (B) each include one or more instances of substituent R. In certain embodiments, at least one instance of R in Formulae (I-A) or (I-B) is hydrogen (H). In certain embodiments, in Formulae (I-A) or (I-B), approximately 25-65%, approximately 30-60%, approximately 30-50%, approximately 30-45%, approximately 40-50%, or approximately 25-40%, of the instances of R are hydrogen. In certain embodiments, in Formulae (I-A) or (I-B), approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, or approximately 80-90%, of the instances of R are hydrogen. In certain embodiments, in Formulae (I-A) or (I-B), no instances of R are hydrogen and approximately 90-100% of the instances of R are methyl. In certain embodiments, in Formulae (I-A) or (I-B), no instances of R are hydrogen and approximately 80-90% or approximately 90-100% of the instances of R are methyl. In certain embodiments, in Formulae (I-A) or (B), no instances of R are hydrogen and approximately 90-100% of the instances of R are methyl. In certain embodiments, in Formulae (I-A) or (I-B), no instances of R are hydrogen and approximately 80-90% or approximately 90-100% of the instances of R are methyl. In certain embodiments, in Formulae (I-A) or (B), no instances of R are hydrogen and approximately 90-100% of the instances of R are methyl. In certain embodiments, in Formulae (I-A) or (I-B), no instances of R are hydrogen and approximately 80-90% or approximately 90-100% of the instances of R are methyl.

In certain embodiments, in Formulae (I-A) or (I-B), approximately 25-65%, approximately 30-60%, approximately 30-50%, approximately 30-45%, approximately 40-50%, or approximately 25-40%, of the instances of R are optionally substituted alkyl. In certain embodiments, in Formulae (I-A) or (I-B), approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, or approximately 80-90%, of the instances of R are optionally substituted alkyl. In certain embodiments, in Formulae (I-A) or (I-B), approximately 25-65%, approximately 30-60%, approximately 30-50%, approximately 30-45%, approximately 40-50%, or approximately 25-40%, of the instances of R are unsubstituted alkyl. In certain embodiments, in Formulae (I-A) or (I-B), approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, or approximately 80-90%, of the instances of R are unsubstituted alkyl. In certain embodiments, in Formulae (I-A) or (I-B), approximately 25-65%, approximately 30-60%, approximately 30-50%, approximately 30-45%, approximately 40-50%, or approximately 25-40%, of the instances of R are unsubstituted $C_{1-6}$ alkyl. In certain embodiments, in Formulae (I-A) or (I-B), approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, or approximately 80-90%, of the instances of R are unsubstituted $C_{1-6}$ alkyl. In certain embodiments, in Formulae (I-A) or (I-B), approximately 25-65%, approximately 30-60%, approximately 30-50%, approximately 30-45%, approximately 40-50%, or approximately 25-40%, of the instances of R are methyl. In certain embodiments, in Formulae (I-A) or (I-B), approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, or approximately 80-90%, of the instances of R are methyl. In certain embodiments, in Formulae (I-A), approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, approximately 80-90%, or approximately 90-100%, of the instances of R are methyl.

In certain embodiments, at least one instance of R in Formulae (I-A) or (I-B) is hydrogen. In certain embodiments, in Formulae (I-A) or (I-B), approximately 25-65%, approximately 30-60%, approximately 30-50%, approximately 30-45%, approximately 40-50%, or approximately 25-40%, of the instances of R are hydrogen. In certain embodiments, in Formulae (I-A) or (I-B), approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, or approximately 80-90%, of the instances of R are hydrogen. In certain embodiments, in Formulae (I-A) or (I-B), at least one instance of R is optionally substituted alkyl (e.g., substituted or unsubstituted $C_{1-6}$ alkyl). In certain embodiments, in Formulae (I-A) or (I-B), at least one instance of R is optionally substituted $C_{1-6}$ alkyl. In certain embodiments, in Formulae (I-A) or (I-B), at least one instance of R is optionally substituted methyl. In certain embodiments, in Formulae (I-A) or (A I-B at least one instance of R is unsubstituted methyl. In certain embodiments, in Formulae (I-A) or (I-B), approximately 25-65%, approximately 30-60%, approximately 30-50%, approximately 30-45%, approximately 40-50%, or approximately 25-40%, of the instances of R are methyl. In certain embodiments, in Formulae (I-A) or (I-B), approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, or approximately 80-90%, of the instances of R are methyl. In certain embodiments, in Formulae (I-A) or (A I-B at least one instance of R is optionally substituted ethyl. In certain embodiments, in Formulae (I-A) or (I-B), at least one instance of R is unsubstituted ethyl. In certain embodiments, in Formulae (I-A) or (I-B), at least one instance of R is optionally substituted methyl, optionally substituted ethyl, optionally substituted n-propyl, unsubstituted isopropyl, optionally substituted n-butyl, optionally substituted t-butyl, or optionally substituted n-pentyl. In certain embodiments, in Formulae (I-A) or (I-B), at least one instance of R is unsubstituted methyl, unsubstituted ethyl, unsubstituted n-propyl, unsubstituted isopropyl, unsubstituted n-butyl, unsubstituted t-butyl, or unsubstituted n-pentyl. In certain embodiments, in Formulae (I-A) or (I-B), at least one instance of R is optionally substituted alkenyl (e.g., substituted or unsubstituted $C_{2-6}$ alkenyl). In certain embodiments, in Formulae (I-A) or (I-B), at least one instance of R is optionally substituted alkynyl (e.g., substituted or unsubstituted $C_{2-6}$ alkynyl). In certain embodiments, in Formulae (I-A) or (I-B), all instances of R are hydrogen. In certain embodiments, in Formulae (I-A) or (I-B), all instances of R are optionally substituted $C_{1-6}$ alkyl. In certain embodiments, in Formulae (I-A) or (I-B), all instances of R are unsubstituted $C_{1-6}$ alkyl. In certain embodiments, in Formulae (I-A) or (I-B), all instances of R are unsubstituted methyl. In certain embodiments, in Formulae (I-A) or (I-B), one instance of R is hydrogen and the remaining instances of R are optionally substituted alkyl. In certain embodiments, in Formulae (I-A) or (I-B), one instance of R is hydrogen and the remaining instances of R are optionally substituted $C_{1-6}$ alkyl. In certain embodiments, in Formulae (I-A) or (I-B), one instance of R is hydrogen and the remaining instances of R are unsubstituted $C_{1-6}$ alkyl. In certain embodiments, in Formulae (I-A) or (I-B), one instance of R is hydrogen and the remaining instances of R are unsubstituted methyl.

In certain embodiments, in Formulae (I-A) or (I-B), at least one instance of R is optionally substituted ethyl. In certain embodiments, in Formulae (I-A) or (I-B), at least one instance of R is unsubstituted ethyl. In certain embodiments, in Formulae (I-A) or (I-B), at least one instance of R is optionally substituted methyl, optionally substituted ethyl, optionally substituted n-propyl, unsubstituted isopropyl, optionally substituted n-butyl, optionally substituted t-butyl, or optionally substituted n-pentyl. In certain embodiments, in Formulae (I-A) or (I-B), at least one instance of R is unsubstituted methyl, unsubstituted ethyl, unsubstituted n-propyl, unsubstituted isopropyl, unsubstituted n-butyl, unsubstituted t-butyl, or unsubstituted n-pentyl. In certain embodiments, in Formula (I), at least one instance of R is optionally substituted alkenyl (e.g., substituted or unsubstituted $C_{2-6}$ alkenyl). In certain embodiments, in Formulae (I-A) or (I-B), at least one instance of R is optionally substituted alkynyl (e.g., substituted or unsubstituted $C_{2-6}$ alkynyl).

Formulae (I-A) and (B) each include one or more instances of substituent Z. In certain embodiments, at least one instance of Z in Formulae (I-A) or (B) is hydrogen (H). In certain embodiments, at least one instance of Z in Formula (I-A) is hydrogen. In certain embodiments, in Formulae (I-A) or (B), approximately 25-65%, approximately 30-60%, approximately 30-50%, approximately 30-45%, approximately 40-50%, or approximately 25-40%, of the instances of Z are hydrogen. In certain embodiments, in Formulae (I-A) or (B), approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, approximately 80-90%, or approximately 90-100%, of the instances of Z are hydrogen. In certain embodiments, in Formulae (I-A) or (B), approximately 25-65%, approximately 30-60%, approximately 30-50%, approximately 30-45%, approximately 40-50%, or approximately 25-40%, of the instances of Z are optionally substituted alkyl. In certain embodiments, in Formulae (I-A) or (B), approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, or approximately 80-90%, of the instances of Z are optionally substituted alkyl. In certain embodiments, in Formulae (I-A) or (B), approximately 25-65%, approximately 30-60%, approximately 30-50%, approximately 30-45%, approximately 40-50%, or approximately 25-40%, of the instances of Z are unsubstituted alkyl. In certain embodiments, in Formulae (I-A) or (B), approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, or approximately 80-90%, of the instances of Z are unsubstituted alkyl. In certain embodiments, in Formulae (I) or (B), approximately 25-65%, approximately 30-60%, approximately 30-50%, approximately 30-45%, approximately 40-50%, or approximately 25-40%, of the instances of Z are unsubstituted $C_{1-6}$ alkyl. In certain embodiments, in Formulae (I-A) or (B), approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, or approximately 80-90%, of the instances of Z are unsubstituted $C_{1-6}$ alkyl. In certain embodiments, in Formulae (I-A) or (B), approximately 25-65%, approximately 30-60%, approximately 30-50%, approximately 30-45%, approximately 40-50%, or approximately 25-40%, of the instances of Z are methyl. In certain embodiments, in Formulae (I-A) or (B), approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, or approximately 80-90%, of the instances of Z are methyl.

In certain embodiments, in Formula (I-A), approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, approximately 80-90%, or approximately 90-100%, of the instances of Z are hydrogen; and approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, approximately 80-90%, or approximately 90-100%, of the instances of Z are methyl.

In certain embodiments, in Formula (I-A), approximately 70-90%, approximately 80-90%, or approximately 90-100%, of the instances of Z are hydrogen; and approximately 60-90%, approximately 70-90%, approximately 80-90%, or approximately 90-100%, of the instances of R are methyl. In certain embodiments, in Formula (B), approximately 70-90%, approximately 80-90%, or approximately 90-100%, of the instances of Z1 are hydrogen; and approximately 60-90%, approximately 70-90%, approximately 80-90%, or approximately 90-100%, of the instances of R are methyl.

In certain embodiments, in Formula (I-A), approximately 70-90%, approximately 80-90%, or approximately 90-100%, of the instances of Z are hydrogen; and approximately 60-90%, approximately 70-90%, approximately 80-90%, or approximately 90-100%, of the instances of R are ethyl. In certain embodiments, in Formula (B), approximately 70-90%, approximately 80-90%, or approximately 90-100%, of the instances of Z1 are hydrogen; and approximately 60-90%, approximately 70-90%, approximately 80-90%, or approximately 90-100%, of the instances of R are ethyl.

In certain embodiments, at least one instance of Z in Formula (I-A) is hydrogen. In certain embodiments, in Formula (I-A), approximately 25-65%, approximately 30-60%, approximately 30-50%, approximately 30-45%, approximately 40-50%, or approximately 25-40%, of the instances of Z are hydrogen. In certain embodiments, in Formula (I-A), approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, or approximately 80-90%, of the instances of Z are hydrogen. In certain embodiments, at least one instance of Z is optionally substituted alkyl (e.g., substituted or unsubstituted $C_{1-6}$ alkyl). In certain embodiments, at least one instance of Z is optionally substituted $C_{1-6}$ alkyl. In certain embodiments, at least one instance of R is optionally substituted methyl. In certain embodiments, at least one instance of Z is unsubstituted methyl. In certain embodiments, in Formula (I-A), approximately 25-65%, approximately 30-60%, approximately 30-50%, approximately 30-45%, approximately 40-50%, or approximately 25-40%, of the instances of Z are methyl. In certain embodiments, in Formula (I-A), approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, or approximately 80-90%, of the instances of Z are methyl.

In certain embodiments, in Formula (I), all instances of Z are hydrogen. In certain embodiments, in Formula (I), all instances of Z are optionally substituted $C_{1-6}$ alkyl. In certain embodiments, in Formula (I), all instances of Z are unsubstituted $C_{1-6}$ alkyl. In certain embodiments, in Formula (I), all instances of Z are unsubstituted methyl. In certain embodiments, in Formula (I), one instance of Z is hydrogen and the remaining instances of Z are optionally substituted alkyl. In certain embodiments, in Formula (I), one instance of Z is hydrogen and the remaining instances of Z are optionally substituted $C_{1-6}$ alkyl. In certain embodiments, in Formula (I), one instance of Z is hydrogen and the remaining instances of Z are unsubstituted $C_{1-6}$ alkyl. In certain embodiments, in Formula (I), one instance of Z is hydrogen and the remaining instances of Z are unsubstituted methyl.

In certain embodiments, in Formula (I-A), at least one instance of Z is optionally substituted ethyl. In certain embodiments, in Formula (I-A), at least one instance of Z is unsubstituted ethyl. In certain embodiments, in Formula (I-A), at least one instance of Z is optionally substituted methyl, optionally substituted ethyl, optionally substituted n-propyl, unsubstituted isopropyl, optionally substituted n-butyl, optionally substituted t-butyl, or optionally substituted n-pentyl. In certain embodiments, in Formula (I-A), at least one instance of Z is unsubstituted methyl, unsubstituted ethyl, unsubstituted n-propyl, unsubstituted isopropyl, unsubstituted n-butyl, unsubstituted t-butyl, or unsubstituted n-pentyl. In certain embodiments, in Formula (I-A), at least one instance of Z is optionally substituted alkenyl (e.g., substituted or unsubstituted $C_{2-6}$ alkenyl). In certain embodiments, in Formula (I-A), at least one instance of Z is optionally substituted alkynyl (e.g., substituted or unsubstituted $C_{2-6}$ alkynyl).

In certain embodiments, in Formulae (I) or (B), at least one instance of Z is optionally substituted alkyl (e.g., optionally substituted $C_{1-6}$ alkyl). In certain embodiments, in Formulae (I) or (B), at least one instance of Z is optionally substituted $C_{1-6}$ alkyl. In certain embodiments, in Formulae (I) or (B), at least one instance of Z is optionally substituted methyl. In certain embodiments, in Formulae (I) or (B), at least one instance of Z is unsubstituted methyl. In certain embodiments, in Formulae (I) or (B), at least one instance of Z is optionally substituted ethyl. In certain embodiments, in Formulae (I) or (B), at least one instance of Z is optionally substituted methyl, optionally substituted ethyl, optionally substituted n-propyl, unsubstituted isopropyl, optionally substituted n-butyl, optionally substituted t-butyl, or optionally substituted n-pentyl. In certain embodiments, in Formulae (I) or (B), at least one instance of Z is unsubstituted methyl, unsubstituted ethyl, unsubstituted n-propyl, unsubstituted isopropyl, unsubstituted n-butyl, unsubstituted t-butyl, or unsubstituted n-pentyl. In certain embodiments, in Formulae (I) or (B), at least one instance of Z is optionally substituted alkenyl (e.g., substituted or unsubstituted $C_{2-6}$ alkenyl). In certain embodiments, in Formulae (I) or (B), at least one instance of Z is optionally substituted alkynyl (e.g., substituted or unsubstituted $C_{2-6}$ alkynyl).

In certain embodiments, in Formulae (I-A) or (B), at least one instance of R is optionally substituted alkyl; and at least one instance of Z is hydrogen, attached to the same nitrogen. In certain embodiments, in Formulae (I-A) or (B), approximately 25-65%, approximately 30-60%, approximately 30-50%, approximately 30-45%, approximately 40-50%, or approximately 25-40%, of the instances of R are optionally substituted alkyl; and approximately 25-65%, approximately 30-60%, approximately 30-50%, approximately 30-45%, approximately 40-50%, or approximately 25-40%, of the instances of Z are hydrogen, where R and Z are attached to the same nitrogen. In certain embodiments, in Formulae (I-A) or (B), approximately 25-65%, approximately 30-60%, approximately 30-50%, approximately 30-45%, approximately 40-50%, or approximately 25-40%, of the instances of R are optionally substituted alkyl; and approximately 25-65%, approximately 30-60%, approximately 30-50%, approximately 30-45%, approximately 40-50%, approximately 25-40%, approximately 50-90%, approximately 60-90%, approximately 70-90%, approximately 80-90%, or approximately 90-100%, of the instances of Z are hydrogen, where R and Z are attached to the same nitrogen.

In certain embodiments, in Formulae (I-A) or (B), approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, or approximately 80-90%, of the instances of R are optionally substituted alkyl; and approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, or approximately 80-90%, of the instances of Z are hydrogen, where R and Z are attached to the same nitrogen. In certain embodiments, in Formulae (I-A) or (B), at least one instance of R is optionally substituted $C_{1-6}$ alkyl; and at least one instance of Z is hydrogen, where R and Z are attached to the same nitrogen. In certain embodiments, in Formulae (I-A) or (B), at least one instance of R is optionally substituted methyl; and at least one instance of Z is hydrogen, where R and Z are attached to the same nitrogen.

In certain embodiments, in Formulae (I-A) or (B), approximately 25-65%, approximately 30-60%, approximately 30-50%, approximately 30-45%, approximately 40-50%, or approximately 25-40%, of the instances of R are optionally substituted $C_{1-6}$ alkyl; in Formulae (I-A) or (B), approximately 25-65%, approximately 30-60%, approximately 30-50%, approximately 30-45%, approximately 40-50%, or approximately 25-40%, of the instances of Z are hydrogen, where R and Z are attached to the same nitrogen. In certain embodiments, in Formulae (I-A) or (B), approximately 25-65%, approximately 30-60%, approximately 30-50%, approximately 30-45%, approximately 40-50%, or approximately 25-40%, of the instances of R are optionally substituted methyl; in Formulae (I-A) or (B), approximately 25-65%, approximately 30-60%, approximately 30-50%, approximately 30-45%, approximately 40-50%, or approximately 25-40%, of the instances of Z are hydrogen, where R and Z are attached to the same nitrogen. In certain embodiments, in Formulae (I-A) or (B), approximately 25-65%, approximately 30-60%, approximately 30-50%, approximately 30-45%, approximately 40-50%, or approximately 25-40%, of the instances of R are unsubstituted methyl; in Formulae (I-A) or (B), approximately 25-65%, approximately 30-60%, approximately 30-50%, approximately 30-45%, approximately 40-50%, or approximately 25-40%, of the instances of Z are hydrogen, where R and Z are attached to the same nitrogen. In certain embodiments, in Formulae (I-A) or (B), approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, or approximately 80-90%, of the instances of R are optionally substituted $C_{1-6}$ alkyl; and approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, or approximately 80-90%, of the instances of Z are hydrogen, where R and Z are attached to the same nitrogen. In certain embodiments, in Formulae (I-A) or (B), approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, or approximately 80-90%, of the instances of R are optionally substituted methyl; and approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, or approximately 80-90%, of the instances of Z are hydrogen, where R and Z are attached to the same nitrogen. In certain embodiments, in Formulae (I-A) or (B), approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, or approximately 80-90%, of the instances of R are unsubstituted methyl; and approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, or approximately 80-90%, of the instances of Z are hydrogen, where R and Z are attached to the same nitrogen.

Formula (I-B) includes one or more instances of Z1. In certain embodiments, in Formula (I-B), at least one instance of Z1 is hydrogen. In certain embodiments, in Formula (I), at least one instance of Z1 is hydrogen.

In certain embodiments, in Formula (I), approximately 25-65%, approximately 30-60%, approximately 30-50%, approximately 30-45%, approximately 40-50%, or approximately 25-40%, of the instances of Z1 are hydrogen. In certain embodiments, in Formula (I), approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, or approximately 80-90%, of the instances of Z1 are hydrogen. In certain embodiments, in Formula (I), approximately 25-65%, approximately 30-60%, approximately 30-50%, approximately 30-45%, approximately 40-50%, or approximately 25-40%, of the instances of Z1 are optionally substituted alkyl. In certain embodiments, in Formula (I), approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, or approximately 80-90%, of the instances of Z1 are optionally substituted alkyl. In certain embodiments, in Formula (I), approximately 25-65%, approximately 30-60%, approximately 30-50%, approximately 30-45%, approximately 40-50%, or approximately 25-40%, of the instances of Z1 are unsubstituted alkyl. In certain embodiments, in Formula (I), approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, or approximately 80-90%, of the instances of Z1 are unsubstituted alkyl. In certain embodiments, in Formula (I), approximately 25-65%, approximately 30-60%, approximately 30-50%, approximately 30-45%, approximately 40-50%, or approximately 25-40%, of the instances of Z1 are unsubstituted $C_{1-6}$ alkyl. In certain embodiments, in Formula (I), approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, or approximately 80-90%, of the instances of Z1 are unsubstituted $C_{1-6}$ alkyl. In certain embodiments, in Formula (I), approximately 25-65%, approximately 30-60%, approximately 30-50%, approximately 30-45%, approximately 40-50%, or approximately 25-40%, of the instances of Z1 are methyl. In certain embodiments, in Formula (I), approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, or approximately 80-90%, of the instances of Z1 are methyl.

In certain embodiments, at least one instance of Z1 in Formula (I-B) is hydrogen. In certain embodiments, in Formula (I-B), approximately 25-65%, approximately 30-60%, approximately 30-50%, approximately 30-45%, approximately 40-50%, or approximately 25-40%, of the instances of Z1 are hydrogen. In certain embodiments, in Formula (I-B), approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, or approximately 80-90%, of the instances of Z1 are hydrogen.

In certain embodiments, at least one instance of Z1 is optionally substituted alkyl (e.g., optionally substituted $C_{1-6}$ alkyl). In certain embodiments, at least one instance of Z1 is optionally substituted $C_{1-6}$ alkyl. In certain embodiments, at least one instance of Z1 is optionally substituted methyl. In certain embodiments, in Formula (I), approximately 25-65%, approximately 30-60%, approximately 30-50%, approximately 30-45%, approximately 40-50%, or approximately 25-40%, of the instances of Z1 are methyl. In certain embodiments, in Formula (I), approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, or approximately 80-90%, of the instances of Z1 are methyl. In certain embodiments, in Formula (I-B), at least one instance of Z1 is unsubstituted methyl. In certain embodiments, in Formula (I), at least one instance of Z1 is unsubstituted methyl. In certain embodiments, in Formula (I), at least one instance of Z1 is optionally substituted ethyl. In certain embodiments, in Formula (I), at least one instance of Z1 is optionally substituted ethyl. In certain embodiments, in Formula (I), at least one instance of Z1 is optionally substituted alkenyl (e.g., substituted or unsubstituted $C_{2-6}$ alkenyl). In certain embodiments, in Formula (I-B), at least one instance of Z1 is optionally substituted alkenyl (e.g., substituted or unsubstituted $C_{2-6}$ alkenyl). In certain embodiments, in Formula (I), at least one instance of Z1 is optionally substituted alkynyl (e.g., substituted or unsubstituted $C_{2-6}$ alkynyl). In certain embodiments, in Formula (I-B), at least one instance of Z1 is optionally substituted alkynyl (e.g., substituted or unsubstituted $C_{2-6}$ alkynyl). In certain embodiments, in Formula (I-B), at least one instance of Z1 is H; and the other instance of Z1 is optionally substituted alkyl (e.g., optionally substituted $C_{1-6}$ alkyl). In certain embodiments, in Formula (I), at least one instance of Z1 is H; and the other instances of Z1 are optionally substituted alkyl (e.g., optionally substituted $C_{1-6}$ alkyl). In certain embodiments, in Formula (I), at least one instance of Z1 is H; and the other instances of Z1are optionally substituted $C_{1-6}$ alkyl. In certain embodiments, in Formula (I-B), at least one instance of Z1 is H; and the other instances of Z1 are optionally substituted $C_{1-6}$ alkyl.

Formulae (I) and (I-Z) each include variable n. In certain embodiments, each n independently is between 5-200. In certain embodiments, each n independently is between 5-200, 100-200, 5-100, 15-100, 10-100, 15-100, or 15-150. In certain embodiments, each n independently is between 5-10, 10-20, 20-30, 30-40, 40-50, 50-60, 25-50, 50-75, 60-70, 70-80, 75-100, 80-90, 90-100, 100-110, 110-120, 120-130, 130-140, 140-150, 100-125, or 125-150. In certain embodiments, each n independently is between 15-140. In certain embodiments, each n independently is between 10-150. In certain embodiments, at least one instance of n is between 15-135. In certain embodiments, at least one instance of n is between 25-140. In certain embodiments, at least one instance of n is between 30-140. In certain embodiments, at least one instance of n is between 35-140. In certain embodiments, at least one instance of n is between 40-140. In certain embodiments, at least one instance of n is between 45-140. In certain embodiments, at least one instance of n is between 50-140. In certain embodiments, at least one instance of n is between 50-135. In certain embodiments, at least one instance of n is between 20-135. In certain embodiments, at least one instance of n is between 25-135. In certain embodiments, at least one instance of n is between 20-140. In certain embodiments, at least one instance of n is between 25-130. In certain embodiments, at least one instance of n is between 30-135. In certain embodiments, each instance of n is between 25-135. In certain embodiments, at least one instance of n is between 20-140. In certain embodiments, at least one instance of n is between 15-140, 15-135, 15-130, 15-125, 15-130, 15-125, 15-120, 15-110, 25-140, 25-135, 25-130, 25-125, 25-130, 25-125, 25-120, 25-110, 30-140, 30-135, 30-130, 30-125, 30-130, 30-125, 30-120, 30-110, 35-140, 35-135, 35-130, 35-125, 35-130, 35-125, 35-120, 35-110, 40-140, 40-135, 40-130, 40-125, 40-130, 40-125, 40-120, 40-110, 45-140, 45-135, 45-130, 45-125, 45-130, 45-125, 45-120, 45-110, 50-140, 50-135, 50-130, 50-125, 50-130, 50-125, 50-120, or 50-110. In certain embodiments, the starting tetra-arm PEG-OH is polydisperse. In certain embodiments, for each arm of the PEG, approximately 10-20%, approximately 20-30%, approximately 30-40%, approximately 40-50%, or approximately 50-60%, of the instances of n are between 15-140, 15-135, 15-130, 15-125, 15-130, 15-125, 15-120, 15-110, 25-140, 25-135, 25-130, 25-125, 25-130, 25-125, 25-120, 25-110, 30-140, 30-135, 30-130, 30-125, 30-130, 30-125, 30-120, 30-110, 35-140, 35-135, 35-130, 35-125, 35-130, 35-125, 35-120, 35-110, 40-140, 40-135, 40-130, 40-125, 40-130, 40-125, 40-120, 40-110, 45-140, 45-135, 45-130, 45-125, 45-130, 45-125, 45-120, 45-110, 50-140, 50-135, 50-130, 50-125, 50-130, 50-125, 50-120, or 50-110. In certain embodiments, for each arm of the PEG, approximately 10-20%, approximately 20-30%, approximately 30-40%, approximately 40-50%, or approximately 50-60%, of the instances of n are between 20-140. In certain embodiments, the starting tetra-arm PEG-OH is monodisperse. In certain embodiments, for each arm of the PEG, approximately 60-90%, approximately 70-90%, approximately 80-90%, or approximately 90-100%, of the instances of n are between 15-140, 15-135, 15-130, 15-125, 15-130, 15-125, 15-120, 15-110, 25-140, 25-135, 25-130, 25-125, 25-130, 25-125, 25-120, 25-110, 30-140, 30-135, 30-130, 30-125, 30-130, 30-125, 30-120, 30-110, 35-140, 35-135, 35-130, 35-125, 35-130, 35-125, 35-120, 35-110, 40-140, 40-135, 40-130, 40-125, 40-130, 40-125, 40-120, 40-110, 45-140, 45-135, 45-130, 45-125, 45-130, 45-125, 45-120, 45-110, 50-140, 50-135, 50-130, 50-125, 50-130, 50-125, 50-120, or 50-110. In certain embodiments, for each arm of the PEG, approximately 60-90%, approximately 70-90%, approximately 80-90%, or approximately 90-100%, of the instances of n are between 20-140. In certain embodiments, for each arm of the PEG, all the instances of n are between 15-140, 15-135, 15-130, 15-125, 15-130, 15-125, 15-120, 15-110, 25-140, 25-135, 25-130, 25-125, 25-130, 25-125, 25-120, 25-110, 30-140, 30-135, 30-130, 30-125, 30-130, 30-125, 30-120, 30-110, 35-140, 35-135, 35-130, 35-125, 35-130, 35-125, 35-120, 35-110, 40-140, 40-135, 40-130, 40-125, 40-130, 40-125, 40-120, 40-110, 45-140, 45-135, 45-130, 45-125, 45-130, 45-125, 45-120, 45-110, 50-140, 50-135, 50-130, 50-125, 50-130, 50-125, 50-120, or 50-110. In certain embodiments, for each arm of the PEG, all the instances of n are between 20-140. In certain embodiments, for each arm of the PEG, all the instances of n are approximately the same. In certain embodiments, for each arm of the PEG, all the instances of n are approximately the same and approximately 80-90%, or approximately 90-100%, of the instances of n are between 20-140. In certain embodiments, in Formulae (I) or (I-Z), approximately 25-65%, approximately 30-60%, approximately 30-50%, approximately 30-45%, approximately 40-50%, or approximately 25-40%, of the instances of n are between 5-200, 100-200, 5-100, 15-100, 10-100, 15-100, or 15-150. In certain embodiments, in Formulae (I) or (I-Z), approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, or approximately 80-90%, of the instances of n are between 5-200, 100-200, 5-100, 15-100, 10-100, 15-100, or 15-150. In certain embodiments, in Formulae (I) or (I-Z), approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, or approximately 80-90%, of the instances of n are between 15-140. In certain embodiments, in Formulae (I) or (I-Z), approximately 25-65%, approximately 30-60%, approximately 30-50%, approximately 30-45%, approximately 40-50%, or approximately 25-40%, of the instances of n are 80-90, 90-100, 100-110, or 110-120. In certain embodiments, in Formulae (I) or (I-Z), approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, or approximately 80-90%, of the instances of n are between 80-90, 90-100, 100-110, or 110-120. In certain embodiments, in Formulae (I) or (I-Z), approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, or approximately 80-90%, of the instances of n are between 15-50, 50-100, or 100-120. In certain embodiments, in Formulae (I) or (I-Z), approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, or approximately 80-90%, of the instances of n are between 15-50. In certain embodiments, in Formulae (I) or (I-Z), approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, or approximately 80-90%, of the instances of n are between 15-75. In certain embodiments, in Formulae (I) or (I-Z), approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, or approximately 80-90%, of the instances of n are between 50-100. In certain embodiments, in Formulae (I) or (I-Z), approximately 25-90%, approximately 25-80%, approximately 25-70%, approximately 25-60%, approximately 25-50%, approximately 25-40%, approximately 25-30%, approximately 50-90%, approximately 60-90%, approximately 70-90%, or approximately 80-90%, of the instances of n are between 100-120.

In certain embodiments, the polymer is of formula:

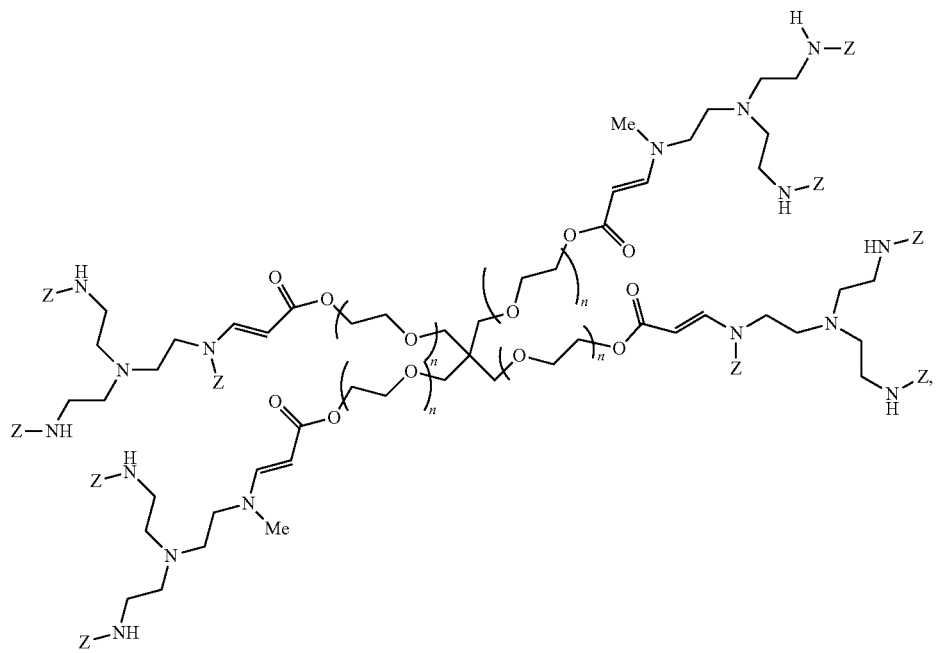

wherein approximately 50-90%, approximately 60-90%, approximately 70-90%, or approximately 80-90%, of the instances R are optionally substituted alkyl; and each instance of n is between 5-10, 10-20, 20-30, 30-40, 40-50, 50-60, 25-50, 50-75, 60-70, 70-80, 75-100, 80-90, 90-100, 100-110, 110-120, 120-130, 130-140, 140-150, 100-125, or 125-150.

In certain embodiments, the polymer is of formula:
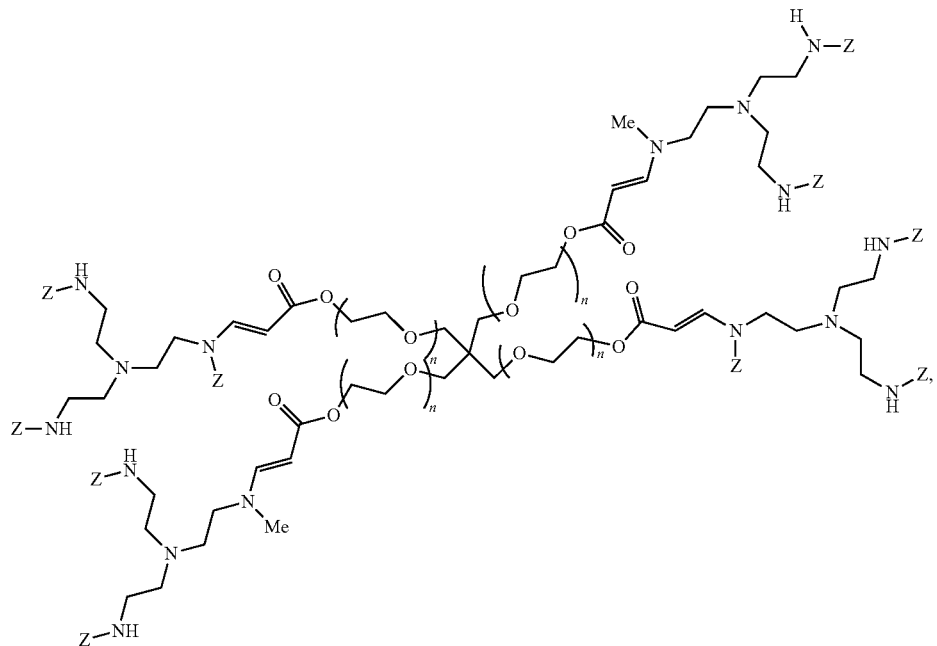
wherein each R independently is optionally substituted alkyl; and each instance of n is between 5-10, 10-20, 20-30, 30-40, 40-50, 50-60, 25-50, 50-75, 60-70, 70-80, 75-100, 80-90, 90-100, 100-110, 110-120, 120-130, 130-140, 140-150, 100-125, or 125-150.
In certain embodiments, the polymer is of formula:
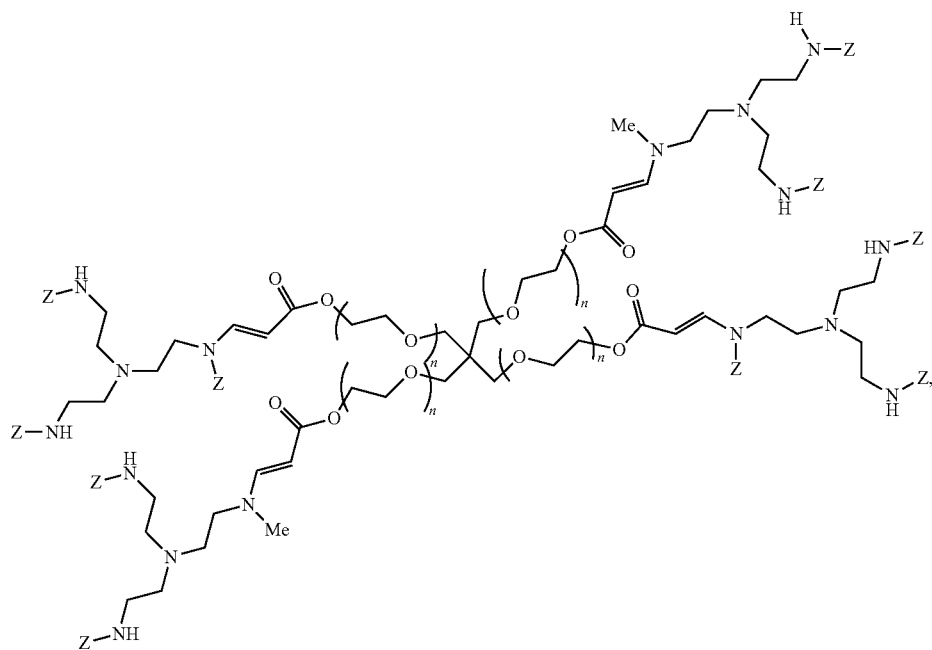

wherein each R independently is optionally substituted alkyl; and each instance of n is between 25-135.
In certain embodiments, the polymer is of formula:
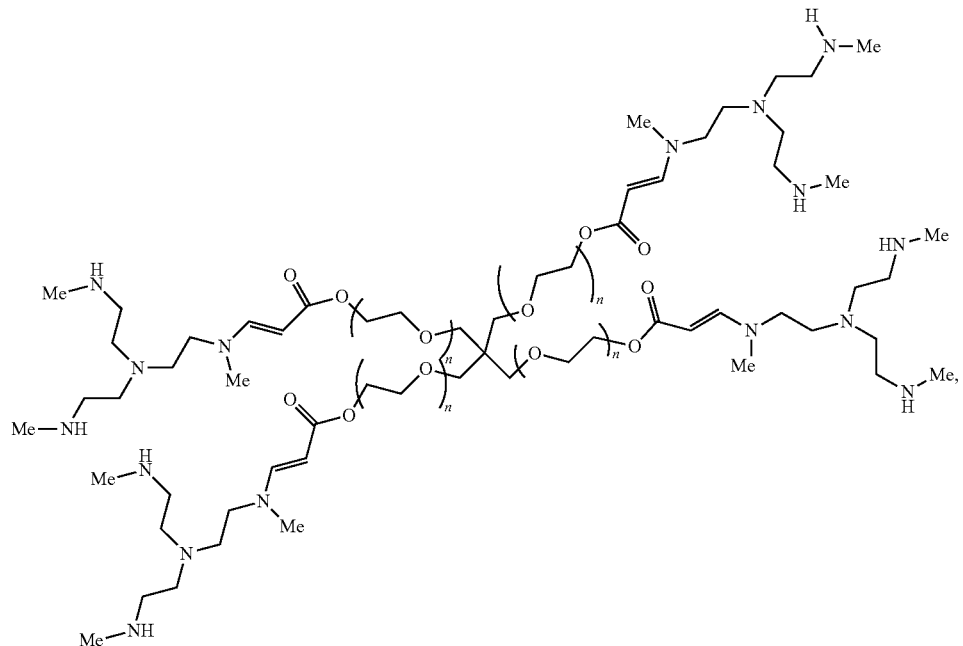
wherein each instance of n is between 25-135.
In certain embodiments, the polymer is of formula:
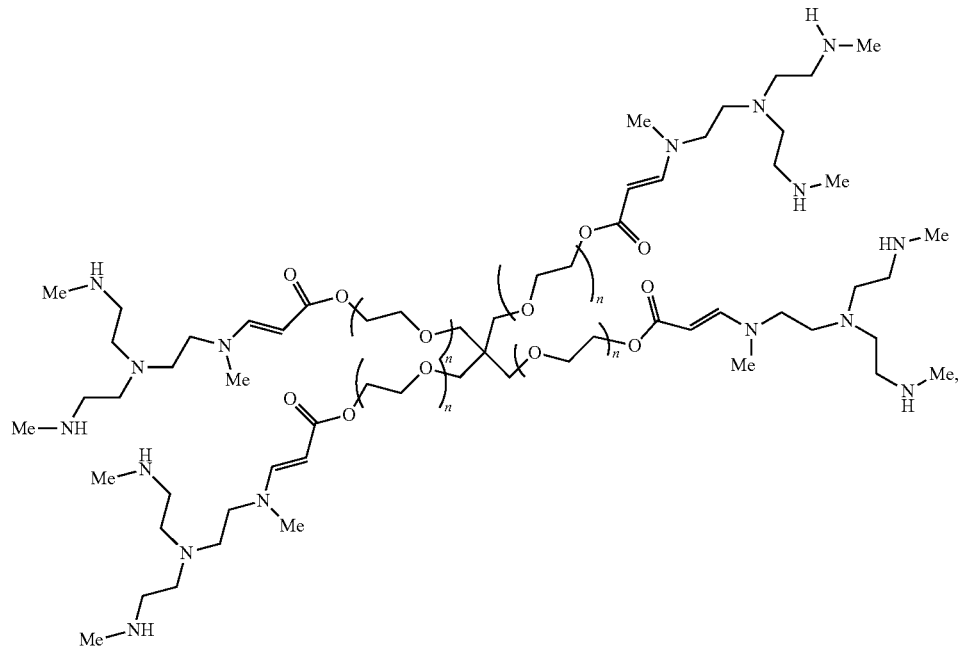
wherein each instance of n is between 25-135, which is further cross-linked.

In certain embodiments, the polymer is of Formula (X):

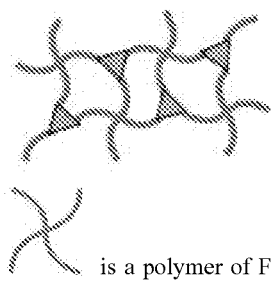, wherein each instance of  is a polymer of Formula (I):

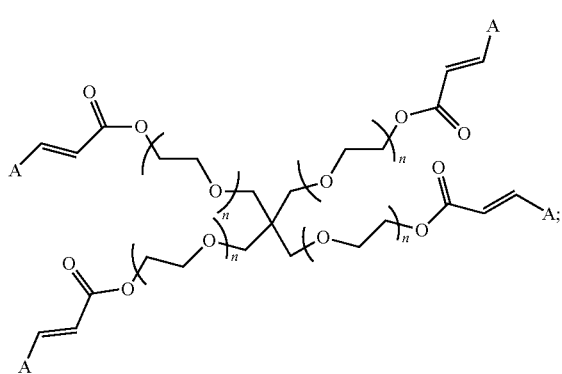

(I)

and each instance of ▲ is an amine A.

In certain embodiments, the polymer is of Formula (X):

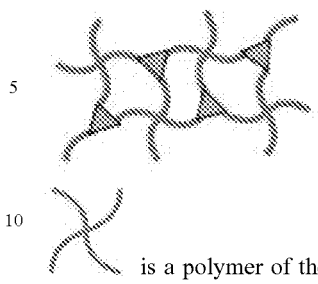, wherein each instance of 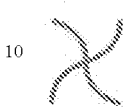 is a polymer of the formula:

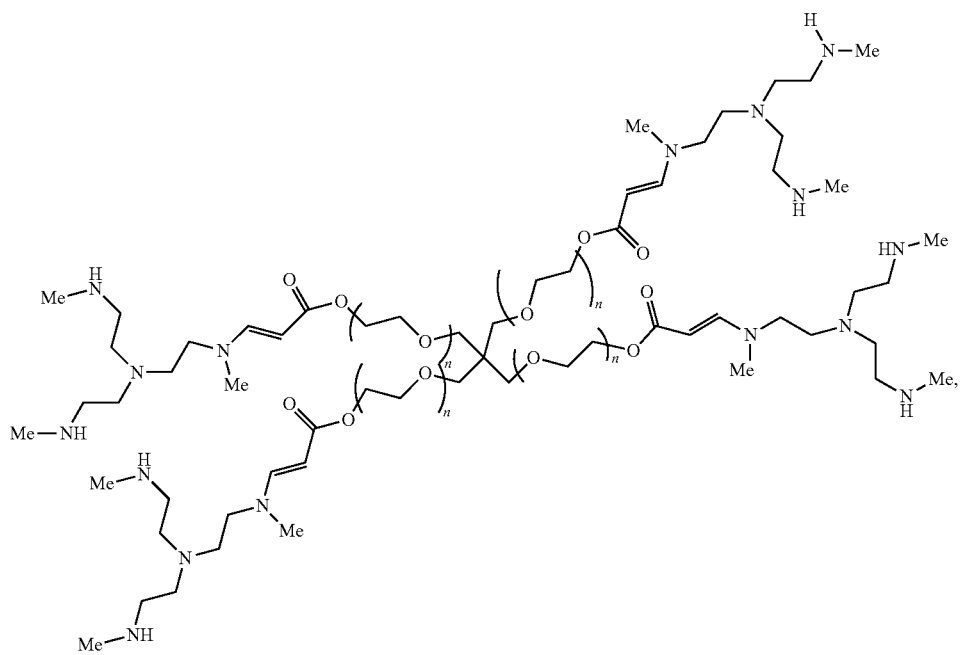

wherein each instance of n is between 25-135; and each instance of ▲ is an amine A.

In certain embodiments, the polymer is biodegradable or biocompatible. In certain embodiments, the polymer is biodegradable. In certain embodiments, the polymer is biocompatible. As used herein, "biodegradable" polymers are those that, when introduced into cells, are broken down by the cellular machinery or by hydrolysis into components that the cells can either reuse or dispose of without significant toxic effect on the cells (i.e., fewer than about 20% of the cells are killed when the components are added to cells in vitro). The components preferably do not induce inflammation or other adverse effects in vivo. In certain embodiments, the chemical reactions relied upon to break down the biodegradable polymers are uncatalyzed. In certain embodiments, the half-life of the biodegradable polymers in a subject is between about 1 month to 6 months. In certain embodiments, the half-life of the biodegradable polymers in a subject is between about 2 months to 6 months. In certain embodiments, the half-life of the biodegradable polymers in a subject is between about 2 months to 6 months, 6 months to 12 months, or 12 months to 18 months. The term "biocompatible," as used herein is intended to describe compounds that are not toxic to cells. Polymers are "biocompatible" if their addition to cells in vitro results in less than or equal to 20% cell death, and their administration in vivo does not induce inflammation or other such adverse effects. In certain embodiments, polymers are biocompatible in a subject tested within an enzymatic (e.g., esterase) live/dead assay, if their addition to cells in vitro results in less than or equal to 20% cell death, and their administration in vivo does not induce inflammation or other such adverse effects.

In certain embodiments, the polymer is a hydrogel. In certain embodiments, the polymer is a hydrogel, which is a gel in which the fluid is water. In certain embodiments, the polymer of Formula (I) forms a β-aminoacrylate hydrogel upon the mixing of the tetra-arm polyethylene glycol alkynoate compound of Formula (A) and an amine of Formula (B) under suitable conditions described below.

In certain embodiments, the polymer of Formula (I) is a polymer provided in any one of the Examples below. In certain embodiments, the polymer of Formula (I) is a polymer provided in Examples 1 or 2 below.

In certain embodiments, the polymer of Formula (I) is a product of the synthesis disclosed in Example 1 or Example 2 by reacting the tetra-arm polyethylene glycol alkynoate compound of Formula (A) and an amine of Formula (B) under suitable conditions described below.

Compositions and Kits

The present disclosure provides compositions comprising a polymer described herein, and an excipient. In certain embodiments, the composition is a pharmaceutical composition comprising a polymer described herein, and an excipient, and a therapeutic agent or pharmaceutical agent. A composition described herein may further comprise a solvent (e.g., a suitable solvent described herein, such as water). The excipient included in a composition described herein may be a pharmaceutically acceptable excipient, cosmetically acceptable excipient, dietarily acceptable excipient, or nutraceutically acceptable excipient. A composition described herein may further comprise a fluid (e.g., a solvent, e.g., water, a biocompatible solvent, or a mixture thereof).

In certain embodiments, the composition is used for delivering one or more agents (e.g., pharmaceutical agents, cosmetic agents, diagnostic agent). In certain embodiments, the composition is used as part of a material (e.g., biodegradable materials, biocompatible materials, wound dressing (e.g., bandages), drug depots, coatings), for or as scaffolds for tissue engineering.

In certain embodiments, a composition described herein is in the form of gels. In certain embodiments, the gels result from self-assembly of the components of the composition. The agent to be delivered by the gel may be in the form of a gas, liquid, or solid. The compositions described herein may be combined with polymers (synthetic or natural), surfactants, cholesterol, carbohydrates, proteins, lipids, lipidoids, etc. to form gels. The gels may be further combined with an excipient to form the composition. The gels are described in more detail herein. The polymers and compositions (e.g., gels) may also be able to absorb a large amount of a fluid (e.g., absorb at least 100 times by weight of the fluid, compared to the weight of the supramolecular complex or the dry weight of the composition (weight of the composition minus the weight of the fluid included in the composition) and, therefore, may be useful as super-absorbent materials.

In certain embodiments, the composition further comprises water. In certain embodiments, the composition further comprises water and comprises a hydrogel. In certain embodiments, the excipient is a pharmaceutically acceptable excipient. In certain embodiments, the composition further comprises an active ingredient.

In certain embodiments, the pharmaceutical composition is a sustained-release formulation, in which a therapeutic agent (e.g., a small molecule, nucleic acid, protein, peptide, polynucleotide, biologic) is slowly released into the body of a subject at a controlled rate of agent release over an extended period of time. In certain embodiments, the pharmaceutical composition is a controlled-release formulation, in which predictably constant plasma concentrations of a therapeutic agent are maintained, via a controlled rate and dose of release of the agent over a specific, extended period of time. In certain embodiments, the controlled-release formulation releases a therapeutic agent (e.g., a small molecule, nucleic acid, protein, peptide, polynucleotide, biologic), cosmetic agent, diagnostic agent, and/or prophylactic agent, at a controlled rate and at a controlled dose of release of the agent over a specific, extended period of time. In certain embodiments, the controlled-release formulation releases the therapeutic agent over an extended period of time. In certain embodiments, the therapeutic agent is an anti-cancer agent (e.g., taxane). In certain embodiments, the anti-cancer agent is an agent for treating leukemia, multiple myeloma, lymphoma, pancreatic cancer, lung cancer, prostate cancer, breast cancer, ovarian cancer, kidney cancer, liver cancer, Ewing's sarcoma, myeloma, Waldenstrom's macroglobulinemia, myelodysplastic syndrome (MDS), osteosarcoma, brain cancer, neuroblastoma, or colorectal cancer. In certain embodiments, the anti-cancer agent is an agent for treating leukemia (e.g., chronic lymphocytic leukemia (CLL), acute lymphoblastic leukemia (ALL),T-cell acute lymphoblastic leukemia (T-ALL), chronic myelogenous leukemia (CIVIL), acute myeloid leukemia (AML), acute monocytic leukemia (AMoL)). In certain embodiments, the anti-cancer agent is an agent for treating chronic lymphocytic leukemia (CLL). In certain embodiments, the anti-cancer agent is an agent for treating acute lymphoblastic leukemia (ALL). In certain embodiments, the anti-cancer agent is an agent for treating T-cell acute lymphoblastic leukemia (T-ALL). In certain embodiments, the anti-cancer agent is an agent for treating chronic myelogenous leukemia (CML). In certain embodiments, the anti-cancer agent is an agent for treating acute myeloid leukemia (AML). In certain embodiments, the anti-cancer agent is an agent for treating acute monocytic leukemia (AMoL). In certain embodiments, the anti-cancer agent is an agent for treating Waldenstrom's macroglobulinemia. In certain embodiments, the anti-cancer agent is an agent for treating Waldenstrom's macroglobulinemia associated with the MYD88 L265P somatic mutation. In certain embodiments, the anti-cancer agent is an agent for treating myelodysplastic syndrome (MDS). In certain embodiments, the anti-cancer agent is an agent for treating lymphoma (e.g., Burkitt's lymphoma, Hodgkin's lymphoma, non-Hodgkin's lymphoma). In some embodiments, the anti-cancer agent is an agent for treating Burkitt's lymphoma. In certain embodiments, the anti-cancer agent is an agent for treating Hodgkin's lymphoma. In certain embodiments, the anti-cancer agent is an agent for treating non-Hodgkin's lymphoma. In certain embodiments, the anti-cancer agent is an agent for treating multiple myeloma. In certain embodiments, the anti-cancer agent is an agent for treating melanoma. In certain embodiments, the anti-cancer agent is an agent for treating colorectal cancer.

In certain embodiments, the anti-cancer agent is an agent for treating breast cancer (e.g., recurring breast cancer, mutant breast cancer, HER2+ breast cancer, HER2-breast cancer, triple-negative breast cancer). In certain embodiments, the anti-cancer agent is an agent for treating recurring breast cancer. In certain embodiments, the anti-cancer agent is an agent for treating mutant breast cancer. In certain embodiments, the anti-cancer agent is an agent for treating HER2+ breast cancer. In certain embodiments, the anti-cancer agent is an agent for treating HER2-breast cancer. In certain embodiments, the anti-cancer agent is an agent for treating triple-negative breast cancer (TNBC). In certain embodiments, the anti-cancer agent is an agent for treating breast cancer. In certain embodiments, the anti-cancer agent is a taxane. In certain embodiments, the taxane is docetaxel. In certain embodiments, the taxane is paclitaxel. In certain embodiments, the taxane is cabazitaxel. In certain embodiments, the taxane is abraxane. In certain embodiments, the taxane is taxotere. In certain embodiments, the anti-cancer agent is an anthracycline (e.g., doxorubicin, epirubicin). In certain embodiments, the anti-cancer agent is an alkylating agent (e.g., a cytoxan). In certain embodiments, the anti-cancer agent is an agent for treating a bone cancer. In certain embodiments, the anti-cancer agent is an agent for treating osteosarcoma. In certain embodiments, the anti-cancer agent is an agent for treating Ewing's sarcoma. In some embodiments, the anti-cancer agent is an agent for treating brain cancer. In some embodiments, the anti-cancer agent is an agent for treating neuroblastoma. In some embodiments, the anti-cancer agent is an agent for treating lung cancer (e.g., small cell lung cancer (SCLC), non-small cell lung cancer). In some embodiments, the anti-cancer agent is an agent for treating small cell lung cancer (SCLC). In some embodiments, the anti-cancer agent is an agent for treating non-small cell lung cancer. In certain embodiments, the controlled-release formulation releases the anti-cancer therapeutic agent (e.g., taxane (e.g., docetaxel, paclitaxel)) over an extended period of time. In certain embodiments, the composition is a cosmetic composition, comprising a cosmetic agent. In certain embodiments, the composition is a cosmetic composition, comprising a cosmetic agent that is a polymer described herein. In certain embodiments, the composition is a nutraceutical composition, comprising a food, vitamin, mineral, nutraceutical, and/or nutritional agent. In certain embodiments, the composition is a composition with a non-medical application. In certain embodiments, the composition further comprises an agent (e.g., therapeutic agent (e.g., a small molecule, nucleic acid, protein, peptide, polynucleotide, biologic), cosmetic agent, diagnostic agent, and/or prophylactic agent), as described herein.

In certain embodiments, the composition is used in human applications (e.g., medical, industrial, research uses). In certain embodiments, the composition is used in non-human veterinary applications (e.g., used for non-human animals (e.g., farm animals, companion animals)). In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a research animal (e.g., primate, rat, mouse, dog, fish). In certain embodiments, the non-human animal is a fish, reptile, or amphibian. The non-human animal may be male or female at any stage of development. In certain embodiments, the non-human companion animal is a dog. In certain embodiments, the non-human companion animal is a cat. In certain embodiments, the non-human companion animal is a bird.

In certain embodiments, the composition is used in human applications. In certain embodiments, the composition is used in human medical applications. In certain embodiments, the composition is used in human surgical applications. In certain embodiments, the composition is used in topical applications. In certain embodiments, the composition is or is part of a bandage. In certain embodiments, the composition is a liquid spray-on bandage. In certain embodiments, the composition is a liquid spray-on bandage, in which the bandage forms into a gel on the skin of the subject once the liquid components of the polymers described herein are sprayed onto the skin.

In certain embodiments, the composition is or is part of a viscoelastic bandage. In certain embodiments, the composition is used in an intraoperative setting (e.g., laparascopic or open surgical setting). In certain embodiments, the composition is used as part of a drug depot comprising polymers described herein, in a tumor resection. In certain embodiments, the composition is used in a tumor resection. In certain embodiments, the composition is used to prevent peritoneal adhesion. In certain embodiments, the composition is used in an intraoperative setting to prevent post-operative peritoneal adhesion. In certain embodiments, the composition is applied to tissue at risk of a peritoneal adhesion after surgery, in an intraoperative setting to prevent post-operative peritoneal adhesion. In certain embodiments, the composition comprises polymers described herein for delivering one or more pharmaceutical agents to the peritoneum to prevent a peritoneal adhesion. In certain embodiments, the composition comprises a drug depot used in an intraoperative setting, and implanted during surgery. In certain embodiments, the composition comprises one or more pharmaceutical agents mixed with polymers described herein, and injected into a subject for later extended release of the one or more pharmaceutical agents during surgery. In certain embodiments, the composition comprises polymers described herein combined with a medical device implant for supporting the implant. In certain embodiments, the medical device implant is an orthopedic implant. In certain embodiments, the composition comprises polymers described herein used as a surgical mesh. In certain embodiments, the composition comprises polymers described herein used as a surgical mesh, wherein the pore size of the mesh is less than 1 mm. In certain embodiments, the composition comprises polymers described herein used as a tissue adhesive during surgery. In certain embodiments, the composition comprises polymers described herein used as biomaterial scaffolds for ligament and/or tendon repair, implanted during surgery. In certain embodiments, the composition comprises polymers described herein used as supports for installing vascular stents and/or vascular grafts, and are implanted during surgery. In certain embodiments, the composition comprises polymers described herein used as supports for installing implants during plastic, cosmetic, and/or reconstructive surgery. In certain embodiments, the composition comprises polymers described herein used as composites in dental surgery. In certain embodiments, the composition comprises polymers described herein used as composites in dental surgery, in combination with an inorganic filler with particle size in nanometers or micrometers.

In certain embodiments, the composition is delivered to a subject orally, rectally, parenterally, intracisternally, intravaginally, intranasally, intraperitoneally, topically (as by powders, creams, ointments, or drops), bucally, or as an oral or nasal spray. In certain embodiments, the composition is delivered by topical delivery. In certain embodiments, the composition is delivered by ocular delivery. In certain embodiments, the ocular delivery comprises delivery to the front of the eye. In certain embodiments, the ocular delivery comprises delivery to the back of the eye.

In certain embodiments, the composition is a scaffold for tissue engineering. In certain embodiments, the composition is a scaffold for tissue engineering, in research. In certain embodiments, the composition is a scaffold for tissue engineering comprising cells, growth factors, proteins, peptides, nucleic acids, small molecules, nutrients, saccharides, and/or cell binding domains (e.g., protein domains, sugars, amino acids, vitamins, minerals). In certain embodiments, saccharides comprise multiple saccharide units (e.g., polysaccharides, oligosaccharides). In certain embodiments, the composition comprises polymers described herein used as a tissue adhesive. In certain embodiments, the composition comprises polymers described herein used as scaffolds for orthopedic implants. In certain embodiments, the composition comprises polymers described herein used as biomaterial scaffolds for ligament and/or tendon repair. In certain embodiments, the composition comprises polymers described herein used as supports for installing vascular stents and/or vascular grafts. In certain embodiments, the composition comprises polymers described herein used as composites in dentistry. In certain embodiments, the composition comprises scaffolds used for nerve guidance conduits.

In certain embodiments, the composition is in the form of a particle. In certain embodiments, provided are compositions in the form of a plurality of particles. In certain embodiments, the particle is a nanoparticle or a microparticle. In certain embodiments, the particle are nanoparticle or microparticles. In certain embodiments, the particle is a micelle, liposome, or lipoplex. In certain embodiments, the particle encapsulates an agent, as described herein. In certain embodiments, the particle facilitates delivery of the agent (e.g., into a cell). In certain embodiments, the particle facilitates delivery of the agent to a subject, e.g., a human. In certain embodiments, the composition comprises the polymers and/or hydrogels described herein. In certain embodiments, the composition comprises the starting materials (e.g., a compound of Formula (A); and a compound of Formula (B)) for preparing the polymers and/or hydrogels described herein. In certain embodiments, the composition comprises the starting materials (e.g., a protein derivatized with an electrophile, a carbohydrate derivatized with an electrophile, or a compound of Formula (A); and a cyclic amine, an matrix metalloproteinase (MMP) degradable amine, a redox sensitive amine, a photocleavable amine, or a compound of Formula (B)) for preparing the polymers and/or hydrogels described herein.

Compositions described herein can be prepared by any method known in the art. In general, such preparatory methods include bringing the polymer described herein into association with one or more excipients, and may include one or more agents (e.g., therapeutic agent (e.g., a small molecule, nucleic acid, protein, peptide, polynucleotide, biologic), cosmetic agent, diagnostic agent, and/or prophylactic agent) and then, if necessary and/or desirable, shaping, and/or packaging the product into a desired single-or multi-dose unit. In certain embodiments, the agent (e.g., therapeutic agent (e.g., a small molecule, nucleic acid, protein, peptide, polynucleotide, biologic), cosmetic agent, diagnostic agent, and/or prophylactic agent) and the polymer of the composition are not covalently attached. In general, such preparatory methods include forming the polymer in situ.

In certain embodiments, the compositions further comprise an agent and are useful for delivering said agent (e.g., to a subject or cell). In certain embodiments, the compositions are pharmaceutical compositions which are useful for treating a disease in a subject in need thereof. In certain embodiments, the pharmaceutical compositions are useful for preventing a disease in a subject. In certain embodiments, the compositions comprise prophylactic compositions. In certain embodiments, the compositions comprise diagnostic compositions.

A composition as described herein may further comprise, or can be administered in combination with, one or more additional agents. In certain embodiments, the composition further comprises an agent (e.g., therapeutic agent, prophylactic agent, cosmetic agent, diagnostic agent, nutraceutical agent), as described herein. In certain embodiments, the agent is a protein, a peptide, a polynucleotide, or a small molecule. In certain embodiments, the agent is a therapeutic agent. In certain embodiments, the agent is a cosmetic agent. In certain embodiments, the agent is a diagnostic agent. In certain embodiments, the agent is a pharmaceutical agent (e.g., therapeutically and/or prophylactically active agent). In certain embodiments, the agent is a prophylactic agent. Pharmaceutical agents include therapeutically active agents. Pharmaceutical agents also include prophylactically active agents. In certain embodiments, the prophylactic agent is an antigen, antibody, or vaccine. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, polynucleotides, lipids, hormones, vitamins, vaccines, immunological agents, and cells and other biological materials. In certain embodiments, the agent is a biologic. In certain embodiments, the agent is a small molecule. In certain embodiments, the agent is a small molecule therapeutic agent. In certain embodiments, the small molecule is a marker. In certain embodiments, the small molecule is a small molecule label of biotin, radioactive isotopes, enzymes, luminescent agents, precipitating agents, fluorophores, or dyes. In certain embodiments, the small molecule label is a tag (e.g., a biotin derivative, radiometric label, or fluorophore). In certain embodiments, the fluorophore is a non-protein, organic fluorophore (e.g., a derivative of xanthine, cyanine, squaraine rotaxane, naphthalene, coumarin, oxadiazole, anthracene, pyrene, oxazine, acridine, arylmethine, tetrapyrrole). In certain embodiments, the small molecule is a fluorophore (e.g., a cyanine fluorophore (e.g., a Cy5.5 fluorophore)). In certain embodiments, the fluorophore is a cyanine derivative fluorophore. In certain embodiments, the small molecule is a diagnostic agent. In certain embodiments, the diagnostic agent is an organ function diagnosis agent, or radioactive diagnostic agent (e.g., diagnostic radiopharmaceutical agents). In certain embodiments, the small molecule is an imaging agent. In certain embodiments, the imaging agent is an X-ray contrast agent, fluorescent probes (e.g., fluorophore), radionuclide imaging agents (e.g., agents for gamma scintigraphy, positron emission tomography (PET)), or optical imaging agents (e.g., fluorophores). In certain embodiments, the small molecule therapeutic agent is an antibiotic, anesthetic, steroidal agent, anti-proliferative agent, anti-inflammatory agent, anti-angiogenesis agent, anti-neoplastic agent, anti-cancer agent, anti-diabetic agent, decongestant, antihypertensive, sedative, anti-cholinergic, analgesic, immunosuppressant, anti-depressant, anti-psychotic, β-adrenergic blocking agent, diuretic, cardiovascular active agent, vasoactive agent, non-steroidal, nutritional agent, anti-allergic agent, or pain-relieving agent. In certain embodiments, the small molecule is an ophthalmic agent. In certain embodiments, the small molecule is a therapeutic ophthalmic agent. In certain embodiments, the small molecule therapeutic agent is an anti-cancer agent (e.g., taxane). In certain embodiments, the anti-cancer agent is an agent for treating breast cancer. In certain embodiments, the anti-cancer agent is a taxane. In certain embodiments, the taxane is docetaxel. In certain embodiments, the taxane is paclitaxel. In certain embodiments, the taxane is cabazitaxel. In certain embodiments, the taxane is abraxane. In certain embodiments, the taxane is taxotere. In certain embodiments, the anti-cancer agent is an anthracycline (e.g., doxorubicin, epirubicin). In certain embodiments, the anti-cancer agent is an alkylating agent (e.g., a cytoxan).

Compositions can be prepared, packaged, and/or sold in bulk, as a single unit dose, and/or as a plurality of single unit doses. A "unit dose" is a discrete amount of the composition comprising a predetermined amount of the agent. The amount of the agent is generally equal to the dosage of the agent which would be administered to a subject and/or a convenient fraction of such a dosage, such as one-half or one-third of such a dosage. In certain embodiments, the composition comprises a drug depot, comprising one or more pharmaceutical agents, in which the one or more pharmaceutical agents are released over an extended period of time.

Relative amounts of the polymer, excipient, agent, and/or any additional ingredients in a composition described herein will vary, depending upon the identity, size, and/or condition of the subject treated and further depending upon the route by which the composition is to be administered (e.g., ocular delivery, transdermal delivery, intravenous delivery). The composition may comprise between 0.1% and 100% (w/w) agent. In certain embodiments, the composition may include no agent.

Excipients and accessory ingredients used in the manufacture of provided compositions include inert diluents, dispersing and/or granulating agents, surface active agents and/or emulsifiers, disintegrating agents, binding agents, preservatives, buffering agents, lubricating agents, and/or oils. Excipients and accessory ingredients, such as cocoa butter, PEGylated lipids, phospholipids, suppository waxes, coloring agents, coating agents, sweetening, flavoring, and perfuming agents, may also be present in the composition. In certain embodiments, the excipient comprises a filler (e.g., an inorganic filler). In certain embodiments, the excipient comprises a plant protein. In certain embodiments, the excipient comprises a polysaccharide (e.g., a plant polysaccharide). In certain embodiments, the excipient comprises a biodegradable excipient.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan monostearate (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste); gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Compositions may be formulated into liquid dosage forms for oral and parenteral administration include pharmaceutically acceptable emulsions, microemulsions, solutions, suspensions, syrups, and elixirs. In addition to the agents, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants, such as wetting agents, emulsifying and suspending agents, sweetening, flavoring, and perfuming agents. In certain embodiments for parenteral administration, the particles described herein are mixed with solubilizing agents, such as Cremophor , alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono-or di-glycerides. In addition, fatty acids, such as oleic acid, are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Dosage forms for topical and/or transdermal administration of a composition described herein may include ointments, pastes, creams, lotions, gels, powders, solutions, sprays, inhalants, and/or patches. Generally, the agent is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an agent to the body. Such dosage forms can be prepared, for example, by dissolving and/or dispensing the agent in the proper medium. Alternatively or additionally, the rate can be controlled by either providing a rate controlling membrane and/or by dispersing the agent in a polymer matrix and/or gel.

Suitable devices for use in delivering intradermal compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the polymer in powder form through the outer layers of the skin to the dermis are suitable.

Formulations suitable for topical administration include liquid and/or semi-liquid preparations, such as liniments, lotions, oil-in-water, and/or water-in-oil emulsions, such as creams, ointments, and/or pastes, and/or solutions, and/or suspensions. Topically administrable formulations may, for example, comprise from about 1% to about 10% (w/w) agent, although the concentration of the agent can be as high as the solubility limit of the agent in the solvent. Formulations for topical administration may further comprise one or more of the additional ingredients described herein.

A composition described herein can be prepared, packaged, and/or sold in a formulation suitable for pulmonary administration via the buccal cavity. Such a formulation may comprise dry particles which comprise the agent and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the agent dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the agent may constitute 0.1 to 20% (w/w) of the composition. The propellant may further comprise additional ingredients such as a liquid non-ionic and/or solid anionic surfactant and/or a solid diluent (which may have a particle size of the same order as particles comprising the agent).

Compositions described herein formulated for pulmonary delivery may provide the agent in the form of droplets of a solution and/or suspension. Such formulations can be prepared, packaged, and/or sold as aqueous and/or dilute alcoholic solutions and/or suspensions, optionally sterile, comprising the agent, and may conveniently be administered using any nebulization and/or atomization device. Such formulations may further comprise one or more additional ingredients including a flavoring agent such as saccharin sodium, a volatile oil, a buffering agent, a surface active agent, and/or a preservative such as methylhydroxybenzoate.

Formulations described herein as being useful for pulmonary delivery are useful for intranasal delivery of a pharmaceutical composition described herein. Another formulation suitable for intranasal administration is a coarse powder comprising the agent and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the agent, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) agent, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the agent. Such powdered, aerosolized, and/or aerosolized formulations, when dispersed, may have an average particle and/or droplet size in the range from about 0.1 to about 200 nanometers, and may further comprise one or more of the additional ingredients described herein.

A composition described herein can be prepared, packaged, and/or sold in a formulation for ophthalmic administration. Such compositions (formulations) may, for example, be in the form of eye drops including, for example, a 0.1-1.0% (w/w) solution and/or suspension of the agent in an aqueous or oily liquid carrier or excipient. Such drops may further comprise buffering agents, salts, and/or one or more other of the additional ingredients described herein. Other opthalmically-administrable formulations which are useful include those which comprise the agent in microcrystalline form and/or in a liposomal preparation. Ear drops and/or eye drops are also contemplated as being within the scope of this disclosure. In certain embodiments, the composition comprises a drug depot used in an intraoperative setting, and implanted during ocular surgery. In certain embodiments, the composition comprises an opthalmic composition (e.g., artificial tears, ocular lubricants). In certain embodiments, the composition comprises an ophthalmic composition delivered to the front of the eye. In certain embodiments, the composition comprises an ophthalmic composition comprising a drug depot, delivered to the front of the eye, for extended and/or controlled release. In certain embodiments, the composition comprises an ophthalmic composition comprising one or more pharmaceutical agents, delivered to the front of the eye, for extended and/or controlled release. In certain embodiments, the composition comprises an ophthalmic composition delivered to the back of the eye. In certain embodiments, the composition comprises an ophthalmic composition comprising a drug depot, delivered to the back of the eye, for extended and/or controlled release. In certain embodiments, the composition comprises an ophthalmic composition comprising one or more pharmaceutical agents, delivered to the back of the eye, for extended and/or controlled release. In certain embodiments, the composition comprises an ophthalmic composition implanted into the eye. In certain embodiments, the ophthalmic composition comprises one or more pharmaceutical agents mixed with polymers described herein, and injected into a subject for later extended release of the one or more pharmaceutical agents.

Although the descriptions of compositions provided herein are principally directed to compositions which are suitable for administration to humans, it will be understood by the skilled artisan that such compositions are generally suitable for administration to animals of all sorts. Modification of compositions suitable for administration to humans in order to render the compositions suitable for administration to various animals is well understood, and the ordinarily skilled veterinary pharmacologist can design and/or perform such modification with ordinary experimentation.

Compositions provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific agent employed; the specific composition employed; the age, body weight, general health, sex, and diet of the subject; the time of administration, route of administration, and rate of excretion of the specific agent employed; the duration of the treatment; drugs used in combination or coincidental with the specific agent employed; and like factors well known in the medical arts.

The compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the composition described herein is suitable for topical administration to the eye of a subject. In certain embodiments, the composition described herein is suitable for administration via ocular delivery, transdermal delivery, and/or intravenous delivery (e.g., intravenous injection). In certain embodiments, the composition described herein is suitable for administration to the eye (e.g., back of the eye, front of the eye) of a subject. In certain embodiments, the composition described herein is suitable for topical administration to the eye (e.g., back of the eye, front of the eye) of a subject.

The exact amount of a polymer (e.g. polymer which includes an agent required to achieve an effective amount) will vary from subject to subject, depending, for example, on species, age, and general condition of a subject, severity of the side effects or disorder, identity of the particular agent to be delivered, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a polymer (e.g. polymer which includes an agent) described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a polymer (e.g. polymer which includes an agent) described herein. In certain embodiments, a dose described herein includes independently between 1 mg and 3 mg, inclusive, of a polymer (e.g. polymer which includes an agent) described herein. In certain embodiments, a dose described herein includes independently between 3 mg and 10 mg, inclusive, of a polymer (e.g. polymer which includes an agent) described herein. In certain embodiments, a dose described herein includes independently between 10 mg and 30 mg, inclusive, of a polymer (e.g. polymer which includes an agent) described herein. In certain embodiments, a dose described herein includes independently between 30 mg and 100 mg, inclusive, of a polymer (e.g. polymer which includes an agent) described herein.

Dose ranges as described herein provide guidance for the administration of provided compositions to an adult. The amount to be administered to, for example, a child or an adolescent can be determined by a medical practitioner or person skilled in the art and can be lower or the same as that administered to an adult. In certain embodiments, a dose described herein is a dose to an adult human whose body weight is 70 kg.

The polymer (e.g. polymer which includes an agent) can be administered concurrently with, prior to, or subsequent to one or more additional agents (e.g., a pharmaceutical agent), in addition to the polymer in the composition and may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., genetic disease, proliferative disease, hematological disease, neurological disease, painful condition, psychiatric disorder, metabolic disorder, long-term medical condition, inflammatory disease, autoinflammatory disease, liver disease, lung disease, spleen disease, familial amyloid neuropathy, cardiovascular disease, viral infection, infectious disease, fibrotic condition, or autoimmune disease). Each additional pharmaceutical agent may be administered at a dose and/or on a time schedule determined for that pharmaceutical agent. The additional pharmaceutical agents may also be administered together with each other and/or with the polymer or composition described herein in a single dose or administered separately in different doses. The particular combination to employ in a regimen will take into account compatibility of the polymer (e.g. polymer which includes an agent) described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include anti-proliferative agents, anti-cancer agents, cytotoxic agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, and pain-relieving agents. In certain embodiments, the additional pharmaceutical agent is an anti-proliferative agent. In certain embodiments, the additional pharmaceutical agent is an anti-cancer agent. In certain embodiments, the additional pharmaceutical agent is an anti-viral agent. In certain embodiments, the additional pharmaceutical agent is a binder or inhibitor of a protein kinase. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-trans retinoic acids, and other agents that promote differentiation. In certain embodiments, the polymers (e.g. polymers which include an agent) described herein or compositions (e.g., pharmaceutical compositions) can be administered in combination with an anti-cancer therapy including surgery, radiation therapy, transplantation (e.g., stem cell transplantation, bone marrow transplantation), immunotherapy, and chemotherapy.

In some embodiments, the particle (e.g., a nanoparticle) comprises the polymer. In some embodiments, the particle is substantially soluble in water (e.g., hydrophilic). In some embodiments, the particle is substantially insoluble in water (e.g., hydrophobic). In some embodiments, the particle is substantially insoluble in water and greater than about 10,000 parts water are required to dissolve 1 part compound. In one embodiment, the particle is amphiphilic. In one embodiment, the particle comprises a segment that is hydrophobic and a segment that is hydrophilic. In some embodiments, the particle (e.g., a nanoparticle) comprises a composition comprising a polymer. In some embodiments, the composition comprising a polymer described herein is a hydrogel.

In some embodiments, the percentage of the particle that comprises a polymer is between about 1 and about 100% (e.g., about 1%, about 2%, about 3%, about 4%, about 5%, about 10%, about 15%, about 20%, about 30%, about 40%, about 50%, about 60%, about 70%, about 80%, about 90%, or about 100%). In some embodiments, the percentage of the particle that comprises a polymer is less than about 50%, e.g., less than about 40%, less than about 35%, less than about 30%, less than about 25%, less than about 20%, less than about 15%, or less than about 10%. In some embodiments, the percentage of the particles that comprises a polymer is between about 5% and about 50%, about 5% and about 40%, about 5% and about 30%, about 5% and about 25%, or about 5% and about 20%. In some embodiments, the percentage of the particle that comprises a polymer is between about 5% and 90%. In some embodiments, the percentage of the particles that comprises a polymer is between about 5% and about 75%. In some embodiments, the percentage of particle that comprises a polymer is between about 5% and about 50%. In some embodiments, the percentage of the particle that comprises a polymer is between about 10% and about 25%.

In some embodiments, the total amount of the polymer present in the particle is greater than about 5% (e.g., about 6%, about 7%, about 8%, about 9%, about 10%, about 12%, about 15%, about 20%, about 25%, about 30%, or more) of the total size or weight of the conjugate or particle. In some embodiments, the total amount of the polymer present in the conjugate or particle is greater than about 10% (e.g., about 12%, about 15%, about 20%, about 25%, about 30%, or more) of the total size or weight of the conjugate or particle.

In another aspect, provided are kits including a first container comprising a polymer or composition described herein and instructions for use. The kits may further comprise a container (e.g., a vial, ampule, bottle, syringe, and/or dispenser package, or other suitable container). In some embodiments, provided kits may optionally further include a second container comprising an excipient for dilution or suspension of a polymer or composition described herein. In some embodiments, the polymers (e.g., polymer starting materials of Formula (A) and Formula (B)) described herein provided in the first container and the second container are combined to form one unit dosage form. In some embodiments, the compositions described herein provided in the first container and the second container are combined to form one unit dosage form. In some embodiments, provided are kits with separate vials containing each of the starting materials (e.g., a vial with a compound of Formula (A) and a vial with a compound of Formula (B)) for forming the polymers described herein. In some embodiments, provided are kits with separate vials containing each of the starting materials (e.g., a vial with a protein derivatized with an electrophile, a carbohydrate derivatized with an electrophile or a compound of Formula (A) and a vial with a cyclic amine, an matrix metalloproteinase (MMP) degradable amine, a redox sensitive amine, a photocleavable amine, or a compound of Formula (B)) for forming the polymers described herein. In some embodiments, provided are kits with vials containing the starting materials for forming the hydrogels described herein in situ.

In certain embodiments, the kits are useful for delivering a polymer (e.g., polymer comprising an agent) (e.g., to a subject, cell, tissue, or biological sample). In certain embodiments, a kit described herein further includes instructions for using the kit (e.g., instructions for administering to a subject or contacting a cell, tissue, or biological sample with the polymer or the composition thereof). A kit described herein may also include information as required by a regulatory agency such as the U.S. Food and Drug Administration (FDA). In certain embodiments, the information included in the kits is prescribing information. In certain embodiments, the kits and instructions provide for delivering a polymer (e.g., polymer comprising an agent. In certain embodiments, the kits and instructions provide for uses of the polymer described herein (e.g., for therapeutic, ophthalmic, intraoperative, or cosmetic use; as part of materials (e.g., biodegradable materials, biocompatible materials, wound dressing (e.g., bandages)), drug depots, coatings, or as scaffolds for tissue engineering. A kit described herein may include one or more additional pharmaceutical agents described herein as a separate composition.

Methods of Synthesis

The present disclosure provides methods for making a polymer of Formula (I):

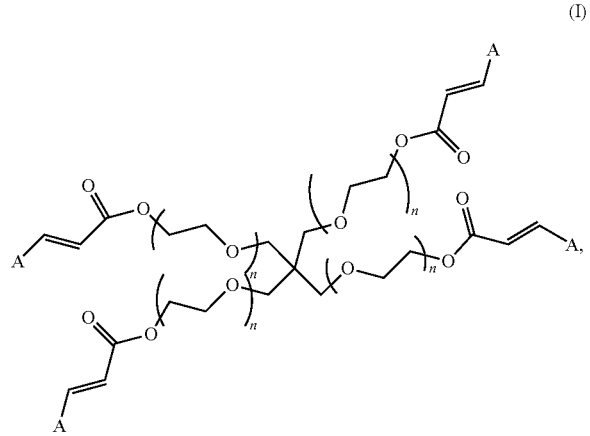

(I)

or a pharmaceutically acceptable salt, co-crystal, tautomer, stereoisomer, or isotopically labeled derivative thereof, comprising:

reacting a tetra-arm polyethylene glycol alkynoate compound of Formula (A):

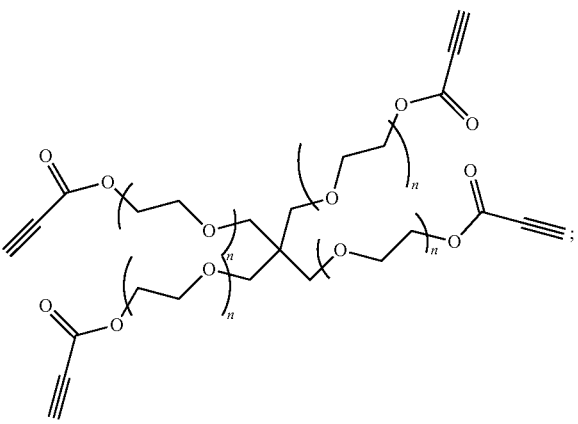

(A)

or a pharmaceutically acceptable salt, co-crystal, tautomer, stereoisomer, or isotopically labeled derivative thereof, with an amine X;

or a pharmaceutically acceptable salt, co-crystal, tautomer, stereoisomer, or isotopically labeled derivative thereof, wherein:

each n independently is between 10-150;

each R independently is hydrogen, optionally substituted alkyl, optionally substituted alkenyl, or optionally substituted alkynyl;

each Z independently is hydrogen, optionally substituted alkyl, optionally substituted alkenyl, optionally substituted alkynyl, or of the Formula (I-Z):

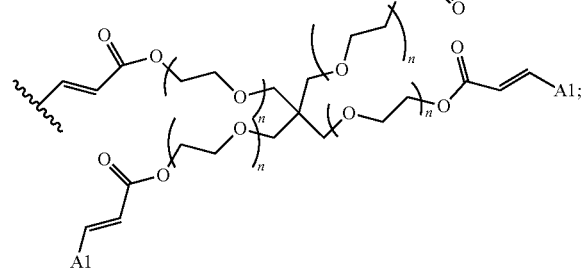

(I-Z)

wherein each A1 independently is an amine; under suitable conditions to form a polymer of Formula (I).

The present disclosure provides methods for making a polymer of Formula (I):

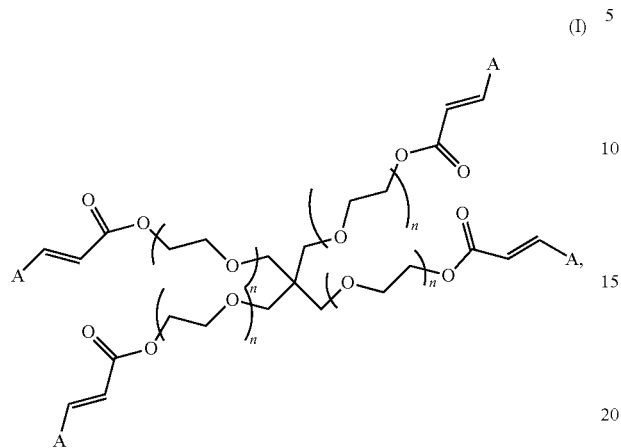

(I)

or a pharmaceutically acceptable salt, co-crystal, tautomer, stereoisomer, or isotopically labeled derivative thereof, comprising:

reacting a tetra-arm polyethylene glycol alkynoate compound of Formula (A):

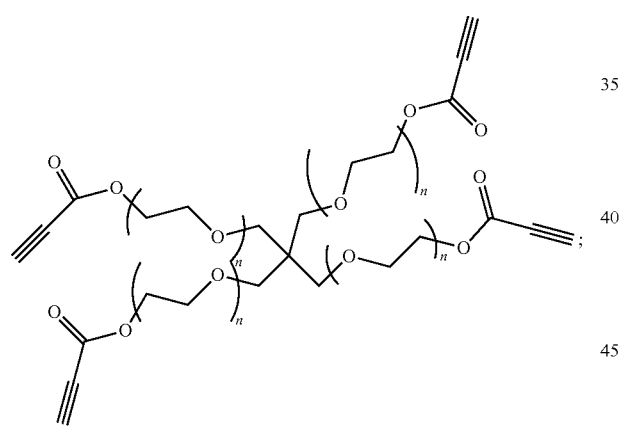

(A)

or a pharmaceutically acceptable salt, co-crystal, tautomer, stereoisomer, or isotopically labeled derivative thereof, with a compound of Formula (B):

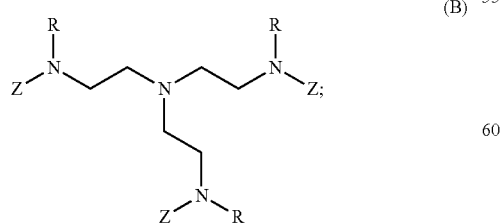

(B)

or a pharmaceutically acceptable salt, co-crystal, tautomer, stereoisomer, or isotopically labeled derivative thereof, wherein: each n independently is between 10-150;

each R independently is hydrogen, optionally substituted alkyl, optionally substituted alkenyl, or optionally substituted alkynyl;

each Z independently is hydrogen, optionally substituted alkyl, optionally substituted alkenyl, optionally substituted alkynyl, or of the Formula (I-Z):

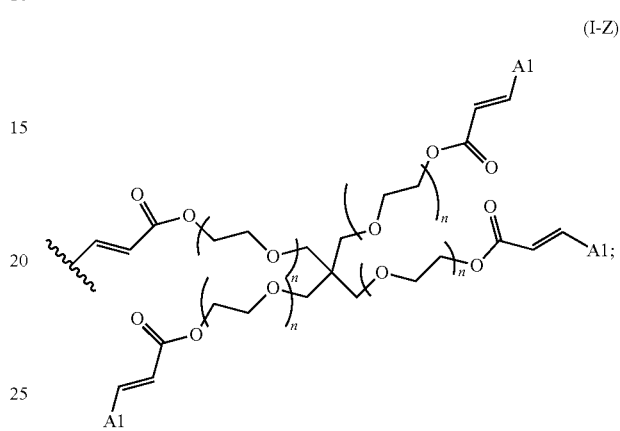

(I-Z)

wherein each A1 independently is an amine;
under suitable conditions to form a polymer of Formula (I).

The present disclosure provides methods for making a polymer described herein, comprising:

reacting a protein derivatized with an electrophile, a carbohydrate derivatized with an electrophile, or a tetra-arm polyethylene glycol alkynoate compound of Formula (A):

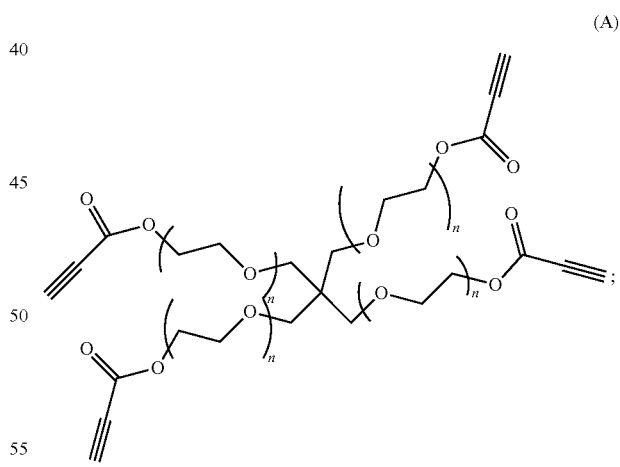

(A)

or a pharmaceutically acceptable salt, co-crystal, tautomer, stereoisomer, or isotopically labeled derivative thereof, with an amine selected from the group consisting of: linear amines, branched amines, polyamines, cyclic amines, matrix metalloproteinase (MMP) degradable amines, redox sensitive amines, photocleavable amines, and compounds of Formula (B):

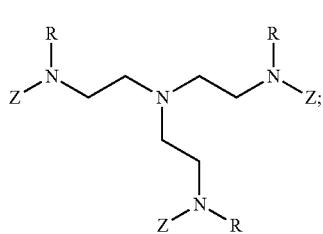

or a pharmaceutically acceptable salt, co-crystal, tautomer, stereoisomer, or isotopically labeled derivative thereof; wherein:

each n independently is between 10-150;

each R independently is hydrogen, optionally substituted alkyl, optionally substituted alkenyl, or optionally substituted alkynyl;

each Z independently is hydrogen, optionally substituted alkyl, optionally substituted alkenyl, optionally substituted alkynyl, or of the Formula (I-Z):

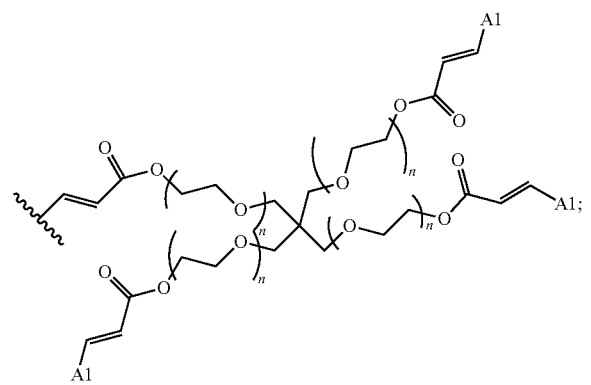

wherein each A1 independently is an amine; under suitable conditions.

In certain embodiments, the amine X is of the formula

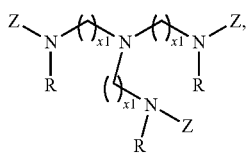

wherein each R independently is hydrogen, optionally substituted alkyl, optionally substituted alkenyl, or optionally substituted alkynyl; each Z independently is hydrogen, optionally substituted alkyl, optionally substituted alkenyl, or optionally substituted alkynyl; each x1 is independently 2, 3, 4, or 5; and each n independently is 15-140. In certain embodiments, the amine X is of the formula

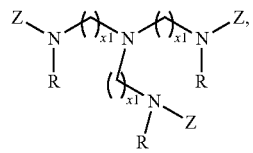

and at least one instance of x1 is 2 or 3. In certain embodiments, at least one instance of x1 is 2. In certain embodiments, at least one instance of x1 is 3. In certain embodiments, at least one instance of x1 is 4. In certain embodiments, at least one instance of x1 is 5. In certain embodiments, the amine X is a compound of Formula (B):

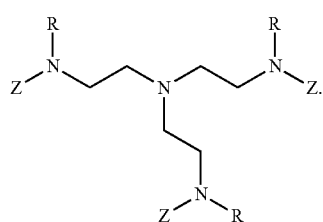

In certain embodiments, the amine X is a compound of Formula (B):

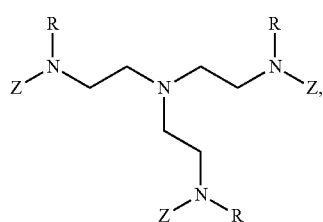

wherein each instance of R is independently optionally substituted alkyl; wherein each instance of Z is independently hydrogen. In certain embodiments, the amine X is a compound of Formula (B)

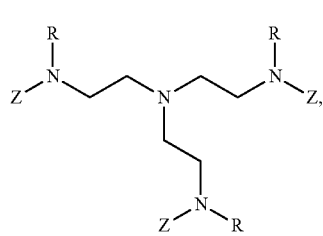

wherein each instance of R is independently optionally substituted $C_{1-6}$ alkyl; wherein each instance of Z is independently hydrogen. In certain embodiments, the amine X is a compound of Formula (B):

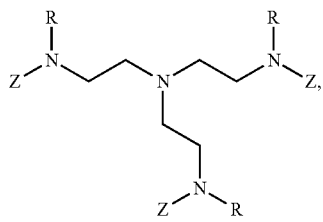

(B)

wherein each instance of R is independently unsubstituted C$_{1-6}$ alkyl;

wherein each instance of Z is independently hydrogen. In certain embodiments, the amine X is a compound of Formula (B):

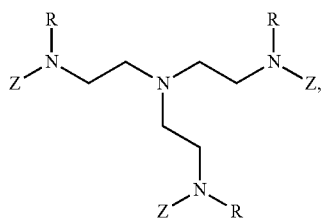

(B)

wherein all instances of R are unsubstituted methyl; wherein all instances of Z are independently hydrogen.

In certain embodiments, the amine X is of the formula:

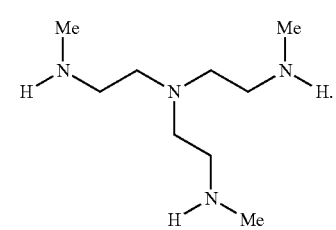

In certain embodiments, the amine X is of the formula:

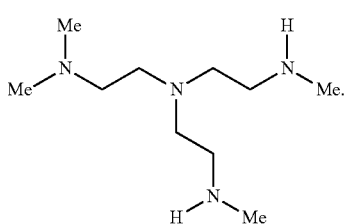

In certain embodiments, the amine X is of the formula:

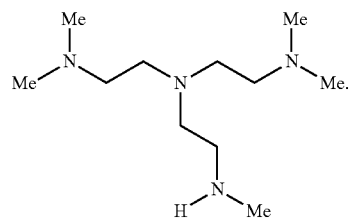

In certain embodiments, the amine X is of the formula:

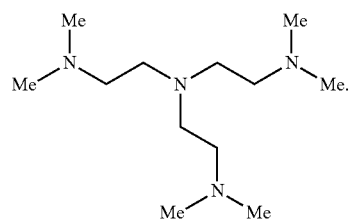

In certain embodiments, the amine X is of the formula:

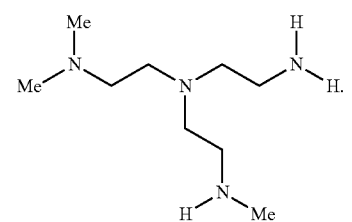

In certain embodiments, the amine X is of the formula:

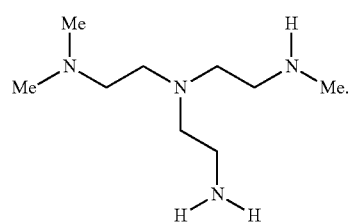

In certain embodiments, the amine X is of the formula:

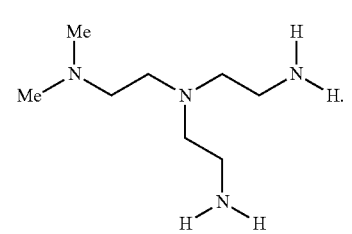

In certain embodiments, the amine X is of the formula:

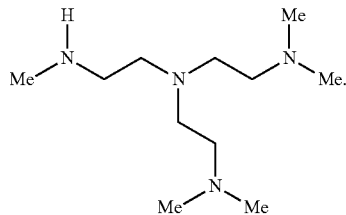 [SMILES: CNCCN(CCN(C)C)CCN(C)C]

In certain embodiments, the amine X is of the formula:

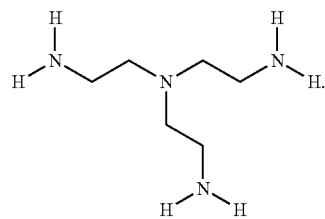

In certain embodiments, in methods of preparing a polymer described herein, the amine is a compound of Formula (B):

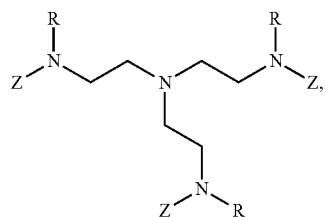

(B)

each instance of R is independently optionally substituted alkyl; wherein each instance of Z is independently hydrogen. In certain embodiments, in methods of preparing a polymer described herein, the amine is a compound of Formula (B):

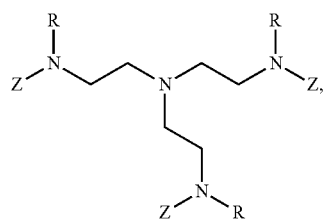

(B)

wherein each instance of R is independently optionally substituted $C_{1-6}$ alkyl; wherein each instance of Z is independently hydrogen. In certain embodiments, in methods of preparing a polymer described herein, the amine is a compound of Formula (B):

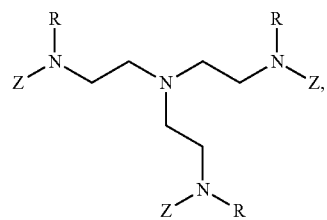

(B)

wherein each instance of R is independently unsubstituted $C_{1-6}$ alkyl; wherein each instance of Z is independently hydrogen. In certain embodiments, in methods of preparing a polymer described herein, the amine is a compound of Formula (B):

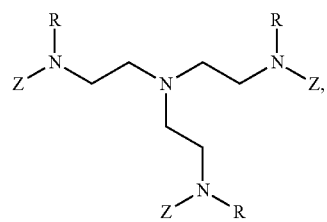

(B)

wherein all instances of R are unsubstituted methyl; wherein all instances of Z are independently hydrogen.

In certain embodiments, in methods of preparing a polymer described herein, the amine is a compound of Formula (B) of the formula:

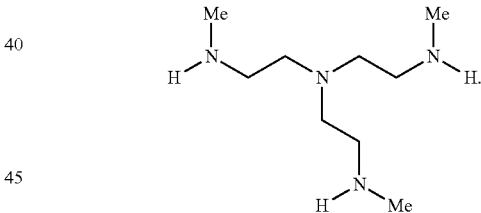

In certain embodiments, in methods of preparing a polymer described herein, the amine is a compound of Formula (B) of the formula:

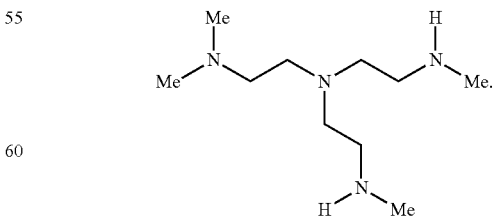

In certain embodiments, in methods of preparing a polymer described herein, the amine is a compound of Formula (B) of the formula:

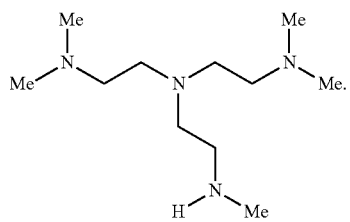 [SMILES: CNCCN(CCN(C)C)CCN(C)C]

In certain embodiments, in methods of preparing a polymer described herein, the amine is a compound of Formula (B) of the formula:

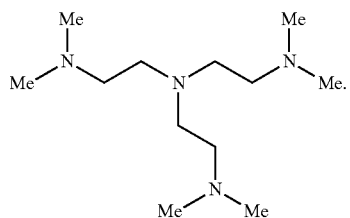

In certain embodiments, in methods of preparing a polymer described herein, the amine is a compound of Formula (B) of the formula:

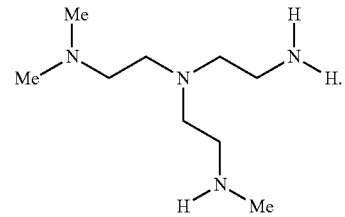

In certain embodiments, in methods of preparing a polymer described herein, the amine is a compound of Formula (B) of the formula:

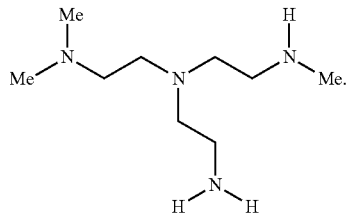 [SMILES: CNCCN(CCN)CCN(C)C]

In certain embodiments, in methods of preparing a polymer described herein, the amine is a compound of Formula (B) of the formula:

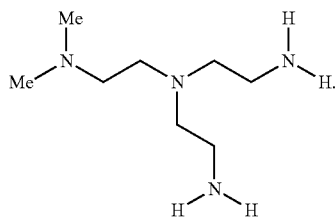

In certain embodiments, in methods of preparing a polymer described herein, the amine is a compound of Formula (B) of the formula:

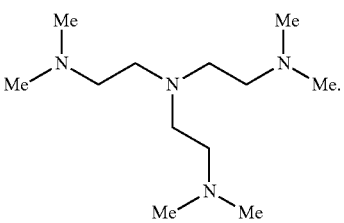 [SMILES: CN(C)CCN(CCN(C)C)CCN(C)C]

In certain embodiments, in methods of preparing a polymer described herein, the amine is a compound of Formula (B) of the formula:

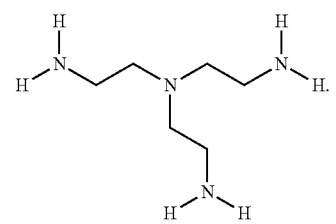

In certain embodiments, the protein used in the methods of synthesizing polymers described herein is any type of protein.
In certain embodiments, the protein used in the methods of synthesizing polymers described herein is a plant protein. In certain embodiments, the protein used in the methods of synthesizing polymers described herein is an animal protein. In certain embodiments, the protein used in the methods of synthesizing polymers described herein is a fibrous protein (e.g., collagen). In certain embodiments, the protein is a fibrous protein in the extracellular matrix. In certain embodiments, the protein is a fibrous protein in connective tissue. In certain embodiments, the protein used in the method of synthesizing polymers described herein is collagen. In certain embodiments, the protein used in the method of synthesizing polymers described herein is a product produced by processing collagen. In certain embodiments, the protein used in the methods of synthesizing polymers described herein is gelatin. In certain embodiments, the protein used in the methods of synthesizing polymers described herein is a globular protein (e.g., myoglobin). In certain embodiments, the protein used in the methods of synthesizing polymers described herein is a membrane protein (e.g., rhodopsin).

In certain embodiments, the carbohydrate (derivatized with an electrophile) used in the method of synthesizing polymers described herein is a polysaccharide. In certain embodiments, the polysaccharide is a plant polysaccharide. In certain embodiments, the polysaccharide is a linear polysaccharide. In certain embodiments, the carbohydrate (derivatized with an electrophile) used in the method of synthesizing polymers described herein is a linear polysaccharide. In certain embodiments, the linear polysaccharide is glycosaminoglycan. In certain embodiments, the linear polysaccharide with an amino sugar and uronic acid where the linear polysaccharide derivatized with an electrophile, that is used in the method of synthesizing polymers described herein is glycosaminoglycan. In certain embodiments, the linear polysaccharide that is derivatized with an electrophile has an amino sugar and uronic acid. In certain embodiments, the glycosaminoglycan is chondroitin. In certain embodiments, the glycosaminoglycan is dermatan. In certain embodiments, the glycosaminoglycan is heparin and/or heparan. In certain embodiments, the glycosaminoglycan is keratin. In certain embodiments, the glycosaminoglycan used in the method of synthesizing polymers described herein is hyaluronic acid.

In certain embodiments, the amine used in the method of synthesizing polymers described herein is selected from the group consisting of: linear amines, branched amines, polyamines, cyclic amines, matrix metalloproteinase (MMP) degradable amines, redox sensitive amines, photocleavable amines, and compounds of Formula (B):

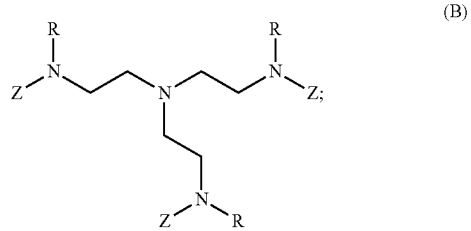

(B)

wherein each R independently is hydrogen, optionally substituted alkyl, optionally substituted alkenyl, or optionally substituted alkynyl; each Z independently is hydrogen, optionally substituted alkyl, optionally substituted alkenyl, optionally substituted alkynyl, or of the Formula (I-Z):

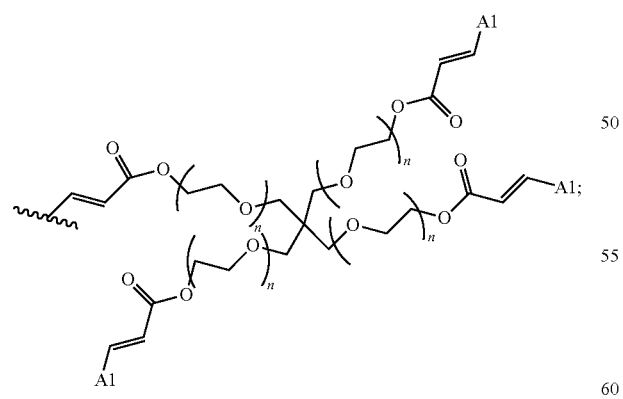

(I-Z)

wherein each A1 independently is an amine. The definitions of R, Z, A1, and n are as discussed above.

In certain embodiments, the amine used in the method of synthesizing polymers described herein is a linear amine. In certain embodiments, the amine used in the method of synthesizing polymers described herein is a branched amine. In certain embodiments, the amine used in the method of synthesizing polymers described herein is a straight-chain amine or branched amine. In certain embodiments, the amine used in the method of synthesizing polymers described herein is a straight-chain amine. In certain embodiments, the amine used in the method of synthesizing polymers described herein is a linear amine. In certain embodiments, the amine used in the method of synthesizing polymers described herein is a branched amine. In certain embodiments, the amine used in the method of synthesizing polymers described herein is an alkylamine. In certain embodiments, the amine used in the method of synthesizing polymers described herein is selected from the group consisting of dodecyl amine, 3-amino-1,2-propanediol, 5-amino-pentanol, N,N-dimethylethylenediamine, 2-morpholinoethylamine, and 2,2'-((oxybis(ethane-2,1-diyl))bis(oxy))diethanamine. In certain embodiments, the amine used in the method of synthesizing polymers described herein is a primary amine (e.g., —NH$_2$). In certain embodiments, the amine used in the method of synthesizing polymers described herein is —NH$_2$. In certain embodiments, the amine used in the method of synthesizing polymers described herein is a secondary amine (e.g., —NH(optionally substituted alkyl)). In certain embodiments, the amine used in the method of synthesizing polymers described herein is of formula —NH($R^{a2}$), wherein $R^{a2}$ is optionally substituted alkyl, optionally substituted alkenyl, or optionally substituted alkynyl. In certain embodiments, the amine used in the method of synthesizing polymers described herein is a tertiary amine. In certain embodiments, the amine used in the method of synthesizing polymers described herein is of formula —N($R^{a2}$)$_2$, wherein each instance of $R^{a2}$ is independently optionally substituted alkyl, optionally substituted alkenyl, or optionally substituted alkynyl. In certain embodiments, the cyclic amine used in the method of synthesizing polymers described herein is of the formula:

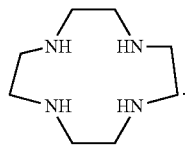

In certain embodiments, the cyclic amine is aziridine. In certain embodiments, the cyclic amine is azetidine, pyrrolidine, pipiridine, piperazine, morpholine, or thiomorpholine. In certain embodiments, the cyclic amine is piperidine.

In certain embodiments, the amine used in the method of synthesizing polymers described herein is a polyamine. A "polyamine" refers to a compound with more than one amine moiety. In certain embodiments, the amine used in the method of synthesizing polymers described herein is a MMP-degradable amine. In certain embodiments, the amine used in the method of synthesizing polymers described herein is a MMP-1 degradable amine. In certain embodiments, the amine used in the method of synthesizing polymers described herein is a MMP-2 degradable amine. In certain embodiments, the amine used in the method of synthesizing polymers described herein is a redox sensitive amine. In certain embodiments, the amine used in the method of synthesizing polymers described herein is a photocleavable amine. In certain embodiments, the amine used in the method of synthesizing polymers described herein is a compound of Formula (B):

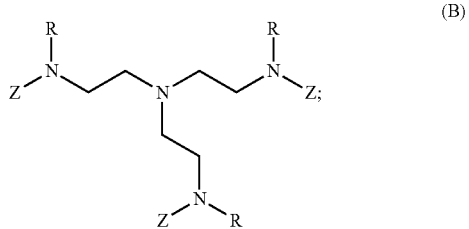

(B)

as described above.

In certain embodiments, the suitable conditions for preparing a polymer of Formula (I) do not include a catalyst or initiator. In certain embodiments, the suitable conditions do not include the formation of radicals. In certain embodiments, the suitable conditions do not include buffers. In certain embodiments, the suitable conditions do not include specific thermal conditions. In certain embodiments, the suitable conditions are the conditions during "the step of reacting" disclosed below.

In certain embodiments, the step of reacting is performed in a protic solvent. In certain embodiments, the step of reacting is performed in a polar solvent. In certain embodiments, the step of reacting is performed in a polar protic solvent. In certain embodiments, the step of reacting is performed in water. For example, the solvent used for the step of reacting is performed in a protic solvent, or a mixture of protic and aprotic solvents. In certain embodiments, the step of reacting is performed in phosphate-buffered saline solution (PBS). In certain embodiments, step of reacting is performed in a buffer solution. In certain embodiments, the step of reacting is performed in a buffer solution comprising salts (e.g., sodium chloride, potassium chloride). In certain embodiments, the step of reacting is performed in a saline solution. In certain embodiments, the step of reacting is performed in a buffer solution comprising sodium hydrogen phosphate. In certain embodiments, the step of reacting is performed in the body. In certain embodiments, the step of reacting is performed under physiological conditions (e.g., at physiological temperature, at physiological pH).

In certain embodiments, the step of reacting is performed at room temperature (e.g., 20-25° C.). In certain embodiments, the step of reacting is performed at a non-human (e.g., mammal) physiological temperature. In certain embodiments, the step of reacting is performed at human physiological temperature (e.g., 36-37.5° C.). In certain embodiments, the step of reacting is performed at approximately 30-37° C. In certain embodiments, the step of reacting is performed at approximately 30° C., 31° C., 32° C., 33° C., 34° C., 35° C., 36° C., or 37° C. In certain embodiments, the step of reacting is performed at approximately 35° C. In certain embodiments, the step of reacting is performed at approximately 36° C. In certain embodiments, the step of reacting is performed at approximately 37° C. In certain embodiments, the step of reacting is performed for about 0.5-3.0 hours. In certain embodiments, the step of reacting is performed for about 0.5-2.0 hours. In certain embodiments, the step of reacting is performed for about 0.5-1.5 hours. In certain embodiments, the step of reacting is performed for about 0.5-1.0 hours. In certain embodiments, the step of reacting is performed for about 1.0 hour. In certain embodiments, the step of reacting is performed for about 0.5-3.0 hours, about 0.5-2.0 hours, about 0.5-1.5 hours, or 0.5-1.0 hours, while stirring.

In certain embodiments, the suitable conditions comprise a molar ratio of Formula (A): amine X of about 6:4. In certain embodiments, the suitable conditions comprise a molar ratio of Formula (A): amine X of about 3:2. In certain embodiments, the suitable conditions comprise a molar ratio of Formula (A): amine X of about 1:1, leading to approximately 100% cross-linking. In certain embodiments, the suitable conditions comprise a molar ratio of Formula (A): amine X of about 20:1, 10:1, 10:2, 10:3, 10:4, 6:1, 6:2, 6:3, 6:4, 6:5, or 1:1. In certain embodiments, the suitable conditions comprise a molar ratio of Formula (A): amine X of about 1:20, 1:10, 1:5, 1:3, 1:2, 20:1, 10:1, 10:2, 10:3, 10:4, 6:1, 6:2, 6:3, 6:4, 6:5, or 1:1. In certain embodiments, the suitable conditions comprise a molar ratio of Formula (A): amine X of about 10:1, 10:2, 10:3, 10:4, 6:1, 6:2, 6:3, 6:4, 6:5, or 1:1. In certain embodiments, the suitable conditions comprise a molar ratio of Formula (A): amine X of about 6:2. In certain embodiments, the suitable conditions comprise a molar ratio of Formula (A): amine X of about 5:2. In certain embodiments, the suitable conditions comprise a molar ratio of Formula (A): amine X of about 6:5. In certain embodiments, the suitable conditions comprise a molar ratio of Formula (A): amine X of about 5:1, 5:2, 5:3, 5:4, or 1:1. In certain embodiments, the suitable conditions comprise a molar ratio of Formula (A): amine X of about 5:3. In certain embodiments, the suitable conditions comprise a molar ratio of Formula (A): amine X of about 1:1. In certain embodiments, the suitable conditions comprise a molar ratio of Formula (A): amine X of about 1:1.5. In certain embodiments, the suitable conditions comprise a molar ratio of Formula (A): amine X of about 1.5:1. In certain embodiments, the suitable conditions comprise a molar ratio of Formula (A): amine X of about 3:1, 3:2, 3:2.5, 3:2.25, or 3:2.1. In certain embodiments, the suitable conditions comprise a molar ratio of Formula (A): amine X of about 2.0:1.5. In certain embodiments, the suitable conditions comprise a molar ratio of Formula (A): amine X of about 1:1, In certain embodiments, the suitable conditions comprise a molar ratio of Formula (A): Formula (B) of about 6:4. In certain embodiments, the suitable conditions comprise a molar ratio of Formula (A): Formula (B) of about 3:2. In certain embodiments, the suitable conditions comprise a molar ratio of Formula (A): Formula (B) of about 1:1, leading to approximately 100% cross-linking. In certain embodiments, the suitable conditions comprise a molar ratio of Formula (A): Formula (B) of about 20:1, 10:1, 10:2, 10:3, 10:4, 6:1, 6:2, 6:3, 6:4, 6:5, or 1:1. In certain embodiments, the suitable conditions comprise a molar ratio of Formula (A): Formula (B) of about 1:20, 1:10, 1:5, 1:3, 1:2, 20:1, 10:1, 10:2, 10:3, 10:4, 6:1, 6:2, 6:3, 6:4, 6:5, or 1:1. In certain embodiments, the suitable conditions comprise a molar ratio of Formula (A): Formula (B) of about 10:1, 10:2, 10:3, 10:4, 6:1, 6:2, 6:3, 6:4, 6:5, or 1:1. In certain embodiments, the suitable conditions comprise a molar ratio of Formula (A): Formula (B) of about 6:2. In certain embodiments, the suitable conditions comprise a molar ratio of Formula (A): Formula (B) of about 5:2. In certain embodiments, the suitable conditions comprise a molar ratio of Formula (A): Formula (B) of about 6:5. In certain embodiments, the suitable conditions comprise a molar ratio of Formula (A): Formula (B) of about 5:1, 5:2, 5:3, 5:4, or 1:1. In certain embodiments, the suitable conditions comprise a molar ratio of Formula (A): Formula (B) of about 5:3. In certain embodiments, the suitable conditions comprise a molar ratio of Formula (A): Formula (B) of about 1:1. In certain embodiments, the suitable conditions comprise a molar ratio of Formula (A): Formula (B) of about 1:1.5. In certain embodiments, the suitable conditions comprise a molar ratio of Formula (A): Formula (B) of about 1.5:1. In certain embodiments, the suitable conditions comprise a molar ratio of Formula (A): Formula (B) of about 3:1, 3:2, 3:2.5, 3:2.25, or 3:2.1. In certain embodiments, the suitable conditions comprise a molar ratio of Formula (A): Formula (B) of about 2.0:1.5. In certain embodiments, the suitable conditions comprise a molar ratio of Formula (A): Formula (B) of about 1:1.

In certain embodiments, the compound of Formula (A) is first dissolved in an aqueous solvent to achieve a solution of approximately 2.0-50.0% weight %, approximately 2.0-10.0% weight %, approximately 10.0-20.0% weight %, approximately 20.0-30.0% weight %, approximately 30.0-40.0% weight %, approximately 40.0-50.0% weight %, or approximately 5.0-30.0% weight %. In certain embodiments, the aqueous solvent is water. In certain embodiments, the compound of Formula (A) is first dissolved in water to achieve an approximately 5.0-30.0% weight % solution.

In certain embodiments, the compound of amine X is first diluted in an aqueous solvent to form an amine solution. In certain embodiments, the compound of amine X is first diluted in water to form an amine solution. In certain embodiments, the polymers of Formula (I) are synthesized by first preparing aqueous solutions of Formula (A) and amine X, combining the solutions of Formula (A) and amine X under suitable conditions for about 0.25 hours, about 0.5 hours, about 1 hour, about 1.25 hours, about 1.5 hours, about 2.0 hours, about 2.25 hours, about 2.5 hours, about 3.0 hours, about 4.0 hours, or about 5.0 hours. In certain embodiments, the polymers of Formula (I) are synthesized by first preparing aqueous solutions of Formula (A) and amine X, combining the solutions of Formula (A) and amine X under suitable conditions for about 0.25 hours, about 0.5 hours, about 1 hour, about 1.25 hours, about 1.5 hours, about 2.0 hours, about 2.25 hours, about 2.5 hours, about 3.0 hours, about 4.0 hours, or about 5.0 hours, and stirring In certain embodiments, the polymers of Formula (I) are synthesized by first preparing aqueous solutions of Formula (A) and amine X, combining the solutions of Formula (A) and amine X under suitable conditions for about 1 hour, and stirring.

In certain embodiments, the compound of Formula (B) is first diluted in an aqueous solvent to form an amine solution. In certain embodiments, the compound of Formula (B) is first diluted in water to form an amine solution. In certain embodiments, the polymers of Formula (I) are synthesized by first preparing aqueous solutions of Formula (A) and Formula (B), combining the solutions of Formula (A) and Formula (B) under suitable conditions for about 0.25 hours, about 0.5 hours, about 1 hour, about 1.25 hours, about 1.5 hours, about 2.0 hours, about 2.25 hours, about 2.5 hours, about 3.0 hours, about 4.0 hours, or about 5.0 hours. In certain embodiments, the polymers of Formula (I) are synthesized by first preparing aqueous solutions of Formula (A) and Formula (B), combining the solutions of Formula (A) and Formula (B) under suitable conditions for about 0.25 hours, about 0.5 hours, about 1 hour, about 1.25 hours, about 1.5 hours, about 2.0 hours, about 2.25 hours, about 2.5 hours, about 3.0 hours, about 4.0 hours, or about 5.0 hours, and stirring In certain embodiments, the polymers of Formula (I) are synthesized by first preparing aqueous solutions of Formula (A) and Formula (B), combining the solutions of Formula (A) and Formula (B) under suitable conditions for about 1 hour, and stirring.

In certain embodiments, the polymers of Formula (I) are synthesized by adding the components of the compound of Formula (A) with the compound of amine X together at room temperature for about 0.5-15.0 hours, about 0.5-1.0 hours, about 1-2 hours, about 2-3 hours, about 3-4 hours, about 4-5 hours, about 5-6 hours, about 6-7 hours, about 7-8 hours, about 8-9 hours, or about 9-10 hours. In certain embodiments, the polymers of Formula (I) are synthesized by adding the components of the compound of Formula (A) with the compound of amine X together at physiological temperature for about 0.5-15.0 hours, about 0.5-1.0 hours, about 1-2 hours, about 2-3 hours, about 3-4 hours, about 4-5 hours, about 5-6 hours, about 6-7 hours, about 7-8 hours, about 8-9 hours, or about 9-10 hours. In certain embodiments, the polymers of Formula (I) are synthesized by adding the components of the compound of Formula (A) with the compound of amine X together at room temperature for about 0.5-15.0 hours, about 0.5-1.0 hours, about 1-2 hours, about 2-3 hours, about 3-4 hours, about 4-5 hours, about 5-6 hours, about 6-7 hours, about 7-8 hours, about 8-9 hours, or about 9-10 hours. and stirring. In certain embodiments, the polymers of Formula (I) are synthesized by adding the components of the compound of Formula (A) with the compound of amine X together at room temperature for about 0.5-2.0 hours, and stirring. In certain embodiments, the polymers of Formula (I) are synthesized by adding the components of the compound of Formula (A) with the compound of amine X together at room temperature for about 1.0-2.0 hours, and stirring. In certain embodiments, the polymers of Formula (I) are synthesized by adding the components of the compound of Formula (A) with the compound of amine X together at room temperature for about 1.0-1.5 hours, and stirring. In certain embodiments, the polymers of Formula (I) are synthesized by adding the components of the compound of Formula (A) with the compound of amine X together at room temperature for about 1.0-1.25 hours, and stirring. In certain embodiments, the polymers of Formula (I) are synthesized by adding the components of the compound of Formula (A) with the compound of amine X together at room temperature for about 1.0 hour, and stirring.

In certain embodiments, the polymers of Formula (I) are synthesized by adding the components of the compound of Formula (A) with the compound of Formula (B) together at room temperature for about 0.5-15.0 hours, about 0.5-1.0 hours, about 1-2 hours, about 2-3 hours, about 3-4 hours, about 4-5 hours, about 5-6 hours, about 6-7 hours, about 7-8 hours, about 8-9 hours, or about 9-10 hours. In certain embodiments, the polymers of Formula (I) are synthesized by adding the components of the compound of Formula (A) with the compound of Formula (B) together at physiological temperature for about 0.5-15.0 hours, about 0.5-1.0 hours, about 1-2 hours, about 2-3 hours, about 3-4 hours, about 4-5 hours, about 5-6 hours, about 6-7 hours, about 7-8 hours, about 8-9 hours, or about 9-10 hours. In certain embodiments, the polymers of Formula (I) are synthesized by adding the components of the compound of Formula (A) with the compound of Formula (B) together at room temperature for about 0.5-15.0 hours, about 0.5-1.0 hours, about 1-2 hours, about 2-3 hours, about 3-4 hours, about 4-5 hours, about 5-6 hours, about 6-7 hours, about 7-8 hours, about 8-9 hours, or about 9-10 hours. and stirring. In certain embodiments, the polymers of Formula (I) are synthesized by adding the components of the compound of Formula (A) with the compound of Formula (B) together at room temperature for about 0.5-2.0 hours, and stirring. In certain embodiments, the polymers of Formula (I) are synthesized by adding the components of the compound of Formula (A) with the compound of Formula (B) together at room temperature for about 1.0-2.0 hours, and stirring. In certain embodiments, the polymers of Formula (I) are synthesized by adding the components of the compound of Formula (A) with the compound of Formula (B) together at room temperature for about 1.0-1.5 hours, and stirring. In certain embodiments, the polymers of Formula (I) are synthesized by adding the components of the compound of Formula (A) with the compound of Formula (B) together at room temperature for about 1.0-1.25 hours, and stirring. In certain embodiments, the polymers of Formula (I) are synthesized by adding the components of the compound of Formula (A) with the compound of Formula (B) together at room temperature for about 1.0 hour, and stirring.

In certain embodiments, the polymers of Formula (I) are synthesized by adding the components of the compound of Formula (A) with the compound of amine X together at about 37.0° C. for about 0.5-2.0 hours, and stirring. In certain embodiments, the polymers of Formula (I) are synthesized by adding the components of the compound of Formula (A) with the compound of amine X together at about 37.0° C. for about 1.0-2.0 hours, and stirring. In certain embodiments, the polymers of Formula (I) are synthesized by adding the components of the compound of Formula (A) with the compound of amine X together at about 37.0° C. for about 1.0-1.5 hours, and stirring. In certain embodiments, the polymers of Formula (I) are synthesized by adding the components of the compound of Formula (A) with the compound of amine X together at about 37.0° C. for about 1.0-1.25 hours, and stirring. In certain embodiments, the polymers of Formula (I) are synthesized by adding the components of the compound of Formula (A) with the compound of amine X together at about 37.0° C. for about 1.0 hour, and stirring. In certain embodiments, polymers of Formula (I) are synthesized according to the conditions described in Example 1 or Example 2. In certain embodiments, polymers of Formula (I) are synthesized under suitable conditions in situ in the body of the subject. In certain embodiments, polymers of Formula (I) are synthesized by adding the components of the compound of Formula (A) with the compound of amine X at physiological conditions in situ in the body of the subject. In certain embodiments, the polymers of Formula (I) are synthesized by adding the components of the compound of Formula (A) with the compound of Formula (B) together at about 37.0° C. for about 0.5-2.0 hours, and stirring. In certain embodiments, the polymers of Formula (I) are synthesized by adding the components of the compound of Formula (A) with the compound of Formula (B) together at about 37.0° C. for about 1.0-2.0 hours, and stirring. In certain embodiments, the polymers of Formula (I) are synthesized by adding the components of the compound of Formula (A) with the compound of Formula (B) together at about 37.0° C. for about 1.0-1.5 hours, and stirring. In certain embodiments, the polymers of Formula (I) are synthesized by adding the components of the compound of Formula (A) with the compound of Formula (B) together at about 37.0° C. for about 1.0-1.25 hours, and stirring. In certain embodiments, the polymers of Formula (I) are synthesized by adding the components of the compound of Formula (A) with the compound of Formula (B) together at about 37.0° C. for about 1.0 hour, and stirring. In certain embodiments, polymers of Formula (I) are synthesized according to the conditions described in Example 1 or Example 2. In certain embodiments, polymers of Formula (I) are synthesized under suitable conditions in situ in the body of the subject. In certain embodiments, polymers of Formula (I) are synthesized by adding the components of the compound of Formula (A) with the compound of Formula (B) at physiological conditions in situ in the body of the subject. In certain embodiments, the polymers of Formula (I) are synthesized under suitable conditions, which involve any combination of the reaction conditions, reaction temperatures, ratios of starting materials, and/or stoichiometries of starting materials.

In certain embodiments, the tetra-arm polyethylene glycol alkynoate compound of Formula (A) is prepared under suitable conditions. In certain embodiments, the reaction for preparing the compound of Formula (A) is a Dean-Star Fischer esterification. In certain embodiments, the reaction for preparing the compound of Formula (A) is a Dean-Star Fischer esterification performed by dissolving tetra-arm PEG-OH in solvent, adding one or more types of acid, refluxing with excess of the solvent, and cooling. In certain embodiments, the tetra-arm PEG-OH has an average molecular weight ($M_n$) of 5,000 g. In certain embodiments, the tetra-arm PEG-OH has an average molecular weight ($M_n$) of 10,000 g. In certain embodiments, the tetra-arm PEG-OH has an average molecular weight ($M_n$) of 15,000 g. In certain embodiments, the tetra-arm PEG-OH has an average molecular weight ($M_n$) of 20,000 g. In certain embodiments, the tetra-arm PEG-OH has an average molecular weight ($M_n$) of 25,000 g. In certain embodiments, the reaction for preparing the compound of Formula (A) is a Dean-Star Fischer esterification performed by dissolving tetra-arm PEG-OH in toluene, adding propiolic acid and para-toluenesulfonic acid, refluxing under Dean-Stark conditions using an excess of toluene in the trap and a trap; followed by cooling to room temperature; and optionally, isolation. In certain embodiments, the tetra-arm polyethylene glycol alkynoate compound of Formula (A) is prepared according to the conditions described in Example 1 or Example 2. In certain embodiments, the tetra-arm PEG-OH is monodisperse, and in Formulae (I) or (I-Z), approximately 50-90%, approximately 60-90%, approximately 70-90%, approximately 80-90%, or approximately 90-100%, of the instances of n are between 5-200, 100-200, 5-100, 15-100, 10-100, 15-100, or 15-150. In certain embodiments, the tetra-arm PEG-OH is highly monodisperse with approximately 70-90%, approximately 80-90%, or approximately 90-100%, of the instances of n are between 5-200, 100-200, 5-100, 15-100, 10-100, 15-100, or 15-150.

In certain embodiments, the tetra-arm PEG-OH is polydisperse, and in Formulae (I) or (I-Z), approximately 40-50%, approximately 50-60%, or approximately 60-70%, of the instances of n are between 5-200, 100-200, 5-100, 15-100, 10-100, 15-100, or 15-150. In certain embodiments, the tetra-arm PEG-OH is highly polydisperse, and in Formulae (I) or (I-Z), approximately 10-20%, approximately 20-30%, or approximately 30-40%, of the instances of n are between 5-200, 100-200, 5-100, 15-100, 10-100, 15-100, or 15-150.

Methods of Use and Uses

The present disclosure also provides methods of using the polymers described herein, or compositions (e.g., pharmaceutical compositions) or formulations thereof, for delivering an agent (e.g., a small molecule, biologic), cosmetic agent, diagnostic agent, prophylactic agent)) to a subject or to a biological sample (e.g., cell, tissue), as part of a material (e.g., a biodegradable or biocompatible material; wound dressing (e.g., bandages)), drug depots, coatings, or as a biomaterial (e.g., as a scaffold for tissue engineering). Provided herein are methods of using the polymers described herein, or compositions (e.g., pharmaceutical compositions) or formulations thereof, wherein the composition optionally comprises water, and comprises an agent (e.g., a small molecule, biologic), cosmetic agent, diagnostic agent, prophylactic agent)). Provided herein are methods of delivering the polymers described herein, or compositions (e.g., pharmaceutical compositions) or formulations thereof, wherein the composition optionally comprises water, and comprises A therapeutic agent (e.g., a small molecule, nucleic acid, protein, peptide, polynucleotide, biologic), cosmetic agent, diagnostic agent, and/or prophylactic agent)) to a subject, cell, tissue, or biological sample. In certain embodiments, the agent is a cosmetic agent. In certain embodiments, the agent is a diagnostic agent. In certain embodiments, the agent is an imaging agent. In certain embodiments, the agent is a prophylactic agent. In certain embodiments, the agent is a therapeutic agent. In certain embodiments, the therapeutic agent is an antigen, antibody, or a vaccine. In certain embodiments, the therapeutic agent is a biologic (e.g., a protein). In certain embodiments, the therapeutic agent is a small molecule. In certain embodiments, the therapeutic agent is a prodrug of a small molecule. In certain embodiments, the small molecule is an antibiotic, anesthetic, steroidal agent, anti-proliferative agent, anti-inflammatory agent, anti-angiogenesis agent, anti-neoplastic agent, anti-cancer agent, anti-diabetic agent, decongestant, antihypertensive, sedative, anti-cholinergic, analgesic, immunosuppressant, anti-depressant, anti-psychotic, β-adrenergic blocking agent, diuretic, cardiovascular active agent, vasoactive agent, non-steroidal, nutritional agent, anti-allergic agent, or pain-relieving agent.

In certain embodiments, the anti-inflammatory agent is an agent for treating an acute inflammatory disease (e.g., rheumatoid arthritis, Crohn's disease, or fibrosis). In certain embodiments, the anti-inflammatory agent is an agent for treating an autoinflammatory disease. In certain embodiments, the anti-inflammatory agent is an agent for treating an autoimmune disease. In certain embodiments, the anti-cancer agent is an anti-leukemia agent. In certain embodiments, the anti-cancer agent is ABITREXATE (methotrexate), ADE, Adriamycin RDF (doxorubicin hydrochloride), Ambochlorin (chlorambucil), ARRANON (nelarabine), ARZERRA (ofatumumab), BOSULIF (bosutinib), BUSULFEX (busulfan), CAMPATH (alemtuzumab), CERUBIDINE (daunorubicin hydrochloride), CLAFEN (cyclophosphamide), CLOFAREX (clofarabine), CLOLAR (clofarabine), CVP, CYTOSAR-U (cytarabine), CYTOXAN (cyclophosphamide), ERWINAZE (Asparaginase Erwinia Chrysanthemi), FLUDARA (fludarabine phosphate), FOLEX (methotrexate), FOLEX PFS (methotrexate), GAZYVA (obinutuzumab), GLEEVEC (imatinib mesylate), Hyper-CVAD, ICLUSIG (ponatinib hydrochloride), IMBRUVICA (ibrutinib), LEUKERAN (chlorambucil), LINFOLIZIN (chlorambucil), MARQIBO (vincristine sulfate liposome), METHOTREXATE LPF (methorexate), MEXATE (methotrexate), MEXATE-AQ (methotrexate), mitoxantrone hydrochloride, MUSTARGEN (mechlorethamine hydrochloride), MYLERAN (busulfan), NEOSAR (cyclophosphamide), ONCASPAR (Pegaspargase), PURINETHOL (mercaptopurine), PURIXAN (mercaptopurine), Rubidomycin (daunorubicin hydrochloride), SPRYCEL (dasatinib), SYNRIBO (omacetaxine mepesuccinate), TARABINE PFS (cytarabine), TASIGNA (nilotinib), TREANDA (bendamustine hydrochloride), TRISENOX (arsenic trioxide), VINCASAR PFS (vincristine sulfate), ZYDELIG (idelalisib), or a combination thereof. In certain embodiments, the additional pharmaceutical agent is an anti-lymphoma agent. In certain embodiments, the additional pharmaceutical agent is ABITREXATE (methotrexate), ABVD, ABVE, ABVE-PC, ADCETRIS (brentuximab vedotin), ADRIAMYCIN PFS (doxorubicin hydrochloride), ADRIAMYCIN RDF (doxorubicin hydrochloride), AMBOCHLORIN (chlorambucil), AMBOCLORIN (chlorambucil), ARRANON (nelarabine), BEACOPP, BECENUM (carmustine), BELEODAQ (belinostat), BEXXAR (tositumomab and iodine I 131 tositumomab), BICNU (carmustine), BLENOXANE (bleomycin), CARMUBRIS (carmustine), CHOP, CLAFEN (cyclophosphamide), COPP, COPP-ABV, CVP, CYTOXAN (cyclophosphamide), DEPOCYT (liposomal cytarabine), DTIC-DOME (dacarbazine), EPOCH, FOLEX (methotrexate), FOLEX PFS (methotrexate), FOLOTYN (pralatrexate), HYPER-CVAD, ICE, IMBRUVICA (ibrutinib), INTRON A (recombinant interferon alfa-2b), ISTODAX (romidepsin), LEUKERAN (chlorambucil), LINFOLIZIN (chlorambucil), Lomustine, MATULANE (procarbazine hydrochloride), METHOTREXATE LPF (methotrexate), MEXATE (methotrexate), MEXATE-AQ (methotrexate), MOPP, MOZOBIL (plerixafor), MUSTARGEN (mechlorethamine hydrochloride), NEOSAR (cyclophosphamide), OEPA, ONTAK (denileukin diftitox), OPPA, R-CHOP, REVLIMID (lenalidomide), RITUXAN (rituximab), STANFORD V, TREANDA (bendamustine hydrochloride), VAMP, VELBAN (vinblastine sulfate), VELCADE (bortezomib), VELSAR (vinblastine sulfate), VINCASAR PFS (vincristine sulfate), ZEVALIN (ibritumomab tiuxetan), ZOLINZA (vorinostat), ZYDELIG (idelalisib), or a combination thereof. In certain embodiments, the additional pharmaceutical agent is REVLIMID (lenalidomide), DACOGEN (decitabine), VIDAZA (azacitidine), CYTOSAR-U (cytarabine), IDAMYCIN (idarubicin), CERUBIDINE (daunorubicin), LEUKERAN (chlorambucil), NEOSAR (cyclophosphamide), FLUDARA (fludarabine), LEUSTATIN (cladribine), or a combination thereof. In certain embodiments, the additional pharmaceutical agent is ABITREXATE (methotrexate), ABRAXANE (paclitaxel albumin-stabilized nanoparticle formulation), AC, AC-T, ADE, ADRIAMYCIN PFS (doxorubicin hydrochloride), ADRUCIL (fluorouracil), AFINITOR (everolimus), AFINITOR DISPERZ (everolimus), ALDARA (imiquimod), ALIMTA (pemetrexed disodium), AREDIA (pamidronate disodium), ARIMIDEX (anastrozole), AROMASIN (exemestane), AVASTIN (bevacizumab), BECENUM (carmustine), BEP, BICNU (carmustine), BLENOXANE (bleomycin), CAF, CAMPTOSAR (irinotecan hydrochloride), CAPDX, CAPRELSA (vandetanib), CARBOPLATIN-TAXOL, CARMUBRIS (carmustine), CASODEX (bicalutamide), CEENU (lomustine), CERUBIDINE (daunorubicin hydrochloride), CERVARIX (recombinant HPV bivalent vaccine), CLAFEN (cyclophosphamide), CMF, COMETRIQ (cabozantinib-s-malate), COSMEGEN (dactinomycin), CYFOS (ifosfamide), CYRAMZA (ramucirumab), CYTOSAR-U (cytarabine), CYTOXAN (cyclophosphamide), DACOGEN (decitabine), DEGARELIX, DOXIL (doxorubicin hydrochloride liposome), DOXORUBICIN HYDROCHLORIDE, DOX-SL (doxorubicin hydrochloride liposome), DTIC-DOME (dacarbazine), EFUDEX (fluorouracil), ELLENCE (epirubicin hydrochloride), ELOXATIN (oxaliplatin), ERBITUX (cetuximab), ERIVEDGE (vismodegib), ETOPOPHOS (etoposide phosphate), EVACET (doxorubicin hydrochloride liposome), FARESTON (toremifene), FASLODEX (fulvestrant), FEC, FEMARA (letrozole), FLUOROPLEX (fluorouracil), FOLEX (methotrexate), FOLEX PFS (methotrexate), FOLFI, FOLFIRI-BEVACIZUMAB, FOLFIRI-CETUXIMAB, FOLFIRINOX, FOLFOX, FU-LV, GARDASIL (recombinant human papillomavirus (HPV)

quadrivalent vaccine), GEMCITABINE-CISPLATIN, GEMCITABINE-OXALIPLATIN, GEMZAR (gemcitabine hydrochloride), GILOTRIF (afatinib dimaleate), GLEEVEC (imatinib mesylate), GLIADEL (carmustine implant), GLIADEL WAFER (carmustine implant), HERCEPTIN (trastuzumab), HYCAMTIN (topotecan hydrochloride), IFEX (ifosfamide), IFOSFAMIDUM (ifosfamide), INLYTA (axitinib), INTRON A (recombinant interferon alfa-2b), IRESSA (gefitinib), IXEMPRA (ixabepilone), JAKAFI (ruxolitinib phosphate), JEVTANA (cabazitaxel), KADCYLA (ado-trastuzumab emtansine), KEYTRUDA (pembrolizumab), KYPROLIS (carfilzomib), LIPODOX (doxorubicin hydrochloride liposome), LUPRON (leuprolide acetate), LUPRON DEPOT (leuprolide acetate), LUPRON DEPOT-3 MONTH (leuprolide acetate), LUPRON DEPOT-4 MONTH (leuprolide acetate), LUPRON DEPOT-PED (leuprolide acetate), MEGACE (megestrol acetate), MEKINIST (trametinib), METHAZOLASTONE (temozolomide), METHOTREXATE LPF (methotrexate), MEXATE (methotrexate), MEXATE-AQ (methotrexate), MITOXANTRONE HYDROCHLORIDE, MITOZYTREX (mitomycin c), MOZOBIL (plerixafor), MUSTARGEN (mechlorethamine hydrochloride), MUTAMYCIN (mitomycin c), MYLOSAR (azacitidine), NAVELBINE (vinorelbine tartrate), NEOSAR (cyclophosphamide), NEXAVAR (sorafenib tosylate), NOLVADEX (tamoxifen citrate), NOVALDEX (tamoxifen citrate), OFF, PAD, PARAPLAT (carboplatin), PARAPLATIN (carboplatin), PEG-INTRON (peginterferon alfa-2b), PEMETREXED DISODIUM, PERJETA (pertuzumab), PLATINOL (cisplatin), PLATINOL-AQ (cisplatin), POMALYST (pomalidomide), prednisone, PROLEUKIN (aldesleukin), PROLIA (denosumab), PROVENGE (sipuleucel-t), REVLIMID (lenalidomide), RUBIDOMYCIN (daunorubicin hydrochloride), SPRYCEL (dasatinib), STIVARGA (regorafenib), SUTENT (sunitinib malate), SYLATRON (peginterferon alfa-2b), SYLVANT (siltuximab), SYNOVIR (thalidomide), TAC, TAFINLAR (dabrafenib), TARABINE PFS (cytarabine), TARCEVA (erlotinib hydrochloride), TASIGNA (nilotinib), TAXOL (paclitaxel), TAXOTERE (docetaxel), TEMODAR (temozolomide), THALOMID (thalidomide), TOPOSAR (etoposide), TORISEL (temsirolimus), TPF, TRISENOX (arsenic trioxide), TYKERB (lapatinib ditosylate), VECTIBIX (panitumumab), VEIP, VELBAN (vinblastine sulfate), VELCADE (bortezomib), VELSAR (vinblastine sulfate), VEPESID (etoposide), VIADUR (leuprolide acetate), VIDAZA (azacitidine), VINCASAR PFS (vincristine sulfate), VOTRIENT (pazopanib hydrochloride), WELLCOVORIN (leucovorin calcium), XALKORI (crizotinib), XELODA (capecitabine), XELOX, XGEVA (denosumab), XOFIGO (radium 223 dichloride), XTANDI (enzalutamide), YERVOY (ipilimumab), ZALTRAP (ziv-aflibercept), ZELBORAF (vemurafenib), ZOLADEX (goserelin acetate), ZOMETA (zoledronic acid), ZYKADIA (ceritinib), ZYTIGA (abiraterone acetate), ENMD-2076, PCI-32765, AC220, dovitinib lactate (TKI258, CHIR-258), BMW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (Velcade)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin-aminopterin, and hexamethyl melamine, or a combination thereof. In certain embodiments, the additional pharmaceutical agent is ibrutinib. In certain embodiments, the small molecule (e.g., small molecule therapeutic agent) is an anti-cancer agent (e.g., taxane). In certain embodiments, the anti-cancer agent is an agent for treating breast cancer. In certain embodiments, the anti-cancer agent is a taxane. In certain embodiments, the taxane is docetaxel. In certain embodiments, the taxane is paclitaxel. In certain embodiments, the taxane is cabazitaxel. In certain embodiments, the taxane is abraxane. In certain embodiments, the taxane is taxotere. In certain embodiments, the anti-cancer agent is an anthracycline (e.g., doxorubicin, epirubicin). In certain embodiments, the anti-cancer agent is an alkylating agent (e.g., a cytoxan).

In certain embodiments, the small molecule is a "small molecule label." The term "small molecule label" refers to a small molecule that is capable of being detected, or a radical of such a small molecule. Exemplary small molecule labels include, but are not limited to, biotin, radioactive isotopes, enzymes, luminescent agents, precipitating agents, fluorophores, and dyes. In certain embodiments, the small molecule label is a tag (e.g., a biotin derivative, radiometric label, or fluorophore). In certain embodiments, the small molecule is a fluorophore (e.g., a Cy5.5). In certain embodiments, the fluorophore is a non-protein, organic fluorophore (e.g., a derivative of xanthine, cyanine, squaraine rotaxane, naphthalene, coumarin, oxadiazole, anthracene, pyrene, oxazine, acridine, arylmethine, tetrapyrrole).

In certain embodiments, the fluorophore is a cyanine fluorophore. In certain embodiments, the fluorophore is a cyanine derivative fluorophore. In certain embodiments, the fluorophore is Cy3.5. In certain embodiments, the fluorophore is Cy5. In certain embodiments, the fluorophore is Cy5.5.

Provided herein are methods of using the polymers described herein, or compositions (e.g., pharmaceutical, cosmetic, diagnostic, prophylactic compositions) or formulations thereof, as a biomaterial (e.g., as scaffolds for tissue engineering). In certain embodiments, the polymers are used in human applications (e.g., medical, industrial, research uses). In certain embodiments, the composition is used in non-human veterinary applications (e.g., used for non-human animals (e.g., farm animals, companion animals)).

In certain embodiments, the polymers are used in human applications. In certain embodiments, the polymers are used in human medical applications. In certain embodiments, the polymers are used in human surgical applications. In certain embodiments, the polymers are used in topical applications. In certain embodiments, the polymers comprise or are part of a bandage. In certain embodiments, the polymers comprise a liquid spray-on bandage. In certain embodiments, the polymers comprise a liquid spray-on bandage, in which the bandage forms into a gel on the skin of the subject once the liquid components of the polymers described herein are sprayed onto the skin.

In certain embodiments, polymers are used in or are part of a viscoelastic bandage. In certain embodiments, polymers are used in an intraoperative setting (e.g., laparascopic or open surgical setting). In certain embodiments, polymers are used to prevent peritoneal adhesion. In certain embodiments, polymers are used in an intraoperative setting to prevent post-operative peritoneal adhesion. In certain embodiments, polymers are applied to tissue at risk of a peritoneal adhesion after surgery, in an intraoperative setting to prevent post-operative peritoneal adhesion. In certain embodiments, the polymers described herein are used for delivering one or more pharmaceutical agents to the peritoneum to prevent a peritoneal adhesion. In certain embodiments, the polymers described herein are used as part of a drug depot used in an intraoperative setting, and implanted during surgery. In certain embodiments, one or more pharmaceutical agents are mixed with polymers described herein, and injected into a subject for later extended release of the one or more pharmaceutical agents during surgery. In certain embodiments, polymers described herein are combined with a medical device implant for supporting the implant. In certain embodiments, the medical device implant is an orthopedic implant. In certain embodiments, polymers described herein are used as a surgical mesh. In certain embodiments, polymers described herein are used as a surgical mesh, wherein the pore size of the mesh is less than 1 mm. In certain embodiments, polymers described herein are used as a tissue adhesive during surgery. In certain embodiments, polymers described herein are used as biomaterial scaffolds for ligament and/or tendon repair, implanted during surgery. In certain embodiments, polymers described herein are used as supports for installing vascular stents and/or vascular grafts, and are implanted during surgery. In certain embodiments, polymers described herein are used as supports for installing implants during plastic, cosmetic, and/or reconstructive surgery. In certain embodiments, polymers described herein are used as composites in dental surgery. In certain embodiments, polymers described herein are used as composites in dental surgery, in combination with an inorganic filler with particle size in nanometers or micrometers.

In certain embodiments, polymers described herein are delivered to a subject orally, rectally, parenterally, intracisternally, intravaginally, intranasally, intraperitoneally, topically (as by powders, creams, ointments, or drops), bucally, or as an oral or nasal spray. In certain embodiments, polymers described herein are delivered by topical delivery. In certain embodiments, polymers described herein are delivered by ocular delivery. In certain embodiments, the ocular delivery comprises delivery to the front of the eye. In certain embodiments, the ocular delivery comprises delivery to the back of the eye.

In certain embodiments, polymers described herein are used in scaffolds for tissue engineering that comprise cells, growth factors, proteins, peptides, nucleic acids, small molecules, nutrients, saccharides, and/or cell binding domains (e.g., protein domains, sugars, amino acids, vitamins, minerals). In certain embodiments, saccharides comprise multiple saccharide units (e.g., polysaccharides, oligosaccharides). In certain embodiments, the scaffolds for tissue engineering comprise cells. In certain embodiments, the cells comprise nonadherent cells. In certain embodiments, the cells comprise adherent cells. In certain embodiments, the cells are mammalian cells. In certain embodiments, the cells comprise human cells. In certain embodiments, the cells comprise human cells. In certain embodiments, the cells comprise human monocyte cells. In certain embodiments, the cells comprise autologous, allogeneic, xenogenic, syngenic, primary, secondary cells, or stem cells. In certain embodiments, the cells comprise myocytes, endothelial cells, nerve cells, or epithelial cells. In certain embodiments, the cells comprise cancer cells. In certain embodiments, the cells comprise leukemia cells. In certain embodiments, the cells comprise human leukemia monocyte cells. In certain embodiments, the cells comprise embryonic stem cells, bone marrow-derived mesenchymal stem cells, or cord-derived mesenchymal stem cells. In certain embodiments, the cells comprise stem cells and/or progenitor cells. In certain embodiments, the cells comprise THP-1 cells. In certain embodiments, the cells comprise mouse cells. In certain embodiments, the cells comprise connective tissue cells. In certain embodiments, the cells comprise fibroblast cells. In certain embodiments, the cells comprise NIH/3T3 cells. In certain embodiments, the scaffolds for tissue engineering comprise growth factors. In certain embodiments, the scaffolds for tissue engineering comprise peptides. In certain embodiments, the scaffolds for tissue engineering comprise cell binding domains. In certain embodiments, the scaffolds for tissue engineering comprise collagen, laminin, or fibronectin. In certain embodiments, the scaffolds for tissue engineering comprise the RGD motif of fibronectin.

In certain embodiments, polymers described herein are used as a tissue adhesive. In certain embodiments, polymers described herein are used as scaffolds for orthopedic implants. In certain embodiments, polymers described herein are used as biomaterial scaffolds for ligament and/or tendon repair. In certain embodiments, polymers described herein are used as supports for installing vascular stents and/or vascular grafts. In certain embodiments, polymers described herein are used as composites in dentistry. In certain embodiments, polymers described herein are used for nerve guidance conduits.

The present disclosure also provides methods of using the polymers described herein, in compositions (e.g., pharmaceutical compositions (e.g., sustained-release, controlled-release formulations), cosmetic compositions, nutraceutical compositions). The present disclosure also provides methods of using the polymers described herein, in compositions (e.g., pharmaceutical compositions (e.g., sustained-release, controlled-release formulations), cosmetic compositions, nutraceutical compositions), for delivering an agent (e.g., a therapeutic agent (e.g., a small molecule, nucleic acid, protein, peptide, polynucleotide, biologic), cosmetic agent, diagnostic agent, and/or prophylactic agent), cosmetic agent, diagnostic agent, prophylactic agent)) to a subject or to a biological sample (e.g., cell, tissue). In certain embodiments, the controlled-release and/or sustained-release formulations release the therapeutic agent. In certain embodiments, the released therapeutic agent is an anti-cancer agent. In certain embodiments, the anti-cancer agent is an anti-leukemia agent. In certain embodiments, the anti-cancer agent is ABITREXATE (methotrexate), ADE, Adriamycin RDF (doxorubicin hydrochloride), Ambochlorin (chlorambucil), ARRANON (nelarabine), ARZERRA (ofatumumab), BOSULIF (bosutinib), BUSULFEX (busulfan), CAMPATH (alemtuzumab), CERUBIDINE (daunorubicin hydrochloride), CLAFEN (cyclophosphamide), CLOFAREX (clofarabine), CLOLAR (clofarabine), CVP, CYTOSAR-U (cytarabine), CYTOXAN (cyclophosphamide), ERWINAZE (Asparaginase Erwinia Chrysanthemi), FLUDARA (fludarabine phosphate), FOLEX (methotrexate), FOLEX PFS (methotrexate), GAZYVA (obinutuzumab), GLEEVEC (imatinib mesylate), Hyper-CVAD, ICLUSIG (ponatinib hydrochloride), IMBRUVICA (ibrutinib), LEUKERAN (chlorambucil), LINFOLIZIN (chlorambucil), MARQIBO (vincristine sulfate liposome), METHOTREXATE LPF (methorexate), MEXATE (methotrexate), MEXATE-AQ (methotrexate), mitoxantrone hydrochloride, MUSTARGEN (mechlorethamine hydrochloride), MYLERAN (busulfan), NEOSAR (cyclophosphamide), ONCASPAR (Pegaspargase), PURINETHOL (mercaptopurine), PURIXAN (mercaptopurine), Rubidomycin (daunorubicin hydrochloride), SPRYCEL (dasatinib), SYNRIBO (omacetaxine mepesuccinate), TARABINE PFS (cytarabine), TASIGNA (nilotinib), TREANDA (bendamustine hydrochloride), TRISENOX (arsenic trioxide), VINCASAR PFS (vincristine sulfate), ZYDELIG (idelalisib), or a combination thereof. In certain embodiments, the additional pharmaceutical agent is an anti-lymphoma agent. In certain embodiments, the additional pharmaceutical agent is ABITREXATE (methotrexate), ABVD, ABVE, ABVE-PC, ADCETRIS (brentuximab vedotin), ADRIAMYCIN PFS (doxorubicin hydrochloride), ADRIAMYCIN RDF (doxorubicin hydrochloride), AMBOCHLORIN (chlorambucil), AMBOCLORIN (chlorambucil), ARRANON (nelarabine), BEACOPP, BECENUM (carmustine), BELEODAQ (belinostat), BEXXAR (tositumomab and iodine I 131 tositumomab), BICNU (carmustine), BLENOXANE (bleomycin), CARMUBRIS (carmustine), CHOP, CLAFEN (cyclophosphamide), COPP, COPP-ABV, CVP, CYTOXAN (cyclophosphamide), DEPOCYT (liposomal cytarabine), DTIC-DOME (dacarbazine), EPOCH, FOLEX (methotrexate), FOLEX PFS (methotrexate), FOLOTYN (pralatrexate), HYPER-CVAD, ICE, IMBRUVICA (ibrutinib), INTRON A (recombinant interferon alfa-2b), ISTODAX (romidepsin), LEUKERAN (chlorambucil), LINFOLIZIN (chlorambucil), Lomustine, MATULANE (procarbazine hydrochloride), METHOTREXATE LPF (methotrexate), MEXATE (methotrexate), MEXATE-AQ (methotrexate), MOPP, MOZOBIL (plerixafor), MUSTARGEN (mechlorethamine hydrochloride), NEOSAR (cyclophosphamide), OEPA, ONTAK (denileukin diftitox), OPPA, R-CHOP, REVLIMID (lenalidomide), RITUXAN (rituximab), STANFORD V, TREANDA (bendamustine hydrochloride), VAMP, VELBAN (vinblastine sulfate), VELCADE (bortezomib), VELSAR (vinblastine sulfate), VINCASAR PFS (vincristine sulfate), ZEVALIN (ibritumomab tiuxetan), ZOLINZA (vorinostat), ZYDELIG (idelalisib), or a combination thereof. In certain embodiments, the additional pharmaceutical agent is REVLIMID (lenalidomide), DACOGEN (decitabine), VIDAZA (azacitidine), CYTOSAR-U (cytarabine), IDAMYCIN (idarubicin), CERUBIDINE (daunorubicin), LEUKERAN (chlorambucil), NEOSAR (cyclophosphamide), FLUDARA (fludarabine), LEUSTATIN (cladribine), or a combination thereof. In certain embodiments, the additional pharmaceutical agent is ABITREXATE (methotrexate), ABRAXANE (paclitaxel albumin-stabilized nanoparticle formulation), AC, AC-T, ADE, ADRIAMYCIN PFS (doxorubicin hydrochloride), ADRUCIL (fluorouracil), AFINITOR (everolimus), AFINITOR DISPERZ (everolimus), ALDARA (imiquimod), ALIMTA (pemetrexed disodium), AREDIA (pamidronate disodium), ARIMIDEX (anastrozole), AROMASIN (exemestane), AVASTIN (bevacizumab), BECENUM (carmustine), BEP, BICNU (carmustine), BLENOXANE (bleomycin), CAF, CAMPTOSAR (irinotecan hydrochloride), CAPDX, CAPRELSA (vandetanib), CARBOPLATIN-TAXOL, CARMUBRIS (carmustine), CASODEX (bicalutamide), CEENU (lomustine), CERUBIDINE (daunorubicin hydrochloride), CERVARIX (recombinant HPV bivalent vaccine), CLAFEN (cyclophosphamide), CMF, COMETRIQ (cabozantinib-s-malate), COSMEGEN (dactinomycin), CYFOS (ifosfamide), CYRAMZA (ramucirumab), CYTOSAR-U (cytarabine), CYTOXAN (cyclophosphamide), DACOGEN (decitabine), DEGARELIX, DOXIL (doxorubicin hydrochloride liposome), DOXORUBICIN HYDROCHLORIDE, DOX-SL (doxorubicin hydrochloride liposome), DTIC-DOME (dacarbazine), EFUDEX (fluorouracil), ELLENCE (epirubicin hydrochloride), ELOXATIN (oxaliplatin), ERBITUX (cetuximab), ERIVEDGE (vismodegib), ETOPOPHOS (etoposide phosphate), EVACET (doxorubicin hydrochloride liposome), FARESTON (toremifene), FASLODEX (fulvestrant), FEC, FEMARA (letrozole), FLUOROPLEX (fluorouracil), FOLEX (methotrexate), FOLEX PFS (methotrexate), FOLFIRI, FOLFIRI-BEVACIZUMAB, FOLFIRI-CETUXIMAB, FOLFIRINOX, FOLFOX, FU-LV, GARDASIL (recombinant human papillomavirus (HPV) quadrivalent vaccine), GEMCITABINE-CISPLATIN, GEMCITABINE-OXALIPLATIN, GEMZAR (gemcitabine hydrochloride), GILOTRIF (afatinib dimaleate), GLEEVEC (imatinib mesylate), GLIADEL (carmustine implant), GLIADEL WAFER (carmustine implant), HERCEPTIN (trastuzumab), HYCAMTIN (topotecan hydrochloride), IFEX (ifosfamide), IFOSFAMIDUM (ifosfamide), INLYTA (axitinib), INTRON A (recombinant interferon alfa-2b), IRESSA (gefitinib), IXEMPRA (ixabepilone), JAKAFI (ruxolitinib phosphate), JEVTANA (cabazitaxel), KADCYLA (ado-trastuzumab emtansine), KEYTRUDA (pembrolizumab), KYPROLIS (carfilzomib), LIPODOX (doxorubicin hydrochloride liposome), LUPRON (leuprolide acetate), LUPRON DEPOT (leuprolide acetate), LUPRON DEPOT-3 MONTH (leuprolide acetate), LUPRON DEPOT-4 MONTH (leuprolide acetate), LUPRON DEPOT-PED (leuprolide acetate), MEGACE (megestrol acetate), MEKINIST (trametinib), METHAZOLASTONE (temozolomide), METHOTREXATE LPF (methotrexate), MEXATE (methotrexate), MEXATE-AQ (methotrexate), MITOXANTRONE HYDROCHLORIDE, MITOZYTREX (mitomycin c), MOZOBIL (plerixafor), MUSTARGEN (mechlorethamine hydrochloride), MUTAMYCIN (mitomycin c), MYLOSAR (azacitidine), NAVELBINE (vinorelbine tartrate), NEOSAR (cyclophosphamide), NEXAVAR (sorafenib tosylate), NOLVADEX (tamoxifen citrate), NOVALDEX (tamoxifen citrate), OFF, PAD, PARAPLAT (carboplatin), PARAPLATIN (carboplatin), PEG-INTRON (peginterferon alfa-2b), PEMETREXED DISODIUM, PERJETA (pertuzumab), PLATINOL (cisplatin), PLATINOL-AQ (cisplatin), POMALYST (pomalidomide), prednisone, PROLEUKIN (aldesleukin), PROLIA (denosumab), PROVENGE (sipuleucel-t), REVLIMID (lenalidomide), RUBIDOMYCIN (daunorubicin hydrochloride), SPRYCEL (dasatinib), STIVARGA (regorafenib), SUTENT (sunitinib malate), SYLATRON (peginterferon alfa-2b), SYLVANT (siltuximab), SYNOVIR (thalidomide), TAC, TAFINLAR (dabrafenib), TARABINE PFS (cytarabine), TARCEVA (erlotinib hydrochloride), TASIGNA (nilotinib), TAXOL (paclitaxel), TAXOTERE (docetaxel), TEMODAR (temozolomide), THALOMID (thalidomide), TOPOSAR (etoposide), TORISEL (temsirolimus), TPF, TRISENOX (arsenic trioxide), TYKERB (lapatinib ditosylate), VECTIBIX (panitumumab), VEIP, VELBAN (vinblastine sulfate), VELCADE (bortezomib), VELSAR (vinblastine sulfate), VEPESID (etoposide), VIADUR (leuprolide acetate), VIDAZA (azacitidine), VINCASAR PFS (vincristine sulfate), VOTRIENT (pazopanib hydrochloride), WELLCOVORIN (leucovorin calcium), XALKORI (crizotinib), XELODA (capecitabine), XELOX, XGEVA (denosumab), XOFIGO (radium 223 dichloride), XTANDI (enzalutamide), YERVOY (ipilimumab), ZALTRAP (ziv-aflibercept), ZELBORAF (vemurafenib), ZOLADEX (goserelin acetate), ZOMETA (zoledronic acid), ZYKADIA (ceritinib), ZYTIGA (abiraterone acetate), ENMD-2076, PCI-32765, AC220, dovitinib lactate (TKI258, CHIR-258), BMW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (Velcade)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin-aminopterin, and hexamethyl melamine, or a combination thereof. In certain embodiments, the additional pharmaceutical agent is ibrutinib. In certain embodiments, the anti-cancer agent is an agent for treating breast cancer. In certain embodiments, the anti-cancer agent is a taxane. In certain embodiments, the taxane is docetaxel. In certain embodiments, the taxane is paclitaxel. In certain embodiments, the taxane is cabazitaxel. In certain embodiments, the taxane is abraxane. In certain embodiments, the taxane is taxotere. In certain embodiments, the anti-cancer agent is an anthracycline (e.g., doxorubicin, epirubicin). In certain embodiments, the anti-cancer agent is an alkylating agent (e.g., a cytoxan). In certain embodiments, the controlled-release and/or sustained-release formulation releases the anti-cancer therapeutic agent (e.g., taxane (e.g., docetaxel, paclitaxel)) over an extended period of time.

The present disclosure also provides methods of using the polymers described herein, or compositions (e.g., pharmaceutical compositions) or formulations thereof, in human medical applications (e.g., medical, industrial, research uses), or in topical applications. Provided are methods of using the polymers described herein, or compositions (e.g., pharmaceutical compositions, cosmetic compositions, nutraceutical compositions) or formulations thereof, in non-human applications (e.g., veterinary applications). Provided herein are methods of using the polymers described herein, or compositions (e.g., pharmaceutical compositions, cosmetic compositions, nutraceutical compositions) or formulations thereof, as part of a material (e.g., biodegradable materials, biocompatible materials, wound dressing (e.g., bandages (e.g., liquid spray-on bandages, viscoelastic bandages)), drug depots), drug depots, coatings, for or as scaffolds for tissue engineering). The polymers and compositions described herein may be useful in coatings (e.g., surface coatings), bulking agents, sealants, additives (e.g., food additives, pharmaceutical additives, product additives), diagnostics, barrier materials, separators of biomolecules and/or cells, biosensors, agricultural applications, and/or hygienic products (e.g., towels, tissue papers, diapers). Provided herein are methods of using the polymers described herein, or compositions (e.g., pharmaceutical compositions) or formulations thereof, in an intraoperative setting or in preventing a peritoneal adhesion. Provided are methods of using the polymers described herein, or compositions (e.g., pharmaceutical compositions) or formulations thereof, comprising delivery methods (e.g., topical delivery, ocular delivery (e.g., delivery to the front of the eye, delivery to the back of the eye). In certain embodiments, the polymers described herein are delivered to a subject orally, rectally, parenterally, intracisternally, intravaginally, intranasally, intraperitoneally, topically (as by powders, creams, ointments, or drops), bucally, or as an oral or nasal spray. In certain embodiments, polymers described herein are delivered by topical delivery. In certain embodiments, polymers described herein are delivered by ocular delivery. In certain embodiments, the ocular delivery comprises delivery to the front of the eye. In certain embodiments, the ocular delivery comprises delivery to the back of the eye. In certain embodiments, the methods described herein include administering to a subject a composition described herein. In certain embodiments, the methods described herein include contacting a cell with a composition described herein. In certain embodiments, the cell is in vitro. In certain embodiments, the cell is in vivo. In certain embodiments, the cell is ex vivo.

The present disclosure also provides the polymers described herein, or compositions (e.g., pharmaceutical compositions) or formulations thereof, for use in delivering agent(s) (e.g., for therapeutic, ophthalmic, intraoperative, or cosmetic use) to a subject, cell, tissue, or biological sample. The present disclosure also provides the polymers described herein, or compositions (e.g., pharmaceutical compositions, cosmetic compositions, diagnostic compositions) or formulations thereof, for use in human medical applications (e.g., medical (e.g., surgical), industrial, research uses). Provided are polymers described herein, or compositions (e.g., pharmaceutical compositions) or formulations thereof, for use in in cosmetic (e.g., topical applications). Provided are the polymers described herein, or compositions (e.g., pharmaceutical compositions, cosmetic compositions, diagnostic compositions) or formulations thereof, for use in non-human applications (e.g., veterinary, research, industrial applications). Provided herein are the polymers described herein, or compositions (e.g., pharmaceutical compositions, cosmetic compositions, diagnostic compositions) or formulations thereof, for use as part of a material (e.g., biodegradable materials, biocompatible materials, wound dressing (e.g., bandages (e.g., liquid spray-on bandages, viscoelastic bandages)), drug depots, coatings). In certain embodiments, the polymers described herein, or compositions thereof, are for use as a scaffold for tissue engineering. Provided herein are the polymers described herein, or compositions (e.g., pharmaceutical compositions) or formulations thereof, for use in an intraoperative setting (e.g., as part of a drug depot comprising polymers described herein, in a tumor resection), or in preventing a peritoneal adhesion. Provided are the polymers described herein, or compositions (e.g., pharmaceutical compositions) or formulations thereof, for use in delivering agents (e.g., a protein, a peptide, a polynucleotide, a small molecule, therapeutic agent (e.g., a small molecule, biologic), e.g., via topical delivery, ocular delivery (e.g., delivery to the front of the eye, delivery to the back of the eye).

EXAMPLES

In order that the present disclosure may be more fully understood, the following examples are set forth. The synthetic and biological examples described in this application are offered to illustrate the compounds, pharmaceutical compositions, and methods provided herein and are not to be construed in any way as limiting their scope.

Example 1

Figure 1B:
FIG. 1B shows β-aminoacrylates are formed via the 1,4-addition of amines onto terminal alkynoates.

The generation of a new hydrogel platform was sought, where the platform could serve as an alternative to traditional "click" hydrogels, but with improved accessibility and user-friendliness. It was envisioned that this goal could be achieved by developing a β-aminoacrylate hydrogel platform (FIG. 1A), a scaffold that could be formed via the 1,4-addition of secondary amines onto terminal alkynoates without catalysts, initiators, or specialized equipment (FIG. 1B). A recently reported study from the group of Tang et al., describes a spontaneous "click"-like polymerization to form hydrophobic poly(β-aminoacrylates).[30]-31 It is important to note, however, that Tang's reaction is only reported in organic (i.e. non-aqueous) solvents for the synthesis of linear (i.e. non-cross linked) polymers. A water-compatible cross-linking reaction between amines and alkynoates was designed in order to provide synthetic access to the proposed β-aminoacrylate hydrogel platform.

With this concept in mind, the attention was focused on the molecular design of the amine(s) and the alkynoate(s). To ensure accessibility and scalability for future biomaterial applications, it was reasoned that the components should be commercially available whenever possible, or, at the very least, should be accessible on a multigram scale with single step chemistries. Towards this end, tris(2-aminoethyl)amine (Tren) molecules were selected as the amine component (water soluble small molecules with varying degrees of substitution on the amine termini)[32] and tetra-arm alkynoates were selected as the PEG component (scalable PEGs that have previously been used in hydrogel formulation, and whose precursors can be purchased with varying molecular weights).[16] Of note, this molecule selection is consistent with requirements established by the Flory-Stockmayer theory of network formation, which is important for the goal of synthesizing cross-linked networks rather than water soluble linear polymers.[33-34]

Figure 2A:
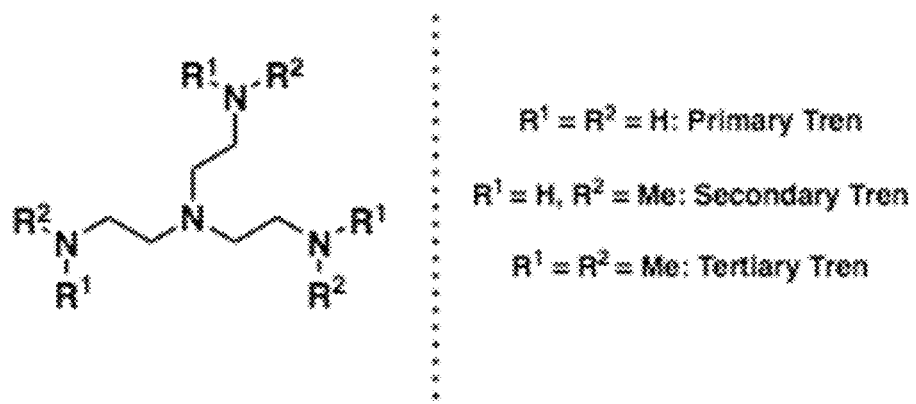
FIG. 2A shows the chemical structures of primary, secondary, and tertiary terminated Tren amine ligands ("Tren amines") used in this study.
Figure 2B:
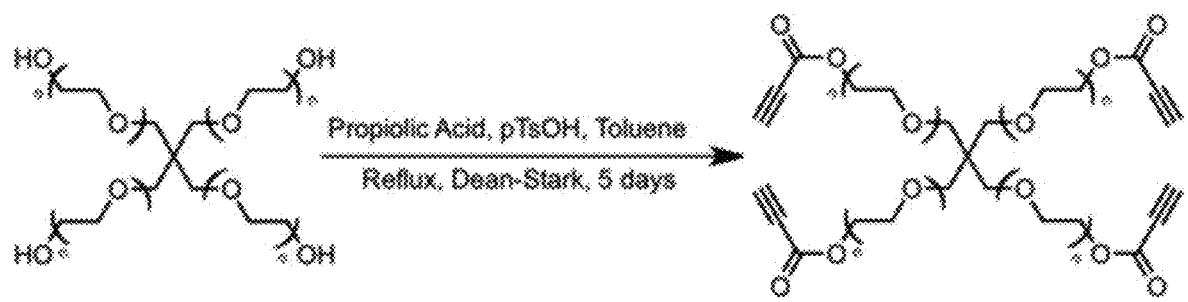
FIG. 2B shows the synthesis and structure of PEG tetra-alkynoates of varying molecular weights.
Figure 2C:
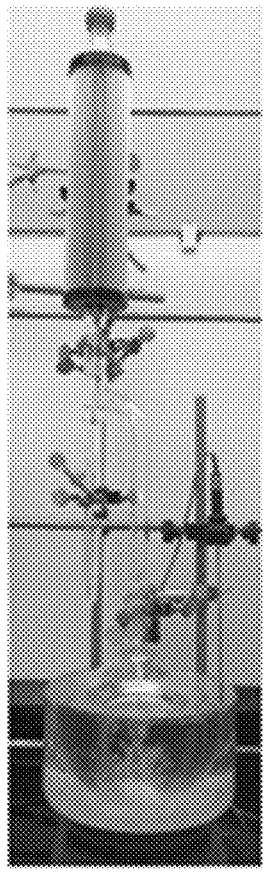
FIG. 2C is an image of the Dean-Stark Fischer esterification of 20000 g/mol PEG alkynoate on a 100 gram scale.
Figure 2D:
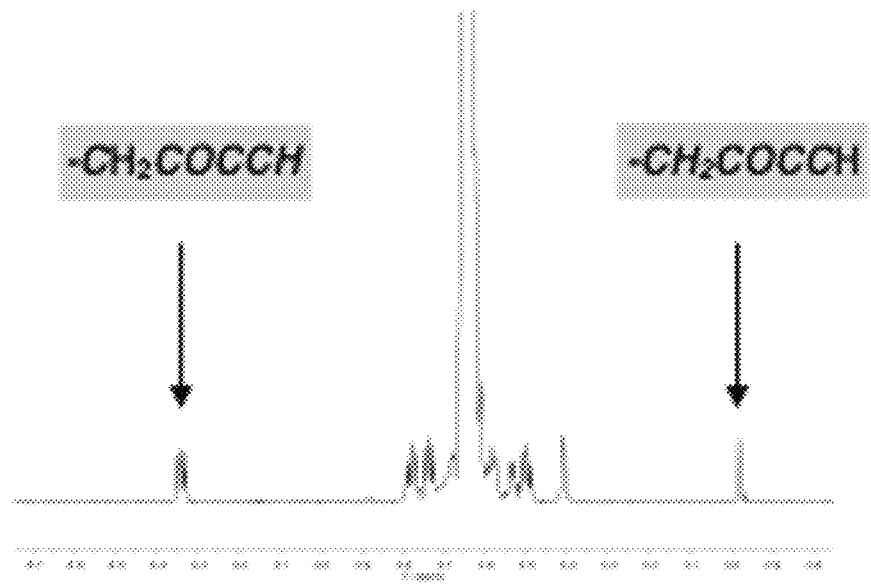
FIG. 2D is a graph showing $^1$h NMR of representative 20000 g/mol PEG tetra-alkynoate.
Figure 2E:
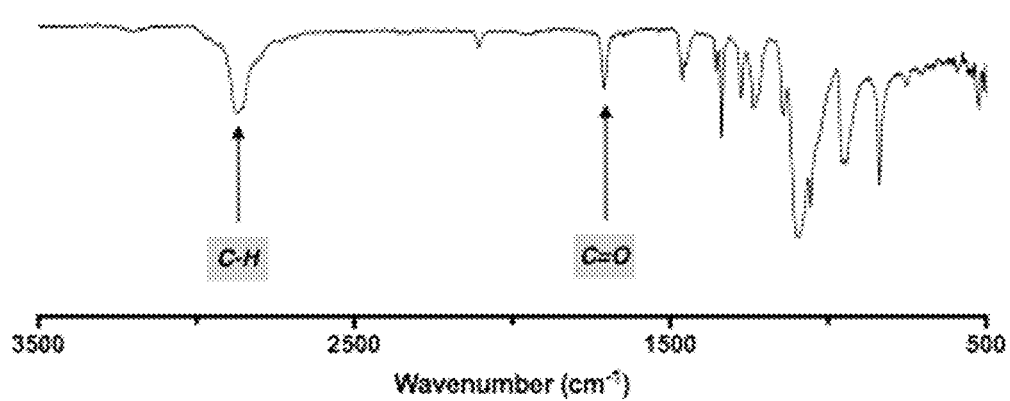
FIG. 2E is a graph of the Fourier Transform Infrared Spectrum of representative 20000 g/mol PEG tetra-alkynoate.
Figures 2F, 2G:
FIG. 2F is a table of the gel permeation chromatography data of representative PEG tetra-alkynoates relative to PEG tetra-alcohol starting materials.
FIG. 2G is an image of isolated solid PEG tetra-alkynoate on a scale.

Having established the design criteria, the focus then shifted to the acquisition of the desired components. Tren molecules with primary, secondary, and tertiary amine termini were sourced from Sigma-Aldrich (FIG. 2A). PEG tetra-alkynoates with molecular weights of 5000, 10000, and 20000 g/mol were then synthesized using a modified Fischer esterification protocol in a single step (FIG. 2B).[16] Tetra arm PEG derivatives were briefly dissolved in toluene with propiolic acid and catalytic tosic acid at reflux; a Dean-Stark trap was used to drive off the water which was liberated during the course of the reaction (FIG. 2C). Purification was performed via precipitation into cold ether with yields greater than 90%. Representative $^1$H NMR nalysis (indicating a triplet peak for the alpha protons around 4.3 ppm, and a singlet peak for the alkynoate terminus around 2.0 ppm FIG. 2D), infrared spectroscopy analysis (indicating a carbonyl signal around ~1710 cm$^{-1}$ and C-H stretches around 2800 cm$^{-1}$, FIG. 2E), and GPC analysis (indicating molecular weight retention relative to the PEG starting material, FIG. 2F) indicated high levels of purity with retention of the starting material molecular weight. Keeping scalability in mind, approximately 100 grams of the 20000 g/mol tetra-arm alkynoate was synthesized and isolated using this methodology in a single batch (FIG. 2G), which highlighted the suitability and reproducibility of the Fischer esterification for simple functionalization of PEG derivatives.[16] Additional characterization data including the $^1$H NMR and IR spectra for the 5000, 10000, and 20000 g/mol PEG tetra-alkynoates can be found in FIGS. 6A-7C.

Figure 3A:
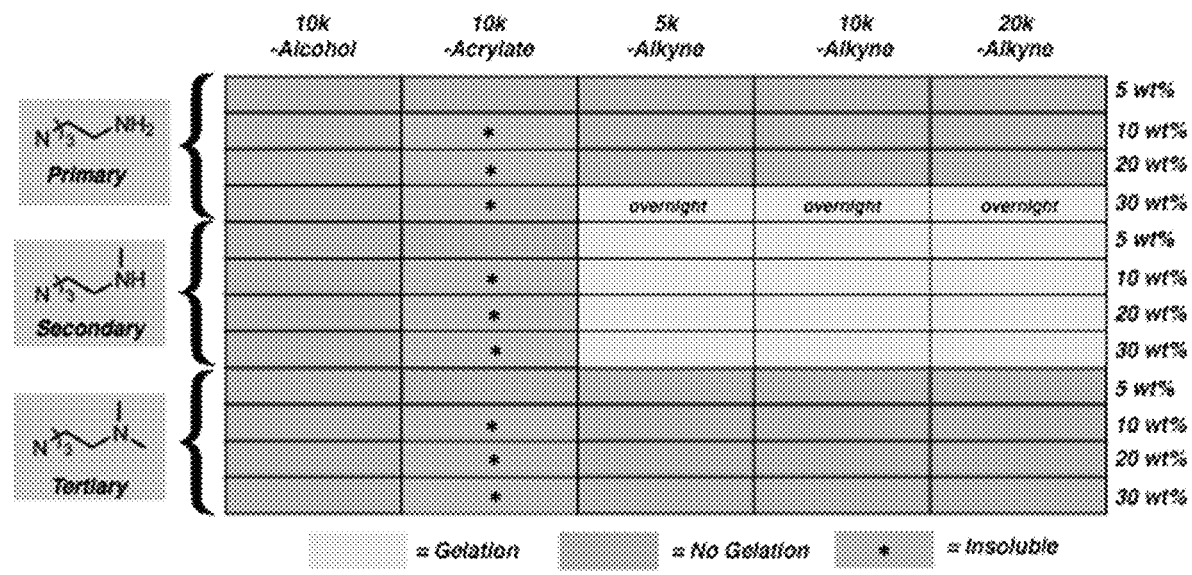
FIG. 3A is a gelation heat map studying hydrogel formation between Tren amines, PEG tetra alkynoates, and control PEGs at different weight percentages.
Figure 3B:
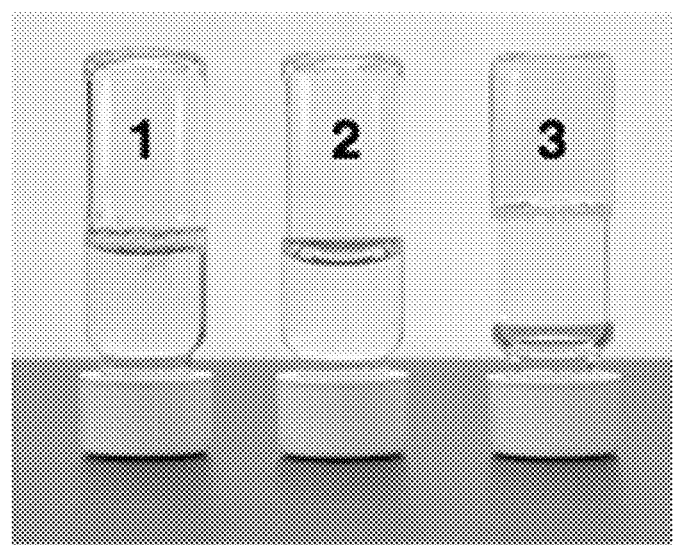
FIG. 3B is an image of a representative inverted vial test for 20000 g/mol hydrogels. Vial 1=PEG tetra-alkynoate, vial 2=Secondary Tren amine, vial 3=resultant β-aminoacrylate.
Figure 3C:
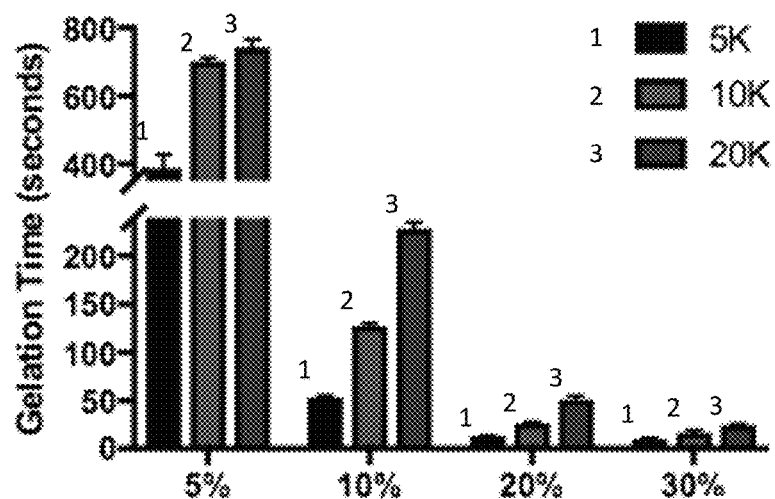
FIG. 3C is a graph showing gelation times between secondary Tren amine and varied molecular weight PEG tetra-alkynoates at different weight percentages.
Figure 8:
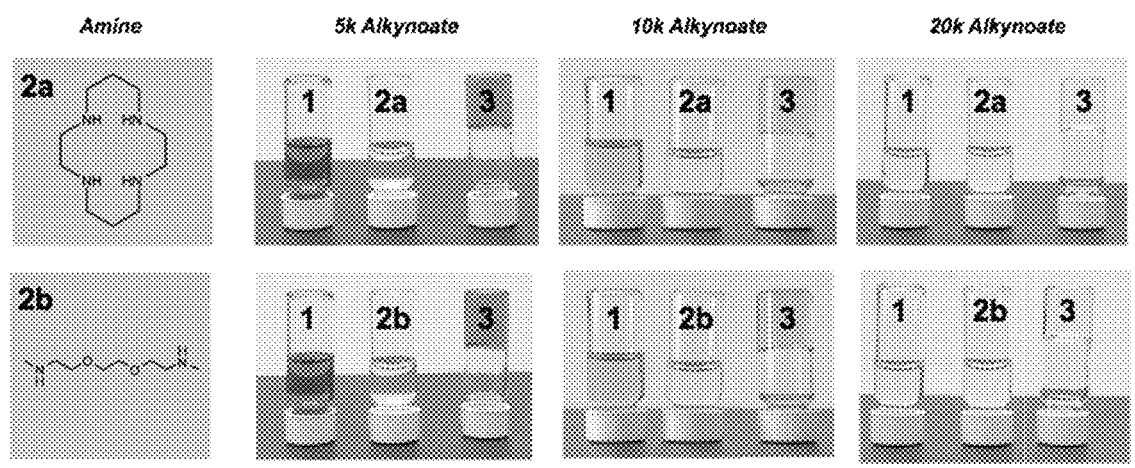
FIG. 8 is an image of representative inverted vial tests indicating generality in hydrogel formulation with secondary amines of different structure. Vial 1=PEG tetraalkynoates of designated molecular weights. Vial 2a/2b=Secondary amines of designated structure. Vial 3=Resultant hydrogels of designated combinations.

With the materials in hand, the next step was to verify the possible formation of β-aminoacrylate hydrogels using the proposed strategy of a simple mixing of the amine and alkynoate molecules. Aqueous solutions of the three Tren molecules (with primary, secondary, and tertiary amine termini) were prepared alongside aqueous solutions of the 5000, 10000, and 20000 g/mol PEG tetra-alkynoates. Each amine solution was then mixed with each respective PEG tetra-alkynoate solution at a molar ratio of 3:4 alkynoate to amines (such that the stoichiometry between alkynoate and amine reactive termini was 1:1). Gelation was assessed at 5, 10, 20 and 30 weight % loadings (where weight % refers to the ratio of the mass of PEG and amine relative to the total mass of water, e.g. w/w) for each mixture that formed hydrogel networks as measured by timed inverted vial tests (FIGS. 3A-3B). To evaluate the selectivity of the amine-alkynoate cross-linking reaction, each amine solution was also mixed with a 10000 g/mol PEG tetra-acrylate and a 10000 g/mol PEG tetra-alcohol solution. In analyzing the data, three trends emerge: i. hydrogel formation is specific to amine/PEG-alkynoate cross-linking, as no hydrogel formation was observed by substituting PEG-acrylate or the unfunctionalized PEG-alcohol, ii. tunable gelation times could be achieved by varying the weight percentage of the hydrogel, with lower weight percentages requiring longer gelation times independent of PEG-tetra-alkynoate molecular weight (FIG. 3C), and iii. primary and secondary amines can react to form hydrogels, while tertiary amines cannot. In addition to these trends, it should also be noted that the network forms more slowly from primary amines than secondary amines, and will only form hydrogels when using a 6:4 alkynoate to amine molar stoichiometry (such that the stoichiometry of the amine to the alkynoate reactive termini was 1:2). Although this may at first seem contradictory to the Flory-Stockmayer theory (given that deviations from 1:1 stoichiometry typically slow network formation), primary amines can react as nucleophiles twice and still remain a neutral species (whereas secondary amines can only react once and remain a neutral species). Accordingly, the 6:4 alkynoate to amine molar stoichiometry corresponds with a 1:1 alkynoate to amine stoichiometry if each primary amine is considered as a doubly-reactive terminus. Finally, additional secondary amines (including cyclic tetra-functional amines and linear bifunctional amines) were also evaluated to verify the generality of the findings. Gelation using secondary amines of different molecular structures with identical PEG alkynoates was successfully observed and indeed possible, which highlighted the generality of this mechanistic paradigm for synthesizing β-aminoacrylate hydrogels (FIG. 8).

Figure 3D:
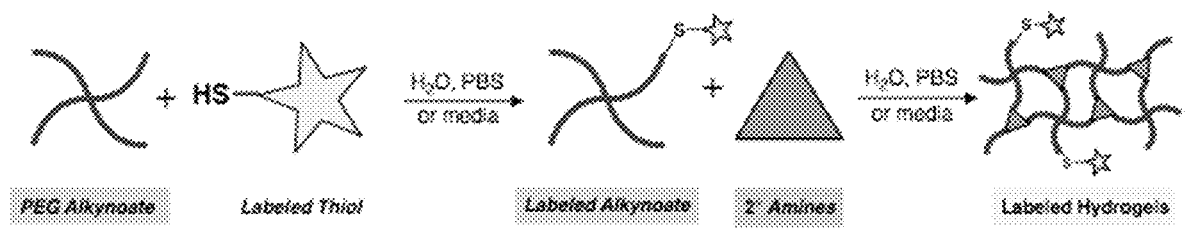
FIG. 3D is a schematic demonstrating thiol modification of the PEG tetraalkynoates to incorporate biomolecules into the β-aminoacrylate hydrogel network.
Figure 3E:
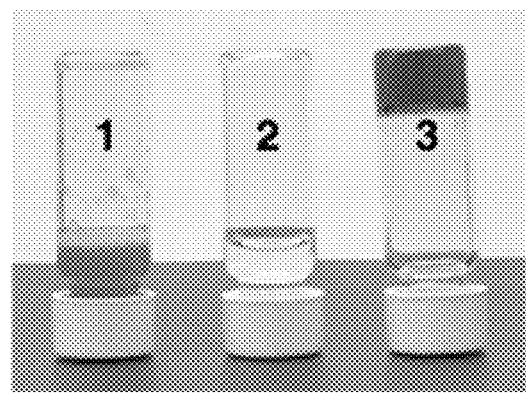
FIG. 3E is an image of a representative inverted vial test for 20000 g/mol hydrogels with covalently modified Cy5.5-2k-PEGs.

To further expand upon the utility of the hydrogel, a demonstration that additional molecules could be incorporated into the network via covalent ligation was pursued. One benefit to synthetic hydrogels is that they can be engineered from the bottom up to incorporate biomolecules within the scaffold. This process, for example, has been used to incorporate peptides, cell binding domains, and therapeutics, amongst others.[4, 19, 35] Keeping operational simplicity in mind, this goal could be achieved by first modifying the PEG tetra-alkynoate with a thiol modified biomolecule in aqueous media. This solution could then be taken directly (without the need for further purification or isolation) and cross-linked with the secondary tren ligand to form labeled β-aminoacrylate hydrogels (FIG. 3D). Towards this end, a Cy5.5-2kPEG-thiol fluorophore was reacted with the 20000 g/mol PEG alkynoate; the solution was then used directly in a cross-linking reaction with the secondary tren molecule. An inverted vial test confirmed that the Cy5.5-2kPEG-thiol fluorophore did not interfere with gelation (FIG. 3E). This result not only indicates that small molecules could be incorporated into the hydrogel, but also highlights the versatility of the β-aminoacrylate hydrogel platform in that both thiol and secondary amine mechanistic paradigms could be exploited in its synthesis and formulation.

Figure 4A:
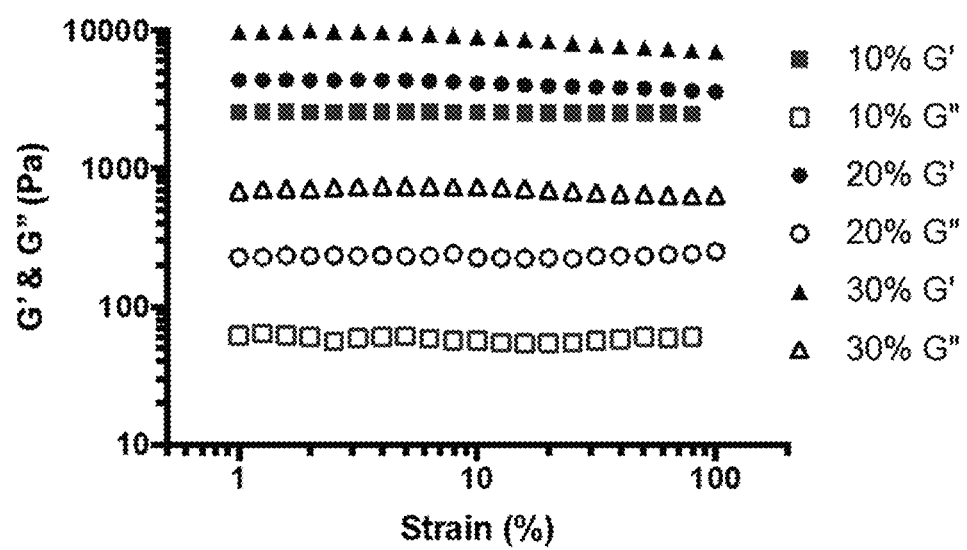
FIG. 4A is a graph showing strain sweep rheological properties as a function of weight % for 20000 g/mol PEG tetra-alkynoate/secondary Tren amine β-aminoacrylate hydrogels.
Figure 4B:
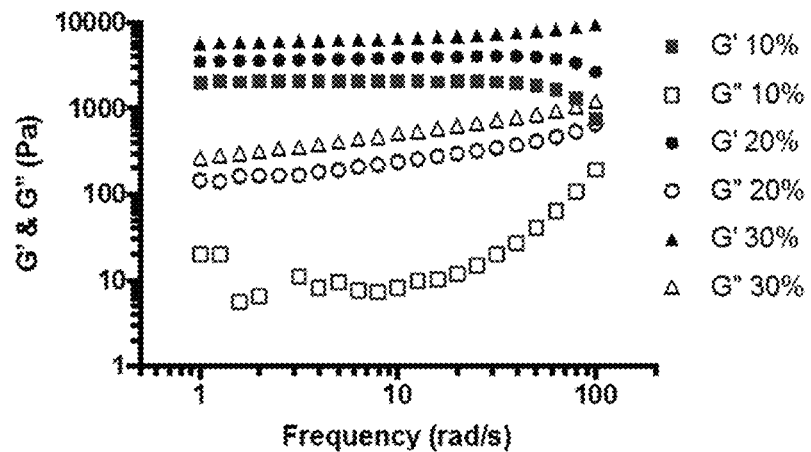
FIG. 4B is a graph showing frequency sweep rheological properties as a function of weight % for 20000 g/mol PEG tetra-alkynoate/secondary Tren amine β-aminoacrylate hydrogels.
Figure 4C:
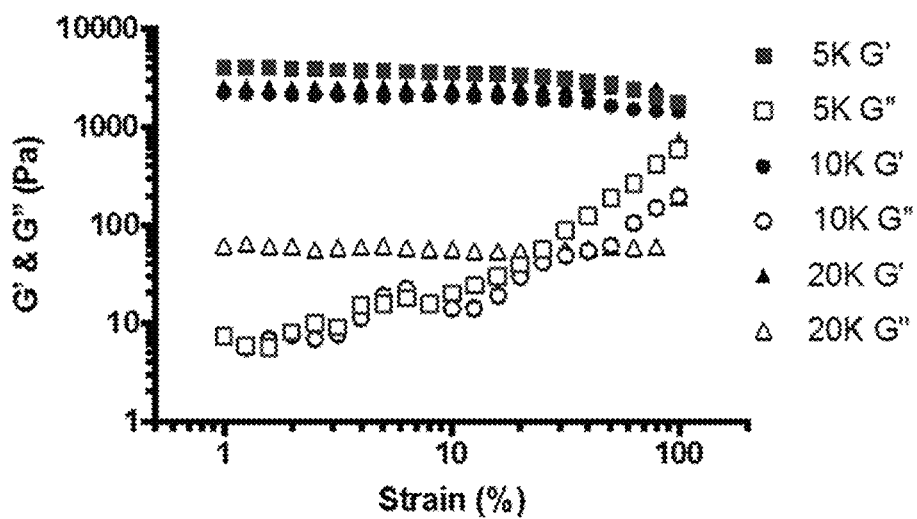
FIG. 4C is a graph showing strain sweep rheological properties as a function of PEG tetra-alkynoate molecular weight at 10 weight %.
Figure 4D:
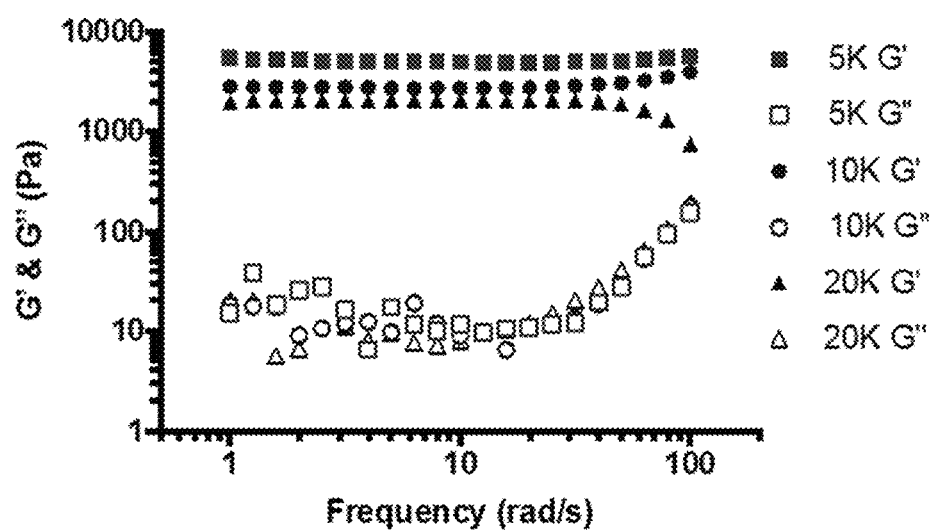
FIG. 4D is a graph showing frequency sweep rheological properties as a function of PEG tetra-alkynoate molecular weight at 10 weight %.

Having established the β-aminoacrylate hydrogel platform and the potential to modify it with pendant functionality, next material properties of the hydrogels were characterized. An understanding of how two overarching variables, namely the weight percent loading and the molecular weight of the PEG tetra-alkynoate, would impact the material properties of the hydrogels was sought. Towards this end, the strain and frequency dependent rheological properties of PEG hydrogels formulated from the secondary amine Tren molecules and the 20000 g/mol PEG tetra-alkynoate was first investigated at a weight % of 10, 20, and 30 (FIGS. 4A-4B). How the molecular weight (5000, 10000, and 20000 g/mol) of the PEG tetra-alkynoate affected these same rheological properties was also investigated at a weight % of 10 (FIGS. 4C-4D). In analyzing this data, several expected trends emerged: i. these formulations exhibited exemplary linear viscoelastic behavior over the strain and frequencies studied; ii. increasing the weight percentage of a given PEG tetra-alkynoate molecular weight increased both the storage (G') and loss moduli (G") of the hydrogel materials; iii. the tan(delta) was greater than one; and iv. varying the weight percentage had a greater impact on varying the rheological properties of these systems than varying the molecular weight of the PEG tetra-alkynoate. Collectively, these observations indicate that the hydrogel system consists of a covalent network with tunable material properties as a function of weight percent loading or PEG molecular weights that also dissipates stress predominantly via a storage (G') rather than loss (G") type mechanism at the strain and frequency parameters studied.

Having established the design, synthesis, formulation, and characterization of the hydrogel system, an evaluation of its potential for biomaterial applications was sought. Three-dimensional cell culture is one interesting application studied in the biomaterials community.[4] Even though two-dimensional culture has historically been the paradigm for in vitro cell culture, it has been demonstrated that cells can behave more natively when cultured in three-dimensional environments.[36-40] Additionally, hydrogels can be used as cell carriers for tissue engineering applications and implantation in vivo.[2, 4] Towards this end, there is interest in developing platform biomaterials that can maintain cell viability in three-dimensions over time. It was envisioned that the β-aminoacrylate hydrogel may be an ideal representative platform for this application given its operational simplicity (with its formulation only requiring simple mixing), its potential for covalent modification of the scaffold (with the potential to conjugate cell growth factors or target small molecules into the network via partial modification of the alkynoate termini), and its accessibility (with the PEG component being synthesized on 100 gram scale in a single step, and the amine being commercially available). Additionally, the system is chemically defined (unlike some naturally occurring hydrogels whose batch-to-batch inconsistency and limited tunability can limit their in vivo application as cell carriers).[4] If successful, it was envisioned that the user-friendly nature of the hydrogel could encourage researchers to perform three-dimensional cell culture experiments in scenarios where more traditional two-dimensional cell culture would normally be explored.

Prior to beginning this experiment, it was necessary to first establish two parameters: first, which cell lines would be studied, and second, which specific hydrogel formulation would be explored for cell entrapment. Toward this end, THP-1 and NIH/3T3 cells entrapped within the 10 weight % hydrogel consisting of the secondary Tren molecules and the 20000 g/mol PEG tetra-alkynoate were studied. THP-1 and NIH/3T3 cells were selected as model cell lines because they are nonadherent and adherent respectively.[41, 42] Additionally, THP-1 cells are a human monocyte line that could be used to model blood disorders or immune responses of monocyte infiltration into hydrogel networks,[43] NIH/3T3 cells, by contrast, are a mouse derived fibroblast cell line that could be used to model cell repopulation of cartilage mimicking hydrogels.[44] The 20000 g/mol PEG tetra-alkynoate/ secondary Tren hydrogel was studied to highlight the ease of access of this platform, as more than 100 grams of the PEG is accessible using a single reaction.

Figure 5A:
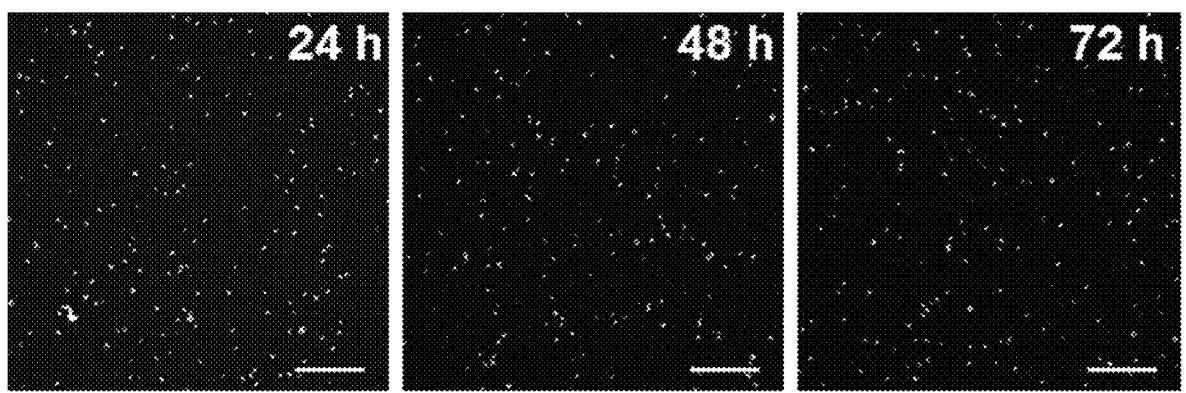
FIG. 5A shows representative merged confocal images at 24, 48, and 72 hours for THP-1 cells (human monocytic leukemia cell line used to model blood disorders or immune responses of monocyte infiltration into hydrogel networks) entrapped within a secondary Tren amine/20000 g/mol PEG tetra-alkynoate β-aminoacrylate formulation (1 million cells/mL). Exemplary Tren amines are depicted in FIG. 2A. Scale bars=50 microns.
Figure 5B:
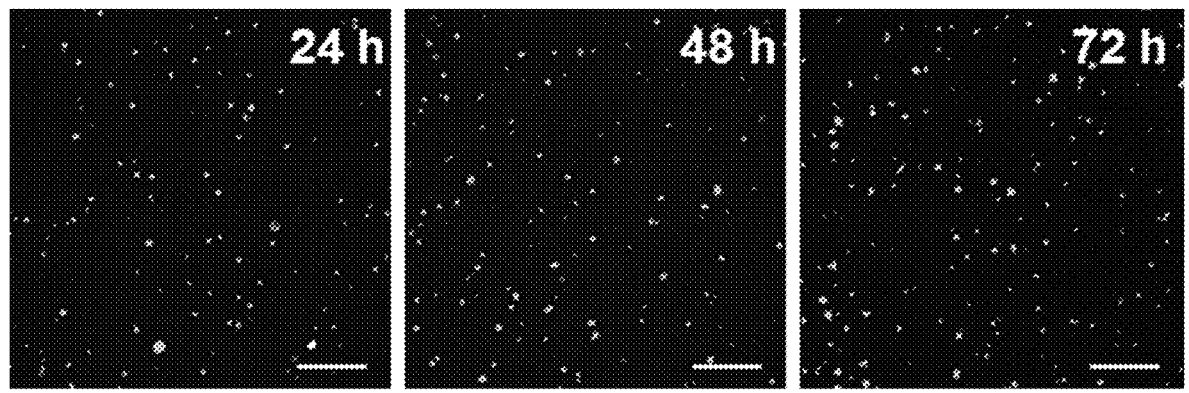
FIG. 5B shows representative merged confocal images at 24, 48, and 72 hours for NIH/3T3 cells (mouse derived fibroblast cell line used to model cell repopulation of cartilage mimicking hydrogels) entrapped within a secondary Tren amine/20000 g/mol PEG tetra-alkynoate β-aminoacrylate formulation (1 million cells/mL). Scale bars=50 microns.
Figure 5C:
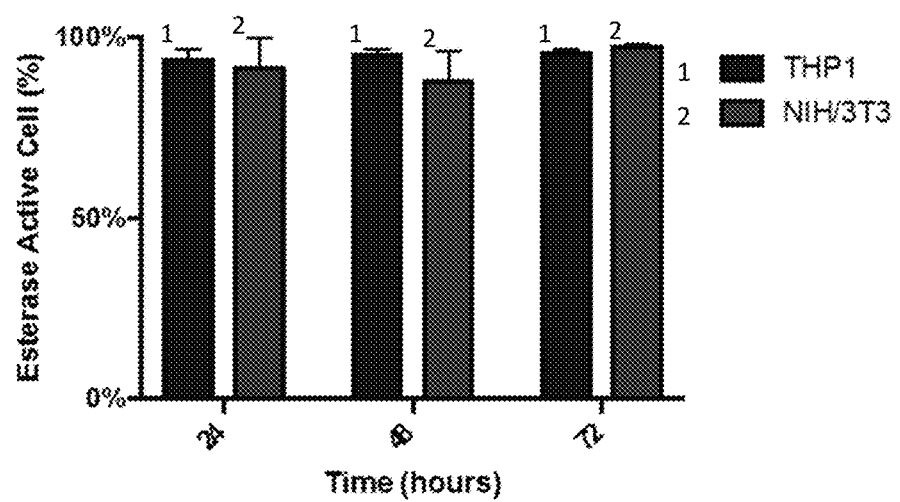
FIG. 5C is a graph showing percent live THP-1 and NIH/3T3 cells (shown as "esterase active" using a live/dead cell imaging kit, where the live cells show esterase activity) within the secondary Tren amine/20000 g/mol PEG tetra-alkynoate β-aminoacrylate formulation (1 million cells/mL).
Figure 6A:
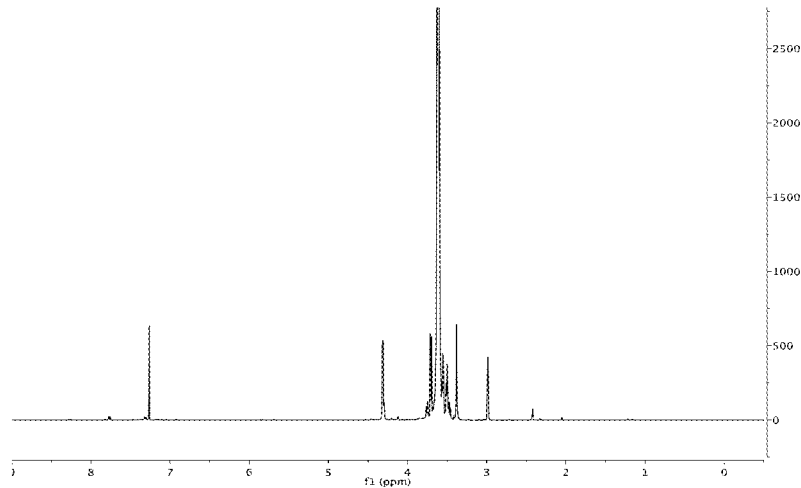
FIGS. 6A-6C are $^1$H NMR spectrum of PEG tetra-alkynoates derived from PEGs of various molecular weights.
Figure 6B:
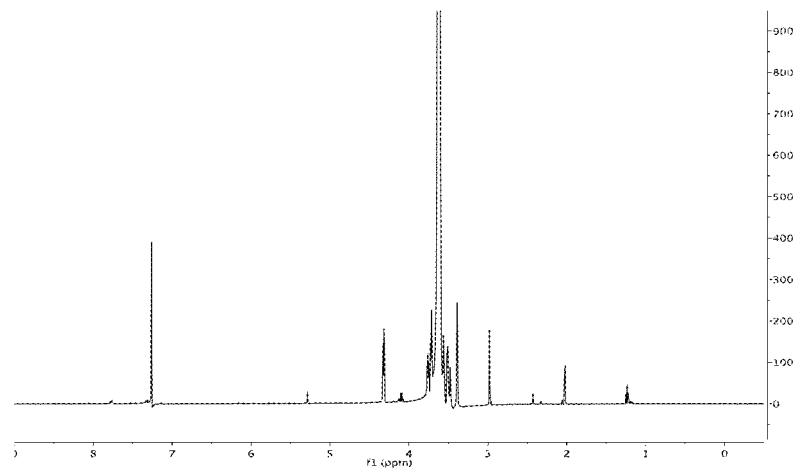
Figure 6C:
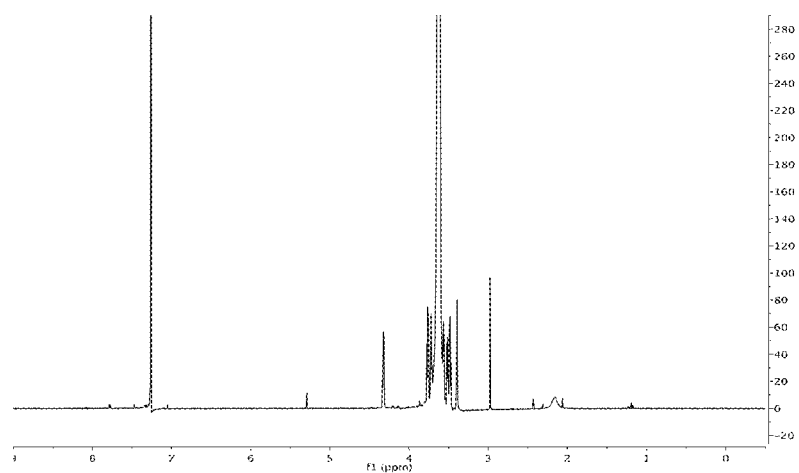
Figure 7A:
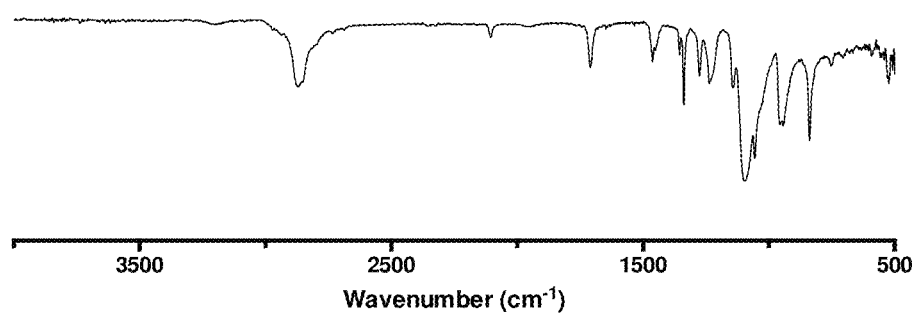
FIGS. 7A-7C are infrared spectra of PEG tetra-alkynoates derived from PEGs of various molecular weights.
Figure 7B:
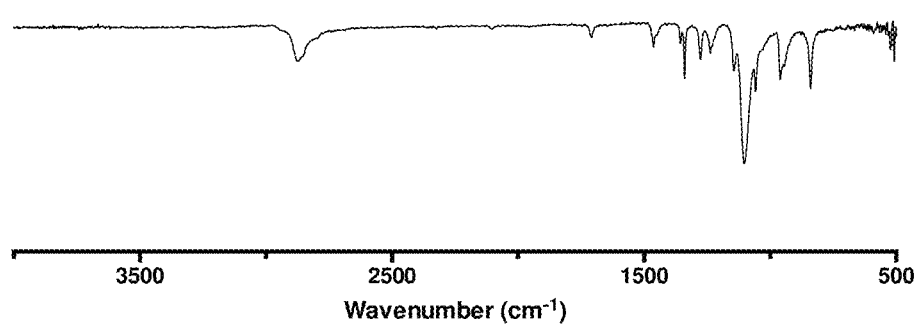
Figure 7C:
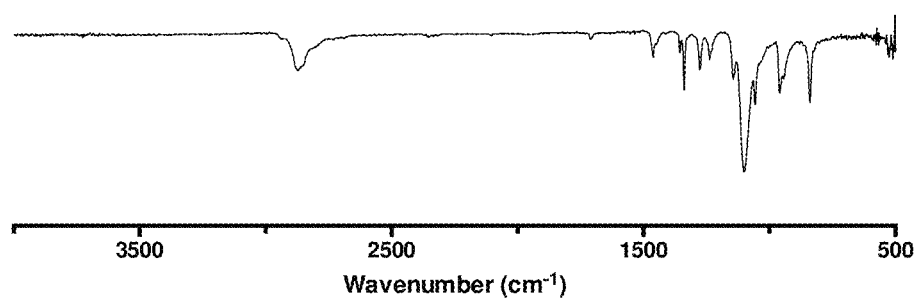
Figure 9A:
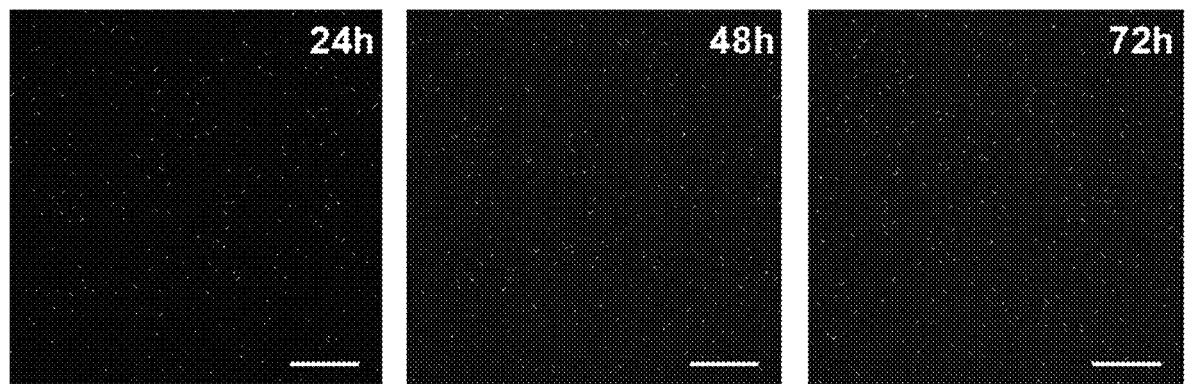
FIGS. 9A-9B are images of negative control hydrogels entrapping THP-1 and NIH/3T3 cells that were lysed after entrapment in the hydrogel. Scale bar=50 microns.
Figure 9B:
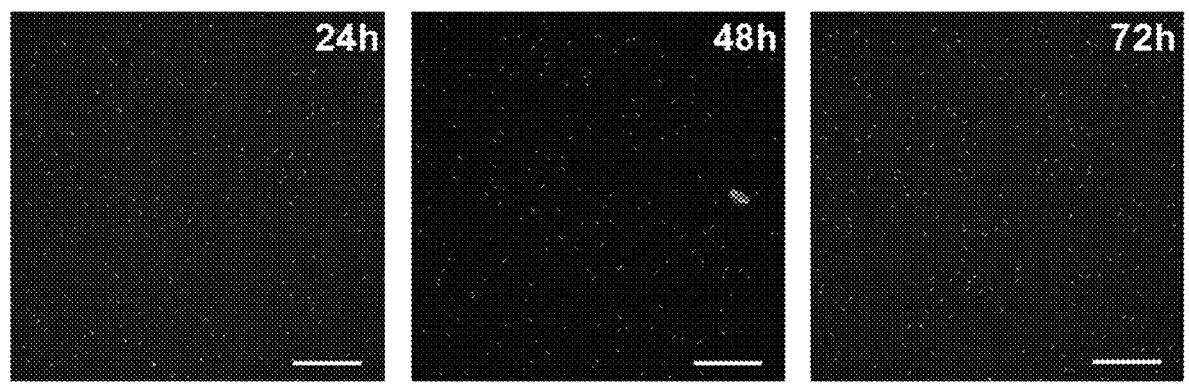
Figure 10A:
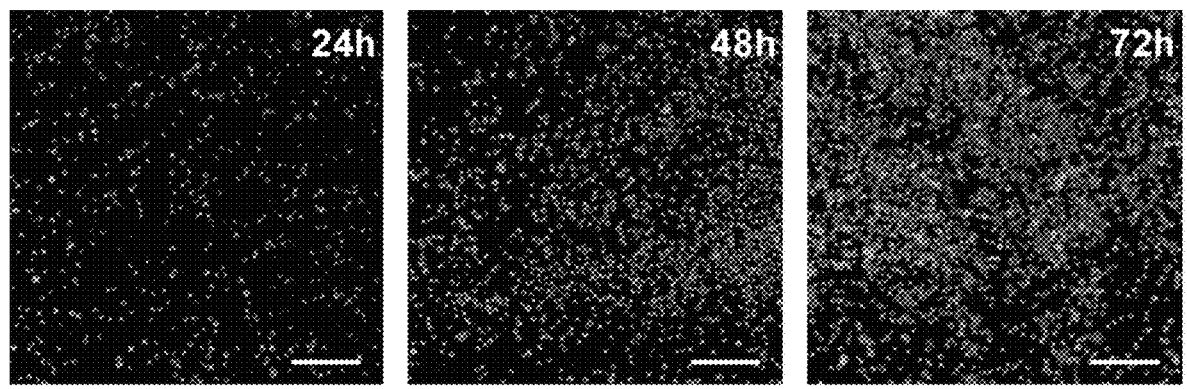
FIGS. 10A-10B are images of positive 2D controls of live THP-1 and NIH/3T3 cells cultured on TCPS. Scale bar=50 microns.
Figure 10B:
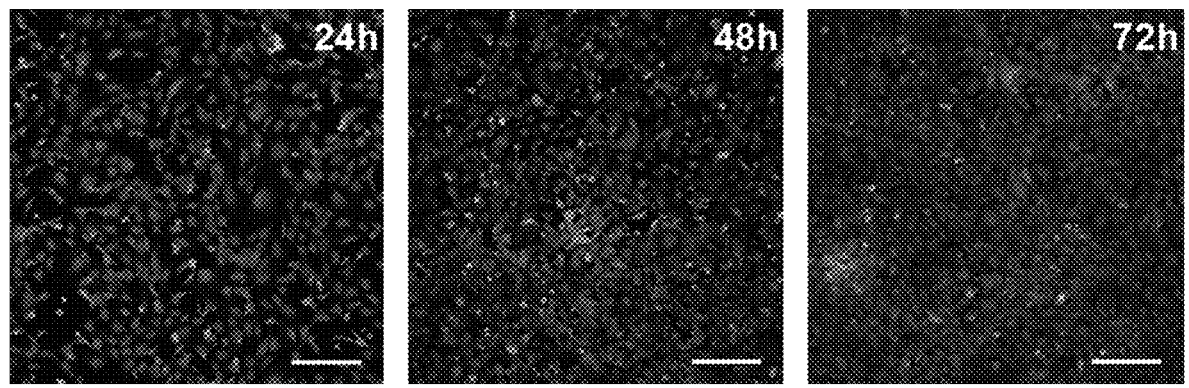

With this design criteria in hand, a three-dimensional cell culture study was performed. Briefly, a solution of the 20000 g/mol PEG tetra-alkynoate was then prepared in either RPMI (supplemented with 10% FBS, 1% penicillin streptomycin, and 0.05 mM 2-mercaptoethanol for THP-1 cells) or DMEM (supplemented with 10% FBS and 1% penicillin streptomycin for NIH/3T3 cells). A solution of the secondary Tren amine was also prepared in the appropriate media for each cell line. The cells were then suspended in the PEG solution, and an appropriate amount of the Tren amine solution was then added to the requisite volume of the amine solution to afford a gel with a final cell density of 1 million cells/mL. Cells were incubated for 24, 48, and 72 hours, at which point they were incubated with live/dead stain and imaged using confocal microscopy. Representative merge images (that combine both the live [green] and dead [red] channels) were then processed (FIGS. 5A-5B). The percent of live cells (defined as esterase active cells by the Live/ Dead kit) was also quantified using ImageJ (FIG. 5C). A negative 3D control was also studied, in which cells were killed after entrapment within the gel (FIGS. 9A-9B). 2D controls were also evaluated (FIGS. 10A-10B). In analyzing this data, three trends emerge: i. both THP-1 cells and NIH/3T3 cells remain viable over a 72 hour time course with little to no reduction occurring during this time frame ii. THP-1 cells retain their natural spherical morphology, and iii. NIH/3T3 cells do not adhere to the substrate. Nevertheless, these findings indicate that the platform can indeed recapitulate viable cell populations in 3-dimensions, highlighting the potential of the scaffold as a synthetic hydrogel for biomaterial applications.

Example 2

Instrumentation and Materials

Respective proton magnetic resonance spectra ($^1$H NMR) were conducted using an inverse probe (Varian INOVA-500) in the Department of Chemistry Instrumentation Facility (DCIF) at MIT. Results are reported in parts per million (ppm) on a δ scale referenced to the deuterated solvent ($CDCl_3$: 7.26 ppm). Gel permeation chromatography (GPC) experiments were conducted on a Viscotek TDA 305 utilizing an Agilent 1200 series binary pump and injector. Rheological characterization experiments were performed on a TA Instruments Advanced Rheometer 2000 in the Nanotechnology Materials Core at Koch Institute for Integrated Cancer Research at MIT.

All reagents were used as received without further purification from the manufacturer and stored according to the manufacturer's instructions. Reagents were purchased from Sigma Aldrich (Allentown, Pa., USA) excepting the following: All PEG tetramers of varying molecular weights were purchased from Creative PEGworks (Chapel Hill, N.C., USA) and stored at −20° C. p-Toluene sulfonic acid monohydrate (T0267) was purchased through TCI America (Philadelphia, Pa., USA). Cy5.5-PEG2K-SH was purchased from Nanocs Inc. (Boston, Mass., USA).

PEG-Alkynoate Synthesis and Characterization

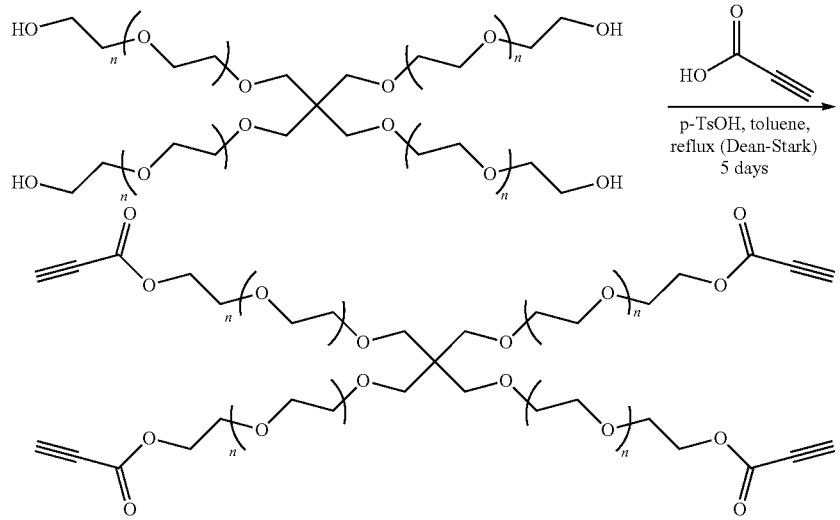

PEG-alkynoates (5000, 10000, and 20000 g/mol) were synthesized according to a modified Fisher-esterification protocol outlined by Li et al. (Efficient In Situ Nucleophilic Thiol-Yne Click Chemistry for the Synthesis of Strong Hydrogel Materials with Tunable Properties, ACS Macro Letters, Vol. 6. Issue 2. Pages 93-97. Tetra-arm PEG-OH (5 mmol, 1 equivalent ("equiv.") was briefly dissolved in toluene (0.007 M). Propiolic acid (200 mmol, 40 equiv.) and para-toluenesulfonic acid (6.67 mmol, 1.33 equiv.) was added to the solution. The reaction was then refluxed under Dean-Stark conditions using an excess of toluene in the trap and a Findenser Air Reflux Condenser (Radleys). After 5 days, the reaction was cooled to room temperature and was then concentrated under reduced pressure. The concentrated product was then dissolved in dichloromethane, and this solution was then added drop-wise to dry-ice cooled diethyl ether. The solid was isolated, and then the dichloromethane/diethyl ether crash out protocol was repeated once more. The solid PEG tetraalkynoates were then isolated, dried under reduced pressure, and then were used without further purification.

Hydrogel Formulation of PEG-Alkynoate with 1°, 2°, and 3° Terminated Tren Amines Dry PEG tetra-alkynoate was dissolved in UltraPure Distilled Water (Invitrogen) at varying concentrations in order to achieve the desired final weight percentage of 5-30%. Tren amine solutions were prepared by diluting the appropriate amine in UltraPure Distilled Water (Invitrogen). Gels were prepared by adding the diluted amine solutions directly to the PEG alkynoate solutions, followed by immediate vortexing for approximately 5 seconds to thoroughly mix. Reagents were combined to achieve a 1:1 stoichiometric ratio of functional groups (e.g. alkynoate:amine), requiring a 3:4 molar ratio of tetra-alkynoate:amine in their respective precursor solutions. Gels were allowed to set at room temperature and monitored over time.

Inverted Vial Test for Assessing Gelation Times

Gels were prepared to create a final gel volume of 200 μL formed in 1.5 mL microcentrifuge tubes. As stated above, all gels were formed by combining precursor PEG tetra-alkynoate at the required concentrations to achieve a final weight percentage of 5-30% and diluted amine solutions at a 1:1 stoichiometric ratio of functional groups (e.g. alkynoate:amine). In the case of the primary amine ligands, the ratios were also adjusted to account for the ability of each primary amine to form two bonds through the polymerization reaction. Upon combination of the precursors, a timer was immediately started and the solution was vortexed for 5 seconds and then allowed to set at room temperature. Gelation time was determined by inverting the microcentrifuge tube containing the combined reagents and gentle agitation of the microcentrifuge tube. Gels were determined to have formed completely when no solution was observed to flow during the inversion of the tube. Experiments were completed in triplicate and times were recorded and averaged.

Rheological Characterization of the Hydrogels

Gel samples were prepared by combining dissolved precursors in a microcentrifuge tube at a 1:1 stoichiometric ratio as described above. Upon mixing, gels were immediately transferred into space between two glass slides separated by 1 mm of rubber. Samples were then left at room temperature to gel for 90 minutes. An 8 mm biopsy punch was used to create a circular sample that was transferred to the Peltier plate of the rheometer equilibrated at 25° C. for testing. All measurements were conducted using an eight-millimeter stainless steel geometry. Dynamic oscillatory strain amplitude sweeps were conducted at a frequency of 10 radians/second with strain increased logarithmically from 0.1% to 100%. Dynamic oscillatory frequency sweeps were conducted at a constant strain of 2.5% with the frequency increased logarithmically from 0.1 radians/second to 100 radians/second.

Conjugation of Cy5.5-PEG-Thiol to PEG-Tetra-Alkynoate

Conjugation of Cy5.5 Through Thiol-Yne Click Reaction to PEG Terta-Alkynoate

Dry PEG tetra-alkynoate was dissolved in UltraPure Distilled Water (Invitrogen) at varying concentrations in order to achieve the desired final weight percentage of 10%. Cy5.5-PEG-Thiol (2K, Nanocs Inc.) was dissolved in Ultra-Pure Distilled Water (Invitrogen) to achieve a final concentration of 20 mg/mL (0.007 M). The aqueous Cy5.5-PEG- Thiol was added to the PEG tetra-alkynoate solution in a molar ratio of 1:32, equivalent to the conjugation of Cy5.5 to one arm of PEG tetra-alkynoate for every eight available PEG tetra-alkynoate. The solution was mixed by vortexing for approximately 5 seconds and allowed to react at room temperature for 1 hour prior to hydrogel network formation. Tren amine solutions were prepared by diluting the appropriate amine in UltraPure Distilled Water (Invitrogen). Gels were prepared by adding the diluted amine solutions directly to the Cy5.5-conjugated PEG alkynoate solutions, followed by immediate vortexing for approximately 5 seconds to thoroughly mix. Reagents were combined to achieve a 1:1 stoichiometric ratio of functional groups (e.g. alkynoate: amine), effectively equivalent to 31 of every 32 available alkynoate groups in solution. Conjugated gels were allowed to sit at room temperature for 1 hour prior to inverted vial testing.

Evaluation of Cy5.5 Conjugation Through Release Study

Conjugated Cy5.5-PEG-tetra-alkynoate was prepared as described above. Gels were prepared for a final volume of 500 uL and prepared in 4 mL scintillation vials to ensure consistent gel structure and allowed to gel for at least 30 minutes. Gels were then transferred to a transwell membrane in a 12-well transwell plate (Corning). Gels were surrounded with 2 mL of PBS 1× and 400 uL was removed and replaced with fresh PBS 1× at desired timepoints. Naked gels without Cy5.5-PEG-SH were also analyzed. All release timepoints were compared to controls of: naked PEG-tetra-alkynoate, Tren amine solution, PBS lx, Cy5.5-PEG-tetra-alkynoate solution at equivalent (100%) concentration found in gels, Cy5.5-PEG-tetra-alkynoate solution at reduced (25%) concentration found in gels. Samples were run in triplicate and analyzed by a TECAN plate reader (Model #) at 650 nm excitation/670 nm emission.

Encapsulation of Cells in Hydrogels

Cells were purchased from the ATCC (Manassas, Va.), Cell culture media, fetal bovine serum (FBS), penicillin-streptomycin, Live/Dead Viability/Cytotoxicity Assay were purchased from Thermo Fisher Scientific (Waltham, Mass., USA). All other reagents were purchased from Sigma-Aldrich Co. (St Louis, Mo., USA) unless otherwise specified.

Encapsulation of Cells in Hydrogels

To evaluate cytocompatibility of both the chemical reaction undergone during gelation and the completed hydrogel, THP1 (a nonadherent cell line) and NIH/3T3 cells (fibroblasts) were encapsulated in the hydrogels. Cells were cultured respectively in RPMI 1640 (supplemented with 10% FBS, 1% penicillin streptomycin and 0.05 mM beta-mercaptoethanol) and DMEM (supplemented with 10% FBS and 1% penicillin streptomycin). Cells were used between passages 4 and 20.

Evaluation of Cell Viability Within Hydrogels

Precursor solution containing amine was prepared by sterile filtering (0.2 µm PVDF) a solution of Tren amine diluted with PBS 1× pH 7.4 (Invitrogen). A precursor solution containing UV-sterilized PEG-alkynoate was prepared by first dissolving the sterile polymer using appropriate cell culture media (e.g. RPMI 1640 for THP1, DMEM for NIH/3T3) to 2× the required concentration. PEG-alkynoate was further diluted with a suspension of the requisite cells at a concentration of $2\times10^6$ cells/mL and gently mixed by pipetting. The required amount of amine solution for a 1:1 stoichiometric ratio of functional groups was then added to the cell suspension and quickly mixed by pipetting. Before gelation could occur, 150 µL aliquots of the cell suspension in gelation components were transferred to a well of an eight-well Lab-Tek II Chambered Coverglass slide. Gels were allowed to set at room temperature for 10 minutes, resulting in encapsulated cells at a concentration of $1\times10^6$ cells/mL.

Upon gelation, 150 µL of additional cell culture media (RPMI for THP1, DMEM for NIH/3T3) was added on top of the gel to prevent significant evaporation. 15 µL of Triton-X detergent was added to one well of each cell type as a negative control to kill all cells in the well. Samples were cultured in duplicate and left to incubate at 37° C., 5% $CO_2$ for 24, 48, or 72 hours. Upon completion of the desired incubation period, slides were removed from the incubator and treated with the Live/Dead Viability/Cytotoxicity Assay (L3224, ThermoFisher) prepared in DPBS lx (Invitrogen) per the manufacturer's protocol. Encapsulated cells were incubated with the Live/Dead stain for 30 minutes before the stain was removed and gels were washed with sterile PBS 1× (Invitrogen). Encapsulated cells were then imaged on an Olympus FV 1200 laser scanning confocal microscope using the filters for calcein (488 nm) and ethidium homodimer-1 (546 nm). Images were taken in 5 µm steps from the bottom of the gel through a 450 µm Z-section of the gel. Images were processed using ImageJ to create a Z-projection of a 400 µm section of the gel using maximum intensity projections which were then quantified using the particle analyzer tool in the program. Viability was calculated by determining the number of esterase-active cells divided by the total number of identified cells.

Evaluation of Cytocompatibility of Gelation Reaction in Cell Encapsulation

THP1 and NIH/3T3 cells were encapsulated as described in the procedure above at a final concentration of $1\times10^6$ cells/mL. Encapsulated cells were not treated with additional media but were instead placed directly in an incubator at 37° C., 5% $CO_2$ and incubated for 2, 6, or 24 hours. Additionally, a sample of encapsulated cells was treated immediately post-gelation with the calcein/ethidium homodimer-1 assay as described above and observed via confocal microscope. Viability was determined through ImageJ using the same procedure outlined previously.

Example 3

Release Study of Taxanes from B-Aminoacrylate Synthetic Hydrogel

Materials and Methods

All reagents were bought from Millipore Sigma unless otherwise specified. 20 kDa (~20,000 g/mol) PEG alkynoate was synthesized as previously described (Fenton et al. 2018, B-Aminoacrylate Synthetic Hydrogels: Easily Accessible and Operationally Simple Biomaterials Networks, *Angewandte Chemie International Edition*, Wiley-Blackwell, Supplementary Fig. S1I, S2). (Batch JLA II-4) PEG alkyoate was diluted in PBS (Life Technologies) to 228 mg/mL. Secondary TREN amine (TREN) was diluted in phosphate-buffered saline (PBS) to a final concentration of 53 mM. Stock solutions of taxanes (paclitaxel and docetaxel) were prepared in ethanol at 1.5 mg/mL. Beta-aminoacrylate synthetic gels ("gels") were formed in 24 well plates. 453 uL of PEG alkynoate were mixed 500 uL of PBS and 50 uL of either PBS, or taxane and left to react at room temperature for 20 minutes. 94 uL of TREN were added to each well and mixed vigorously for a few seconds. Beta-aminoacrylate synthetic gels were allowed to form by incubation at room temperature for about 20 minutes. 1 mL of PBS was added on top of the gel to each well. The plates were then placed in an incubator at 37° C. 200 uL of PBS were taken at different time points and replaced with fresh PBS. Samples were stored at +4° C. Samples were then prepared for HPLC analysis according to a previously described protocol (Liu 2008, *J of Pharma Sci.*). Briefly, 3 mL of ethyl acetate was added to each samples. Samples were vortexed for a few seconds and let to decant. Samples were frozen and the organic phase transferred to clean tubes. The organic phase was dried under vacuum and each sample and standard was resuspended in 10% MeOH. HPLC analyses were performed on an Agilent 1100 HPLC with a C4 2.1×250 mm column set at 40° C. The wavelength of detection was 227 nm. Phases were A: water, B: MeCN. 80 uL of samples and standards were injected in a mobile phase of 30% B for 2 minutes, then 100% B at 47 minutes, at a flow rate of 0.3 cc/min. Results are shown in FIGS. 11-13.

Results

Beta-aminoacrylate synthetic gel ("gel") aspect: For the conditions with paclitaxel, the formed gels appeared blurry, whereas for conditions with docetaxel and control conditions, the gels were clear. Gels with paclitaxel swelled less (at longer timepoints) than gels formed with other conditions. For all conditions except paclitaxel, gels swelled by about 70% after 24 hours, having a final volume of about 1.5 times their initial volume. Gels formed with paclitaxel swelled by about 50%. For all conditions except paclitaxel, gels swelled by about 100% after 48 hours, having a final volume of about 2 times their initial volume. Gels formed with paclitaxel swelled by about 80%. These observations were repeatable.

Table 1 below indicates the results of the standard curves of the PEG alkynoate-TREN gels (beta-aminoacrylate synthetic gels) with docetaxel and paclitaxel, respectively, shown in FIGS. 11A-11B, as concentration of each taxane compared to the area under the curve for each taxane.

Table 2 below indicates the concentrations of taxanes docetaxel and paclitaxel following the release of taxanes docetaxel and paclitaxel from the PEG alkynoate-TREN gels (beta-aminoacrylate synthetic gels), shown in FIGS. 12A-12B.

Figure 13A:
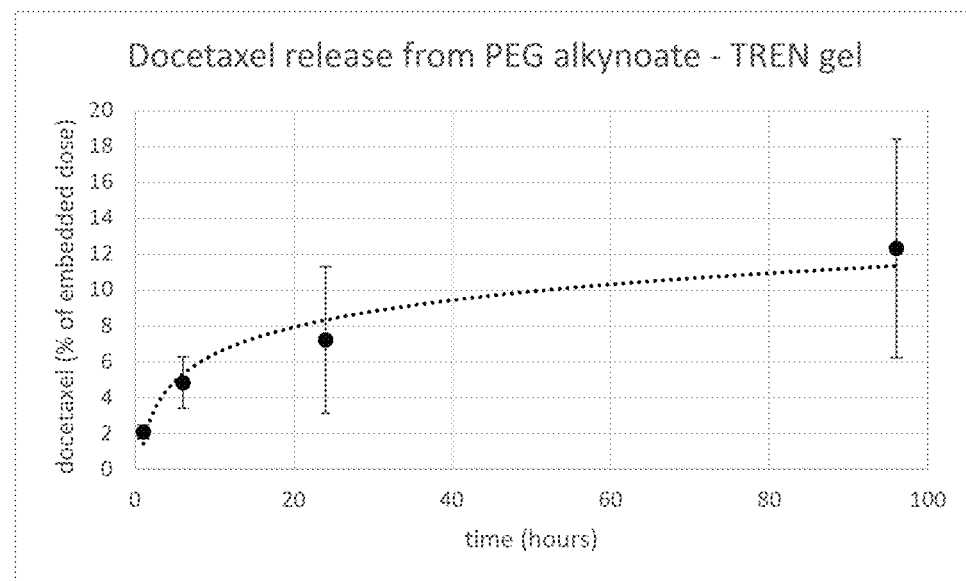
FIGS. 13A-13C are graphs showing docetaxel released from PEG alkynoate in TREN gel (FIG. 13A), paclitaxel released from PEG alkynoate in TREN gel (FIG. 13B), and a close-up section of FIG. 13B, showing a shorter time period (between 0 hours and 30 hours) of paclitaxel released from PEG alkynoate in TREN gel (FIG. 13C).
Figure 13B:
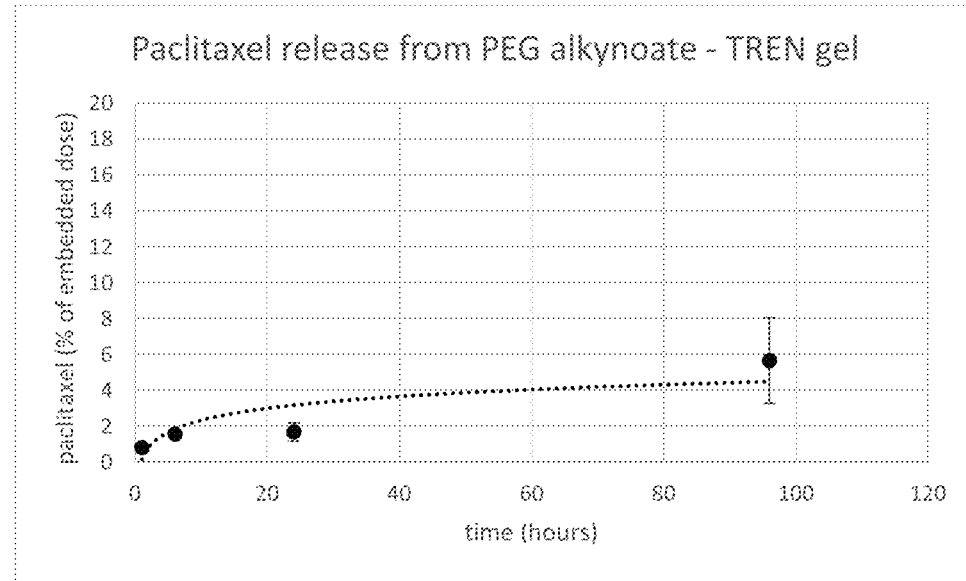
Figure 13C:
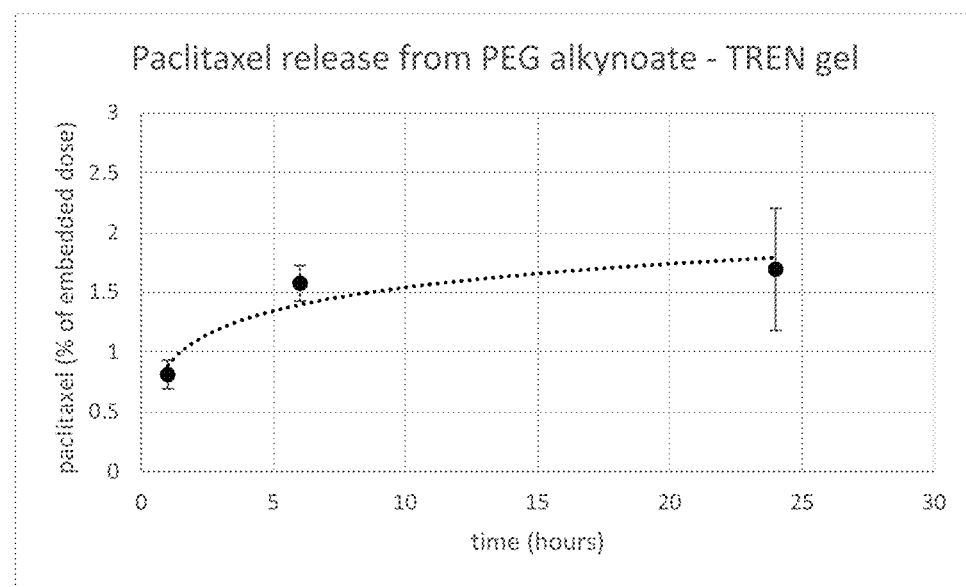

Tables 3 and 4 below indicate the percentages of taxanes docetaxel and paclitaxel following the release of taxanes docetaxel and paclitaxel from the PEG alkynoate-TREN gels (beta-aminoacrylate synthetic gels), over time, shown in FIGS. 13A-13C.

TABLE 1

Figure 11A:
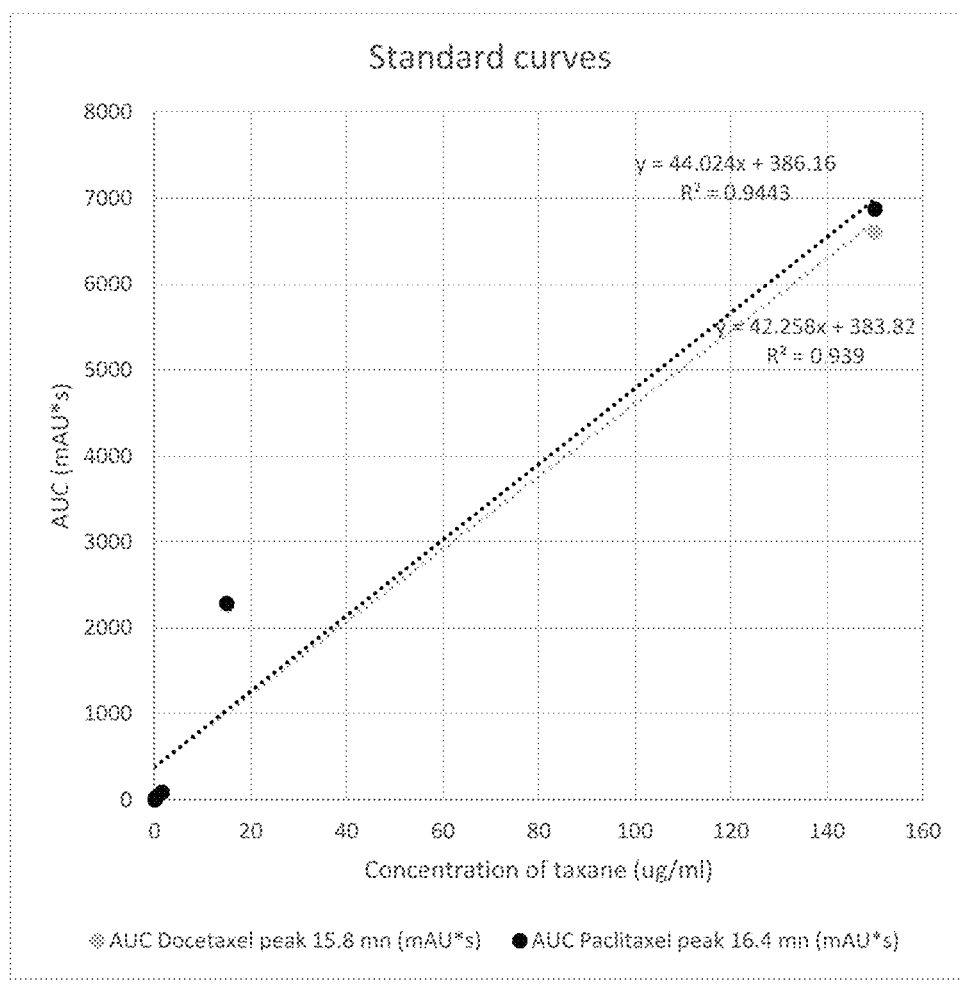
FIGS. 11A-11B are graphs showing standard curves (FIG. 11A) and standard curves for low concentrations (FIG. 11B) for polymers of Formula (I) formed using 20 kDA (~20,000 g/mol) PEG alkynoate and secondary TREN amine, as discussed in Example 2.
Figure 11B:
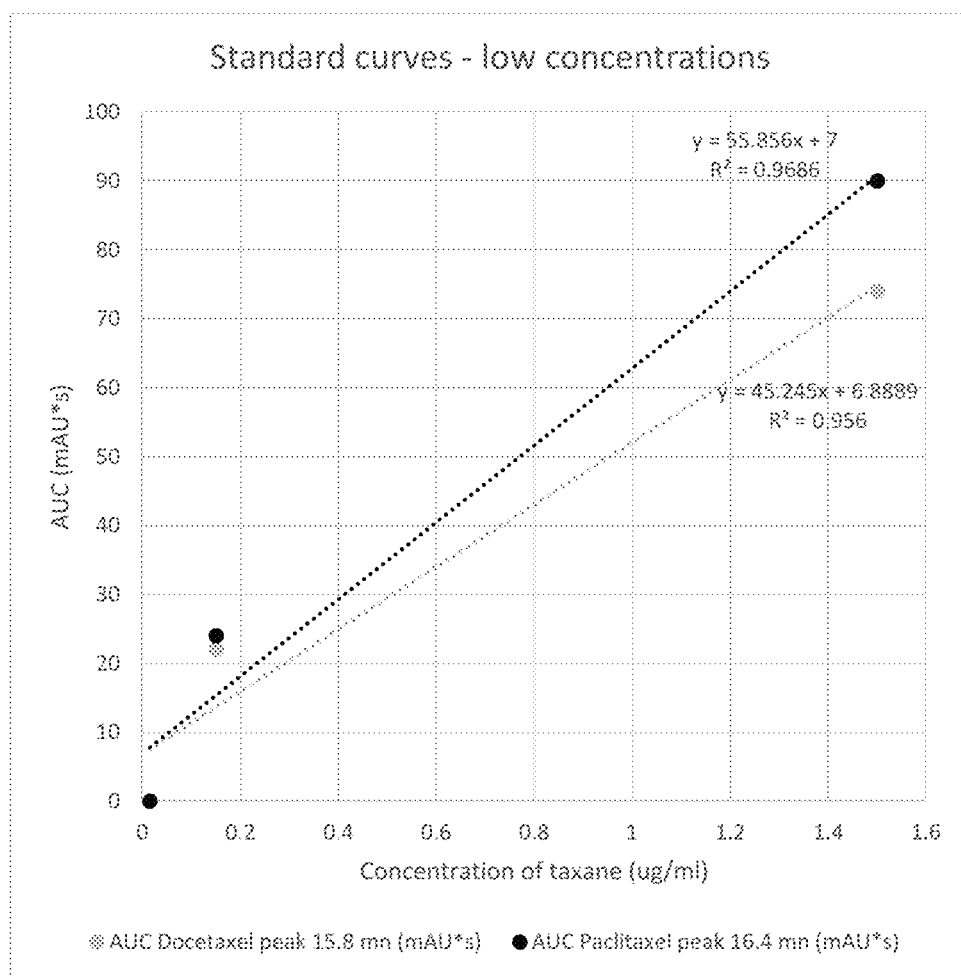

Results of the standard curves of the PEG alkynoate-TREN gels with docetaxel and paclitaxel (shown in FIGS. 11A-11B)

| [Taxane] ug/ml | AUC Docetaxel peak 15.8 mn (mAU * s) | AUC Paclitaxel peak 16.4 mn (mAU * s) |
|---|---|---|
| 150 | 6602 | 6870 |
| 15 | 2264 | 2284 |
| 1.5 | 74 | 90 |
| 0.15 | 22 | 24 |
| 0.015 | 0 | 0 |

TABLE 2

Figure 12A:
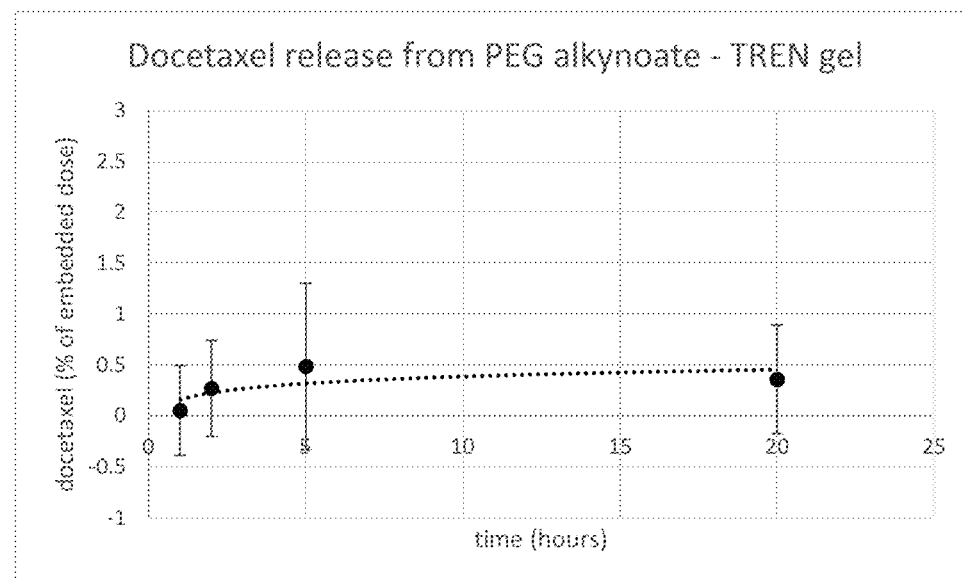
FIGS. 12A-12B are graphs showing the taxane docetaxel released from PEG alkynoate in TREN gel (FIG. 12A) and the taxane paclitaxel released from PEG alkynoate in TREN gel (FIG. 12B).
Figure 12B:
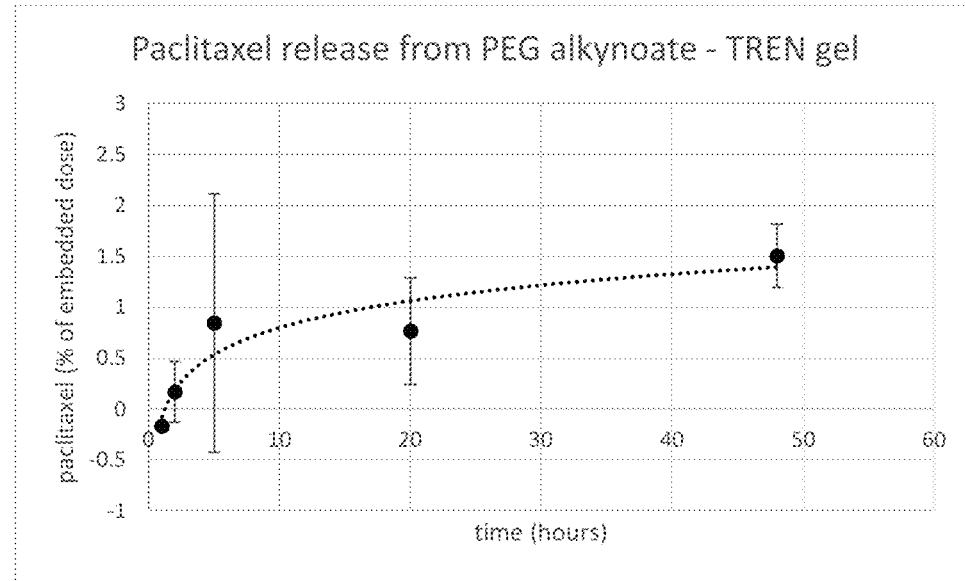

Concentrations of taxanes docetaxel and paclitaxel following the release of taxanes docetaxel and paclitaxel from the PEG alkynoate-TREN gels shown in FIGS. 12A-12B)
Concentrations (ug/mL)

| | Docetaxel | Paclitaxel |
|---|---|---|
| AUC 1 h A | −0.15226 | −0.12532 |
| AUC 1 h B | 0.422391 | −0.12532 |
| AUC 1 h C | −0.15226 | −0.12532 |
| AUC 1 h average | 0.039292 | −0.12532 |
| AUC 2 h A | −0.15226 | −0.12532 |
| AUC 2 h B | 0.555003 | 0.304354 |
| AUC 2 h C | 0.201373 | 0.196935 |
| AUC 2 h average | 0.201373 | 0.125322 |
| AUC 5 h A | 1.041244 | 1.700802 |
| AUC 5 h B | 0.201373 | 0.322257 |
| AUC 5 h C | −0.15226 | −0.12532 |
| AUC 5 h average | 0.363453 | 0.632579 |
| AUC 20 h A | 0.64341 | 0.73403 |
| AUC 20 h B | 0.311882 | 0.859353 |
| AUC 20 h C | −0.15226 | 0.125322 |
| AUC 20 h average | 0.267678 | 0.572902 |
| AUC 48 h A | | 0.984675 |
| AUC 48 h B | | 1.002578 |
| AUC 48 h C | | 1.396448 |
| AUC 48 h average | | 1.1279 |

TABLE 3

Percentages of taxanes docetaxel and paclitaxel following the release of taxanes docetaxel and paclitaxel from the PEG alkynoate-TREN gels (shown in FIGS. 13A-13C)
% released

| | Docetaxel | Paclitaxel |
|---|---|---|
| AUC 1 h A | −0.20301 | −0.1671 |
| AUC 1 h B | 0.563189 | −0.1671 |
| AUC 1 h C | −0.20301 | −0.1671 |
| AUC 1 h average | 0.052389 | −0.1671 |
| AUC 2 h A | −0.20301 | −0.1671 |
| AUC 2 h B | 0.740004 | 0.405805 |
| AUC 2 h C | 0.268497 | 0.26258 |
| AUC 2 h average | 0.268497 | 0.167096 |
| AUC 5 h A | 1.388326 | 2.267736 |
| AUC 5 h B | 0.268497 | 0.429676 |
| AUC 5 h C | −0.20301 | −0.1671 |
| AUC 5 h average | 0.484604 | 0.843439 |
| AUC 20 h A | 0.85788 | 0.978707 |
| AUC 20 h B | 0.415843 | 1.145803 |
| AUC 20 h C | −0.20301 | 0.167096 |
| AUC 20 h average | 0.356904 | 0.763869 |
| AUC 48 h A | | 1.3129 |
| AUC 48 h B | | 1.336771 |
| AUC 48 h C | | 1.861931 |
| AUC 48 h average | | 1.503867 |

TABLE 4

Percentages of taxanes docetaxel and paclitaxel following the release of taxanes docetaxel and paclitaxel from the PEG alkynoate-TREN gels (shown in FIGS. 13A-13C)
% released

| | Docetaxel | Paclitaxel |
|---|---|---|
| AUC 1 h A | 2.465425 | 0.923804 |
| AUC 1 h B | 2.016019 | 0.824024 |
| AUC 1 h C | 1.741367 | 0.687005 |

TABLE 4-continued

Percentages of taxanes docetaxel and paclitaxel following the release of taxanes docetaxel and paclitaxel from the PEG alkynoate-TREN gels (shown in FIGS. 13A-13C) % released

| | Docetaxel | Paclitaxel |
|---|---|---|
| AUC 1 h average | 2.07427 | 0.811611 |
| AUC 6 h A | 6.19475 | 1.412919 |
| AUC 6 h B | 4.946435 | 1.607706 |
| AUC 6 h C | 3.317968 | 1.70295 |
| AUC 6 h average | 4.819718 | 1.574525 |
| AUC 24 h A | 11.23133 | 2.140265 |
| AUC 24 h B | 7.325188 | 1.137449 |
| AUC 24 h C | 3.031822 | 1.796047 |
| AUC 24 h average | 7.196113 | 1.691254 |
| AUC 96 h A | 8.246395 | 6.021675 |
| AUC 96 h B | 9.349132 | 7.865225 |
| AUC 96 h C | 19.31944 | 3.116824 |
| AUC 96 h average | 12.30499 | 5.667908 |

REFERENCES

1. Peppas, N. A.; Langer, R., New challenges in biomaterials. *Science* 1994, 263 (5154), 1715-20.
2. Fenton, O. S.; Olafson, K. N.; Pillai, P. S.; Mitchell, M. J.; Langer, R., Advances in Biomaterials for Drug Delivery. *Advanced Materials* 2018, 30, 1705328.
3. Langer, R.; Tirrell, D. A., Designing materials for biology and medicine. *Nature* 2004, 428 (6982), 487-92.
4. Tibbitt, M. W.; Anseth, K. S., Hydrogels as extracellular matrix mimics for 3D cell culture. *Biotechnol Bioeng* 2009, 103 (4), 655-63.
5. Peppas, N. A.; Hilt, J. Z.; Khademhosseini, A.; Langer, R., Hydrogels in biology and medicine: From molecular principles to bionanotechnology. *Advanced Materials* 2006, 18 (11), 1345-1360.
6. Nguyen, K. T.; West, J. L., Photopolymerizable hydrogels for tissue engineering applications. *Biomaterials* 2002, 23 (22), 4307-14.
7. Lutolf, M. P.; Hubbell, J. A., Synthetic biomaterials as instructive extracellular microenvironments for morphogenesis in tissue engineering. *Nat Biotechnol* 2005, 23 (1), 47-55.
8. Sawhney, A. S.; Pathak, C. P.; Hubbell, J. A., Interfacial photopolymerization of poly(ethylene glycol)-based hydrogels upon alginate-poly(l-lysine) microcapsules for enhanced biocompatibility. *Biomaterials* 1993, 14 (13), 1008-16.
9. Annabi, N.; Tamayol, A.; Uquillas, J. A.; Akbari, M.; Bertassoni, L. E.; Cha, C.; Camci-Unal, G.; Dokmeci, M. R.; Peppas, N. A.; Khademhosseini, A., 25th anniversary article: Rational design and applications of hydrogels in regenerative medicine. *Adv Mater* 2014, 26 (1), 85-123.
10. Langer, R., Biomaterials: Status, challenges, and perspectives. *AiChE Journal* 46 (7), 1286-1289.
11. Tibbitt, M. W.; Dahlman, J. E.; Langer, R., Emerging Frontiers in Drug Delivery. *J Am Chem Soc* 2016, 138 (3), 704-17.
12. Knipe, J. M.; Peppas, N. A., Multi-responsive hydrogels for drug delivery and tissue engineering applications. *Regenertive Biomaterials* 2014, 57-65.
13. Zander, Z. K.; Hua, G.; Wiener, C. G.; Vogt, B. D.; Becker, M. L., Control of Mesh Size and Modulus by Kinetically Dependent Cross-Linking in Hydrogels. *Adv Mater* 2015, 27 (40), 6283-8.
14. Azagarsamy, M. A.; Anseth, K. S., Bioorthogonal Click Chemistry: An Indispensable Tool to Create Multifaceted Cell Culture Scaffolds. *ACS Macro Lett* 2013, 2 (1), 5-9.
15. Kharkar, P. M.; Kiick, K. L.; Kloxin, A. M., Designing degradable hydrogels for orthogonal control of cell microenvironments. *Chem Soc Rev* 2013, 42 (17), 7335-72.
16. Macdougall, L. J. T., V. X.; Dove, A. P., Efficient In Situ Nucleophilic Thiol-yne Click Chemnistry for the Synthesis of Strong Hydrogel Materials with Tunable Properties. *ACS Macro Lett* 2017, 6 (2), 93-97.
17. Agard, N. J.; Prescher, J. A.; Bertozzi, C. R., A strain-promoted [3+2] azide-alkyne cycloaddition for covalent modification of biomolecules in living systems. *J Am Chem Soc* 2004, 126 (46), 15046-7.
18. DeForest, C. A.; Anseth, K. S., Cytocompatible click-based hydrogels with dynamically tunable properties through orthogonal photoconjugation and photocleavage reactions. *Nat Chem* 2011, 3 (12), 925-31.
19. Deforest, C. A.; Sims, E. A.; Anseth, K. S., Peptide-Functionalized Click Hydrogels with Independently Tunable Mechanics and Chemical Functionality for 3D Cell Culture. *Chem Mater* 2010, 22 (16), 4783-4790.
20. Steinhilber, D.; Rossow, T.; Wedepohl, S.; Paulus, F.; Seiffert, S.; Haag, R., A microgel construction kit for bioorthogonal encapsulation and pH-controlled release of living cells. *Angew Chem Int Ed Engl* 2013, 52 (51), 13538-43.
21. Truong, V. X.; Ablett, M. P.; Gilbert, H. T. J.; Bowen, J.; Richardson, S. M.; Hoyland, J. A.; Dove, A. P., *Biomater. Sci.* 2014, 2, 167-175.
22. Blackman, M. L.; Royzen, M.; Fox, J. M., Tetrazine ligation: fast bioconjugation based on inverse-electron-demand Diels-Alder reactivity. *J Am Chem Soc* 2008, 130 (41), 13518-9.
23. Hansell, C. F.; Espeel, P.; Stamenovic, M. M.; Barker, I. A.; Dove, A. P.; Du Prez, F. E.; O'Reilly, R. K., Additive-free clicking for polymer functionalization and coupling by tetrazine-norbornene chemistry. *J Am Chem Soc* 2011, 133 (35), 13828-31.
24. Alge, D. L.; Azagarsamy, M. A.; Donohue, D. F.; Anseth, K. S., Synthetically tractable click hydrogels for three-dimensional cell culture formed using tetrazine-norbornene chemistry. *Biomacromolecules* 2013, 14 (4), 949-53.
25. Grover, G. N.; Braden, R. L.; Christman, K. L., Oxime cross-linked injectable hydrogels for catheter delivery. *Adv Mater* 2013, 25 (21), 2937-42.
26. Grover, G. N.; Lam, J.; Nguyen, T. H.; Segura, T.; Maynard, H. D., Biocompatible hydrogels by oxime Click chemistry. *Biomacromolecules* 2012, 13 (10), 3013-7.
27. Lin, F.; Yu, J.; Tang, W.; Zheng, J.; Defante, A.; Guo, K.; Wesdemiotis, C.; Becker, M. L., Peptide-functionalized oxime hydrogels with tunable mechanical properties and gelation behavior. *Biomacromolecules* 2013, 14 (10), 3749-58.
28. van de Wetering, P.; Metters, A. T.; Schoenmakers, R. G.; Hubbell, J. A., Poly(ethylene glycol) hydrogels formed by conjugate addition with controllable swelling, degradation, and release of pharmaceutically active proteins. *J Control Release* 2005, 102 (3), 619-27.
29. Kharkar, P. M.; Rehmann, M. S.; Skeens, K. M.; Maverakis, E.; Kloxin, A. M., Thiol-ene click hydrogels for therapeutic delivery. *ACS Biomater Sci Eng* 2016, 2 (2), 165-179.
30. He, B.; Su, H.; Bai, T.; Wu, Y.; Li, S.; Gao, M.; Hu, R.; Zhao, Z.; Qin, A.; Ling, J.; Tang, B. Z., Spontaneous 30. Amino-yne Click Polymerization: A Powerful Tool toward Regio- and Stereospecific Poly(beta-aminoacrylate)s. *J Am Chem Soc* 2017, 139 (15), 5437-5443.
31. Huang, D.; Liu, Y.; Qin, A.; Tang, B. Z., Recent advances in alkyne-based click polymerizations. *Polymer Chemistry* 2018, 9, 2853.
32. Blackman, A. G., The coordination chemistry of tripodal tetraamine ligands. *Polyhedron* 2005, 24, 1-39.
33. Flory, P. J., Molecular Size Distribution in Three Dimensional Polymers I. Gelation. *Journal of the American Chemical Society* 1941, 63, 3083.
34. Stockmayer, W. H., Theory of Molecular Size Distribution and Gel Formation in Branched Polymers II. General Cross Linking. *Journal of Chemical Physics* 1944, 12 (4), 125.
35. DeForest, C. A.; Anseth, K. S., Photoreversible patterning of biomolecules within click-based hydrogels. *Angew Chem Int Ed Engl* 2012, 51 (8), 1816-9.
36. Abbott, A., Cell culture: biology's new dimension. *Nature* 2003, 424 (6951), 870-2.
37. Petersen, O. W.; Ronnovjessen, L.; Howlett, A. R.; Bissell, M. J., Interaction with basement-membrane serves to rapidly distinguish growth and differentiation pattern of normal and malignant human breast epithelial cells. *Proc Natl Acad Sci USA* 1992, 89 (19), 9064-9068.
38. Tanaka, H.; Murphy, C. L.; Murphy, C.; Kimura, M.; Kawai, S.; Polak, J. M., Chondrogenic differentiation of murine embryonic stem cells: effects of culture conditions and dexamethasone. *J Cell Biochem* 2004, 93 (3), 454-62.
39. Zhang, S.; Zhao, X.; Spirio, L., PuraMatrix: Self-assembling peptide nanofiber scaffolds. Ma P. and Elisseeff, J., eds. *Scaffolding in tissue engineering* 2005, 217-238.
40. Saha, K.; Pollock, J. F.; Schaffer, D. V.; Healy, K. E., Designing synthetic materials to control stem cell phenotype. *Curr Opin Chem Biol* 2007, 11 (4), 381-7.
41. Tsuchiya, S.; Yamabe, M.; Yamaguchi, Y.; Kobayashi, Y.; Konno, T.; Tada, K., Establishment and characterization of a human acute monocytic leukemia cell line (THP-1). *Int J Cancer* 1980, 26 (2), 171-6.
42. Jainchill, J. L.; Aaronson, S. A.; Todaro, G. J., Murine sarcoma and leukemia viruses: assay using clonal lines of contact-inhibited mouse cells. *J Virol* 1969, 4 (5), 549-53.
43. Tsuchiya, S.; Kobayashi, Y.; Goto, Y.; Okumura, H.; Nakae, S.; Konno, T.; Tada, K., Induction of maturation in cultured human monocytic leukemia cells by a phorbol diester. *Cancer Res* 1982, 42 (4), 1530-6.
44. Westerman, K. A.; Leboulch, P., Reversible immortalization of mammalian cells mediated by retroviral transfer and site-specific recombination. *Proc Natl Acad Sci USA* 1996, 93 (17), 8971-6.
45. DeForest, C. A.; Polizzotti, B. D.; Anseth, K. S., Sequential click reactions for synthesizing and patterning three-dimensional cell microenvironments. *Nat Mater* 2009, 8 (8), 659-64.
46. Rydholm, A. E.; Reddy, S. K.; Anseth, K. S.; Bowman, C. N., Controlling network structure in degradable thiol-acrylate biomaterials to tune mass loss behavior. *Biomacromolecules* 2006, 7 (10), 2827-36.
47. Weber, L. M.; Hayda, K. N.; Anseth, K. S., Cell-matrix interactions improve beta-cell survival and insulin secretion in three-dimensional culture. *Tissue Eng Part A* 2008, 14 (12), 1959-68.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the disclosure, or aspects described herein, is/are referred to as comprising particular elements and/or features, certain embodiments described herein or aspects described herein consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments described herein, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment described herein can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

What is claimed is:

1. A polymer of Formula (I):

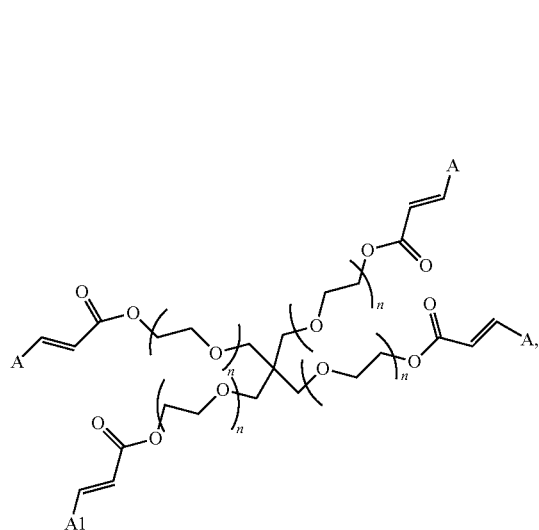

or a pharmaceutically acceptable salt, co-crystal, tautomer, stereoisomer, or isotopically labeled derivative thereof, wherein:
  each A independently is an amine; and
  each n independently is between 10-150.

2. The polymer, pharmaceutically acceptable salt, co-crystal, tautomer, stereoisomer, or isotopically labeled derivative thereof, of claim 1, wherein the amine A is of the Formula (I-A):

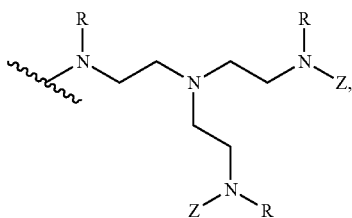

wherein:
  each R independently is H, optionally substituted alkyl, optionally substituted alkenyl, or optionally substituted alkynyl; and
  each Z independently is hydrogen, optionally substituted alkyl, optionally substituted alkenyl, optionally substituted alkynyl, or of the Formula (I-Z):

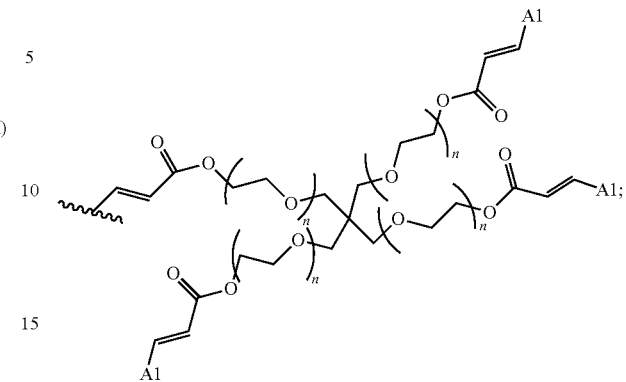

wherein each A1 independently is an amine, and each n independently is between 10-150.

3. The polymer, pharmaceutically acceptable salt, co-crystal, tautomer, stereoisomer, or isotopically labeled derivative thereof, of claim 2, wherein at least one instance of Z is of the Formula (I-Z).

4. A method of preparing a polymer, pharmaceutically acceptable salt, co-crystal, tautomer, stereoisomer, or isotopically labeled derivative thereof, of claim 2, comprising:
  reacting a tetra-arm polyethylene glycol alkynoate compound of Formula (A):

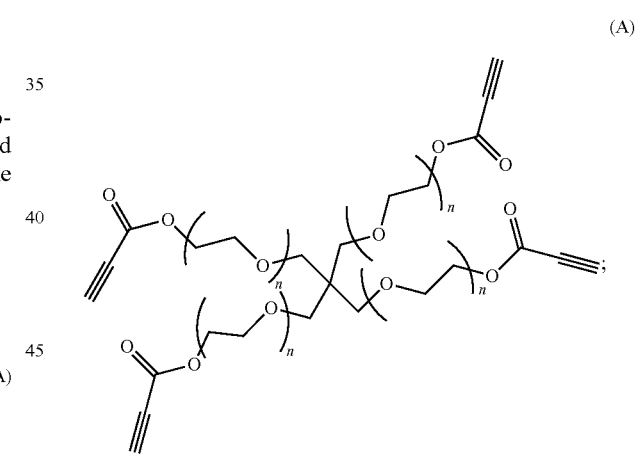

or a pharmaceutically acceptable salt, co-crystal, tautomer, stereoisomer, or isotopically labeled derivative thereof, with an amine of Formula (B):

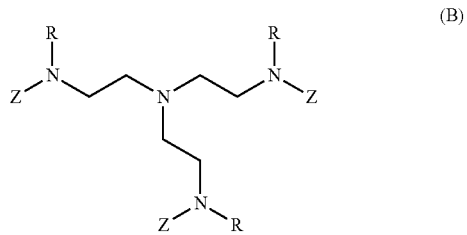

or a pharmaceutically acceptable salt, co-crystal, tautomer, stereoisomer, or isotopically labeled derivative thereof,
wherein:
each n independently is between 10-150;
each R independently is hydrogen, optionally substituted alkyl, optionally substituted alkenyl, or optionally substituted alkynyl;

each Z independently is hydrogen, optionally substituted alkyl, optionally substituted alkenyl, optionally substituted slkynyl, or the Formula (I-Z):

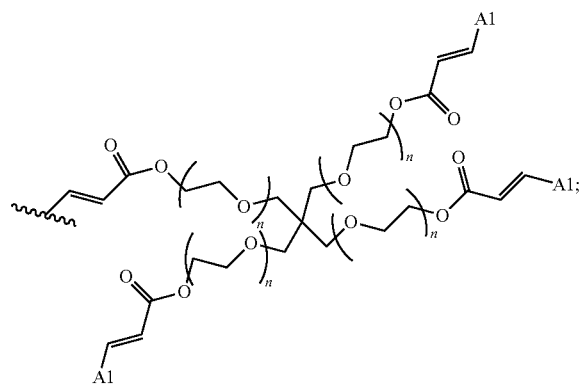

(I-Z)

wherein each A1 independently is an amine;
under suitable conditions,
such that a polymet of claim 2 is formed.

5. The polymer, pharmaceutically acceptable salt, co-crystal, tautomer, stereoisomer, or isotopically labeled derivative thereof, of claim 1, wherein the polymer is of the formula:

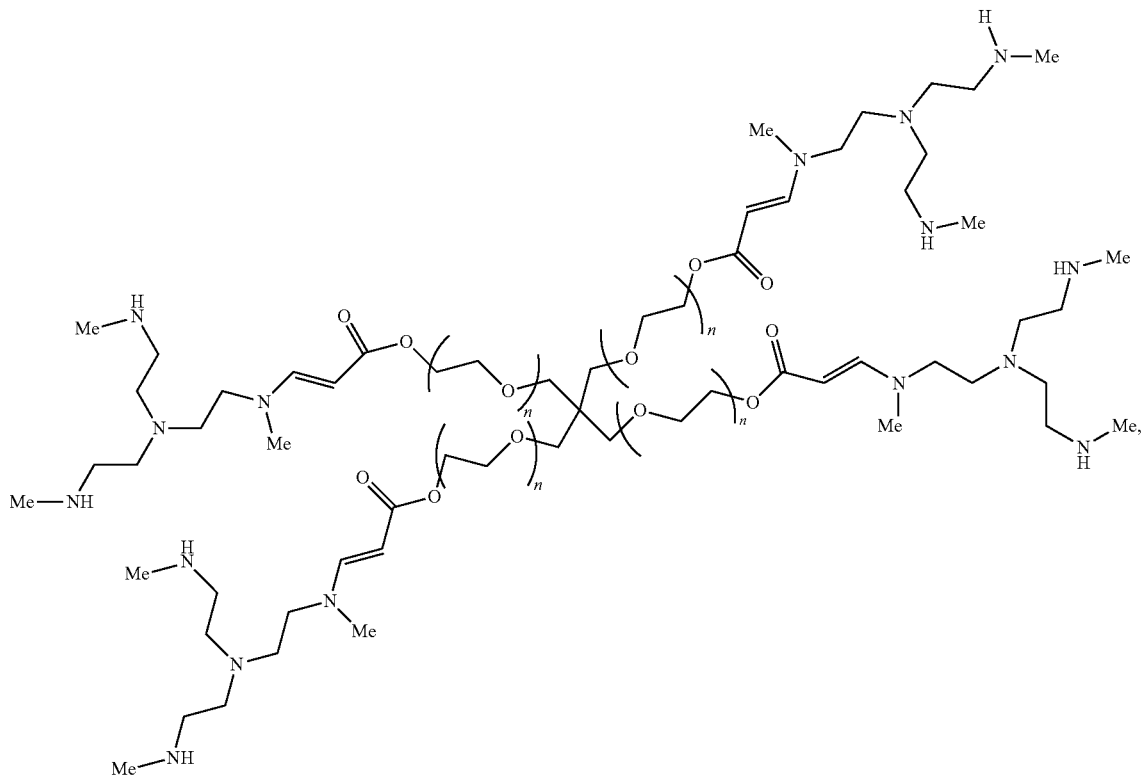

or a pharmaceutically acceptable salt, co-crystal, tautomer, stereoisomer, or isotopically labeled derivative thereof;
wherein each instance of n is between 25-135.

6. The polymer of claim 1, wherein the polymer is a hydrogel.

7. The polymer of claim 1, wherein the polymer forms a hydrogel.

8. A composition comprising a polymer, pharmaceutically acceptable salt, co-crystal, tautomer, stereoisomer, or isotopically labeled derivative thereof, of claim 1.

9. A kit comprising:
a polymer, pharmaceutically acceptable salt, co-crystal, tautomer, stereoisomer, or isotopically labeled derivative thereof, of claim 1, or a composition thereof; and
instructions for administering to a subject or contacting a cell, tissue, or biological sample with the polymer or the composition.

10. a composition comprising a polymer of claim 1, or a pharmaceutically acceptable salt, co-crystal, tautomer, stereoisomer, or isotopically labeled derivative thereof.

11. The composition of claim 10, wherein the agent is a therapeutic agent.

12. The composition of claim 11, wherein the therapeutic agent is a small molecule, nucleic acid, protein, peptide, polynucleotide, biologic.

13. A scaffold for tissue engineering comprising a composition of claim 8.

14. The scaffold of claim 13, wherein the scaffold comprises cells, growth factors, proteins, peptides, or cell binding domains.

15. The composition of claim 10, further comprising an agent.

16. A particle comprising a polymer of claim 1.

17. A method of delivering an agent to a subject in need thereof, the method comprising administering to the subject an effective amount of a polymer of claim 1, or a composition thereof.

18. A method of delivering an agent to a subject in need thereof, the method comprising administering to the subject an effective amount of a composition of claim 15.

19. A method of delivering an agent to a cell, tissue, or biological sample, the method comprising contacting the cell, tissue, or biological sample with an effective amount of a composition of claim 15.

20. The composition of claim 15, wherein the agent is a cosmetic agent.

21. The composition of claim 15, wherein the agent is a diagnostic agent.

22. The composition of claim 15, wherein the agent is a prophylactic agent.

23. A method of preparing a polymer, pharmaceutically acceptable salt, co-crystal, tautomer, stereoisomer, or isotopically labeled derivative thereof, comprising:
reacting a protein derivatized with an electrophile, a carbohydrate derivatized with an electrophile, or a tetra-arm polyethylene glycol alkynoate compound of Formula (A):

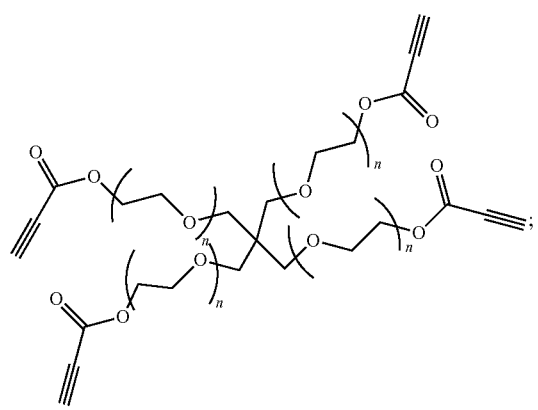

(A)

or a pharmaceutically acceptable salt, co-crystal, tautomer, stereoisomer, or isotopically labeled derivative thereof,
with an amine selected from the group consisting of: linear amines, branched amines, polyamines, cyclic amines, matrix metalloproteinase (MMP) degradable amines, redox sensitive amines, photocleavable amines, and
a compound of Formula (B):

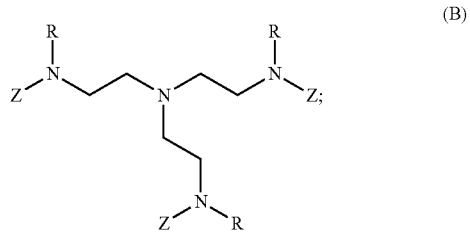

(B)

or a pharmaceutically acceptable salt, co-crystal, tautomer, stereoisomer, or isotopically labeled derivative thereof,
wherein:
each n independently is between 10-150;
each R independently is hydrogen, optionally substituted alkyl, optionally substituted alkenyl, or optionally substituted alkynyl;
each Z independently is hydrogen, optionally substituted alkyl, optionally substituted alkenyl, optionally substituted alkynyl, or of the Formula (I-Z):

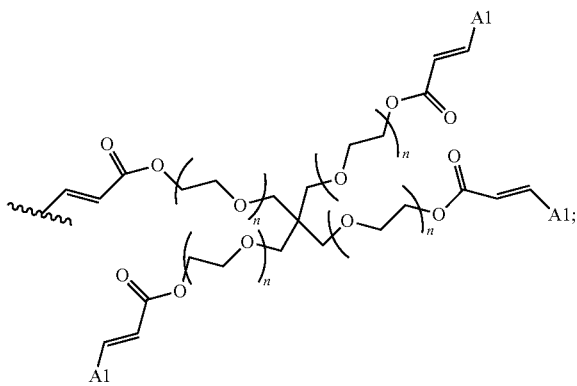

(I-Z)

wherein each A1 independently is an amine, and each n independently is between 10-150;
under suitable conditions.

* * * * *

UNITED STATES PATENT AND TRADEMARK OFFICE
CERTIFICATE OF CORRECTION

PATENT NO. : 11,491,228 B2
APPLICATION NO. : 16/502551
DATED : November 8, 2022
INVENTOR(S) : Robert S. Langer et al.

It is certified that error appears in the above-identified patent and that said Letters Patent is hereby corrected as shown below:

In the Claims

In Claim 4, at Column 131, Line 47, the text: "slkynyl, or the Formula (I-Z):" should be replaced with: --alkynyl, or the Formula (I-Z):--.

In Claim 4, at Column 132, Line 3, the text: "such that a polymet of claim 2 is formed" should be replaced with: --such that a polymer of claim 2 is formed--.

In Claim 8, at Column 132, Line 53, the text: "A composition" should be replaced with: --A particle--.

In Claim 10, at Column 132, Line 63, the text: "a composition" should be replaced with: --A composition--.

In Claim 11, at Column 132, Lines 66-67, the text: "The composition of claim 10, wherein the agent is a therapeutic agent." should be replaced with: --The composition of claim 10, further comprising water.--.

In Claim 12, at Column 133, Lines 1-3, the text: "The composition of claim 11, wherein the therapeutic agent is a small molecule, nucleic acid, protein, peptide, polynucleotide, biologic." should be replaced with: --The composition of claim 10, wherein the composition is a pharmaceutical composition.--.

In Claim 13, at Column 133, Lines 4-5, the text: "A scaffold for tissue engineering comprising a composition of claim 8." should be replaced with: --A scaffold for tissue engineering comprising a composition of claim 10.--.

In Claim 16, at Column 133, Line 11, the text: "A particle comprising a polymer of claim 1." should be replaced with: --The composition of claim 15, wherein the agent is a therapeutic agent.--.

Signed and Sealed this
Seventh Day of February, 2023

Katherine Kelly Vidal
*Director of the United States Patent and Trademark Office*

CERTIFICATE OF CORRECTION (continued)
U.S. Pat. No. 11,491,228 B2

In Claim 17, at Column 133, Lines 12-15, the text: "A method of delivering an agent to a subject in need thereof, the method comprising administering to the subject an effective amount of polymer of claim 1, or a composition thereof." should be replaced with: --The composition of claim 16, wherein the therapeutic agent is a small molecule, nucleic acid, protein, peptide, polynucleotide, biologic.--.